(12) United States Patent
Dowle et al.

(10) Patent No.: US 6,215,002 B1
(45) Date of Patent: Apr. 10, 2001

(54) PYRROLOPYRROLONE DERIVATIVES AS INHIBITORS OF NEUTROPHIL ELASTASE

(75) Inventors: Michael Dennis Dowle, Ware; Harry Finch, Letchworth; Lee Andrew Harrison, Biggleswade; Graham George Inglis, Kingswood; Martin Redpath Johnson, Royston; Simon John Fawcett MacDonald, Benington; Pritom Shah, Biggleswade; Robin Andrew Smith, St. Albans, all of (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/517,963

(22) Filed: Mar. 3, 2000

Related U.S. Application Data

(62) Division of application No. 09/418,644, filed on Oct. 15, 1999, now Pat. No. 6,057,457, which is a division of application No. 09/155,323, filed as application No. PCT/EP97/01530 on Mar. 26, 1997, now Pat. No. 5,994,344.

(30) Foreign Application Priority Data

Mar. 28, 1996 (GB) .................................................. 9606508
Nov. 5, 1996 (GB) .................................................. 9623001

(51) Int. Cl.[7] ........................ C07D 487/04; C07D 207/46
(52) U.S. Cl. ........................ 548/453; 548/531; 548/543
(58) Field of Search .................... 548/531, 543, 548/453

(56) References Cited

U.S. PATENT DOCUMENTS

| 2,932,650 | 4/1960 | Cope et al. ........................ 260/313 |
| 4,997,950 | * 3/1991 | Murphy et al. ........................ 548/303 |
| 5,484,946 | * 1/1996 | Abood et al. ........................ 548/543 |

FOREIGN PATENT DOCUMENTS

| WO93/24519 | 12/1993 | (WO) . |
| WO95/21855 | 8/1995 | (WO) . |

OTHER PUBLICATIONS

Prochazka et al., Collect. Czech. Chem. Comm. (1984), 49(3), pp. 642–652, Mar. 1984.*

Barlos et al., Liebigs Ann. Chem. (1988), (12), pp. 1127–1133, Dec. 1988.*

Kottirsch et al., Bioorg. Med. Chem. Lett. (1993), 3(8), pp. 1675–1680, 1993.*

Holladay, et al., "Synthesis of alpha–benzyl gamma–lactam, alpha–benzylpropolne derivatives as conformationally Irestricted analogs of phenylalaninamide", Journal of Org. Chem. (1991), 56(12), 3900–5.

* cited by examiner

*Primary Examiner*—Laura L. Stockton
(74) *Attorney, Agent, or Firm*—James P. Riek

(57) ABSTRACT

There are described according to the invention, processes for making compounds of formula $(XXVIII)^3$ (relative stereochemistry indicated), wherein $P_2$ is as defined in the specification.

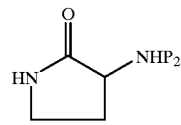

$(XXVIII)^3$

6 Claims, No Drawings

PYRROLOPYRROLONE DERIVATIVES AS INHIBITORS OF NEUTROPHIL ELASTASE

This application is a divisional of parent application U.S. Ser. No. 09/418,644, filed Oct. 15, 1999 now U.S. Pat. No. 6,057,457, to Dowle et al., (the entire contents of which are specifically incorporated herein by reference), which is a divisional of U.S. Ser. No. 09/155,323 now U.S. Pat. No. 5,994,344 to Dowle et al, filed Sep. 25, 1998, (the entire contents of which are specifically incorporated herein by reference) which was an application filed pursuant to 35 USC §371 as a United States Application of the International Application No. PCT/EP97/01530 filed Mar. 26, 1997, which claims priority from GB application no. 9606508.1 filed Mar. 28, 1996 and GB application no. 9623001.6 filed Nov. 5, 1996.

The present invention relates to therapeutically active bicyclic compounds, processes for the manufacture of said compounds, pharmaceutical formulations containing said compounds and the use of said compounds in chemotherapy. In particular, we have found a novel group of bicyclic compounds which are effective in treating inflammatory diseases.

Inflammation is a primary response to tissue injury or microbial invasion and is characterised by circulating leukocytes binding to and extravasation through vascular endothelium. Circulating leukocytes include neutrophils, eosinophils, basophils, monocytes and lymphocytes. Different forms of inflammation involve different types of infiltrating leukocytes.

The inflammatory process can be triggered in a number of ways, including by infection, tissue damage and autoimmune reactions. As part of the inflammatory process, neutrophils move from the bloodstream into the tissue at the site of tissue lesion. The neutrophils contain large numbers of different intracellular granules and when activated at the site of inflammation the contents of these granules are secreted into the tissue. The different granules contain a variety of enzymes and other proteins, many of which have antibacterial properties.

One of the enzymes found in the azurophilic granules is neutrophil elastase. Neutrophil elastase has a wide spectrum of activities in the body. For example, within the lung the enzyme increases mucus production and changes the cellular composition of the epithelium. The enzyme also causes vascular permeability changes within the microcirculation of many tissues and it is a potent destructive agent against a number of connective tissue components.

Although there are within the body endogenous inhibitors of elastase, including the anti-trypsin and the leukocyte protease inhibitor, elastase activity has been implicated in the pathogenesis of a number of disease states including inflammatory diseases of the airways, the joints and the skin. The enzyme is also responsible for some or most of the symptoms of acute respiratory distress syndrome (ARDS) and other acute inflammatory states brought about by trauma and/or sepsis.

We have now found a novel group of compounds which inhibit neutrophil elastase. The compounds are therefore of potential therapeutic benefit in the treatment and amelioration of symptoms of diseases where elastase activity is implicated.

Thus, according to one aspect of this invention, we provide a compound of the general formula (I)

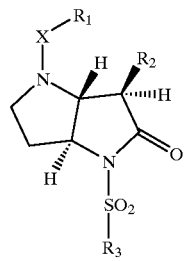

(I)

wherein:

$R_1$ represents $C_{1-6}$alkyl; $C_{2-6}$ alkenyl; aryl, aryl-$C_{1-4}$alkyl, aryl-$C_{2-4}$alkenyl, heteroaryl, heteroaryl-$C_{1-4}$ alkyl, or heteroaryl-$C_{2-4}$alkenyl, or such a group in which the aryl or heteroaryl moiety is substituted by one or more $C_{1-4}$alkyl, halo, tetrazolyl, trifluoromethylsulphonamide, $NR_9CO$—$C_{1-8}$alkyl, —$(CH_2)_m$—$NR_4R_5$, —CN, —$COOR_9$, —$CONR_9R_{10}$, —$NO_2$, —$SO_2$—$C_{1-6}$alkyl, —$CF_3$ or $C_{1-6}$alkoxy groups; —$(CH_2)_n$—$NR_4R_5$; $C_{2-8}$alkenyl-$NR_4R_5$; —$(CH_2)_n CONR_4R_5$; —$(CH_2)_n NR_9CO$—$C_{1-6}$alkyl; $C_{2-8}$alkenyl-$COOR_9$; $(CH_2)_n COOR_9$; and $C_{2-8}$alkenyl $CONR_4R_5$;

X, represents

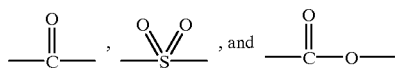

(where carbonyl is bound to the ring nitrogen);

$R_2$ represents $C_{2-4}$alkyl, $C_{2-4}$alkenyl, $C_{1-3}$alkoxy or $C_{1-3}$alkylthio;

$R_3$ represents $C_{1-6}$alkyl; —$CH_2(CF_2)_{0-4}CF_3$; aryl or heteroaryl, which aryl or heteroaryl are mono-ring, or have two fused rings one of which may be saturated, and which aryl and heteroaryl groups may be substituted by one or more $C_{1-4}$alkyl, halo, —$NR_7R_8$, —$SO_2NR_7R_8$, —$CONR_7R_8$, —$C_{1-6}$alkyl ester, —CN, —$CH_2OH$, —O—$C_{1-6}$alkyl, —$CF_3$, or nitro groups; aryl-$C_{1-4}$alkyl, aryl-$C_{1-4}$alkyl-NH— or aryl-$C_{2-4}$ alkenyl, or such groups wherein aryl is substituted by one or more $C_{1-4}$alkyl or halo groups;

$R_4$ and $R_5$ independently represent hydrogen, $C_{1-4}$ alkyl, $C_{1-4}$alkoxy, —$(CH_2)_{1-4}CONR_{11}R_{12}$, —CO—$C_{1-4}$alkyl or phenyl optionally substituted by one or more $C_{1-4}$alkyl or halogen groups or $R_4$ and $R_5$ may be joined such that $NR_4R_5$ represents a mono, bi- or tri-cyclic ring system containing –15 ring carbon atoms, wherein one or more rings may be optionally interrupted by one or more heteroatoms selected from O, N and S and wherein one or more ring carbon atoms may have carbonyl functionality;

or —$(CH_2)_n$—$NR_4R_5$ may represent a group of formula 1a:

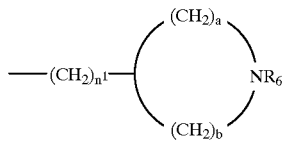

(1a)

wherein $R_6$ is hydrogen or a carboxy $C_{1-6}$ alkyl ester, $n^1$ is 0–6 and a and b independently represent an integer 0–3 provided a+b is in the range 3–5;

$R_7$, $R_8$, $R_9$, $R_{10}$, $R_{11}$, $R_{12}$ independently represent hydrogen or $C_{1-4}$ alkyl;

m represents an integer 0 to 8; n represents an integer 1 to 9;

and salts and solvates thereof.

Formula (I) shows the relative stereochemistry of the chiral centres. The invention embaces compounds of formula (I) in racemic form as well as in a form in which one enantiomer predominates or is present exclusively. Generally, we prefer to provide a compound of formula (I) in enantiomerically pure form.

When used herein "alkyl" includes branched as well as straight chain alkyl and may also include cycloalkyl when 3 or more carbon atoms are present.

When $R_4$ and $R_5$ are joined such that —$NR_4R_5$ represents a mono- bi- or tri-cyclic ring system, one or more rings may be unsaturated or aromatic. Examples of ring systems which —$NR_4R_5$ may represent include unsaturated monocycles such as azetidine, pyrrolidine, piperidine, azepine, piperazine, morpholine; bicycles such as dihydrosoquinoline, tetrahydrosoquinoline, octahydroisoquinoline, desmethyl tropane; and tricycles such as hexahydrobenzoisoindole. Carbonyl containing ring systems include pyrrolone (e.g. pyrrol-2-one) and oxopyridine (e.g. 2-oxo-2H-pyridine and 4-oxo-4H-pyridine). Ring carbon atoms may be substituted by $C_{1-4}$ alkyl, CONR'R", COOR' (R', R" independently represent hydrogen or $C_{1-4}$ alkyl) or halogen groups and ring nitrogen atoms may be substituted by $C_{1-4}$ alkyl or —CO—$C_{1-4}$alkyl groups. Particularly suitable carbon substituents include methyl (for example as in 2,5-dimethyl pyrrolidine and 2,6-dimethyl piperidine), —$CONH_2$ (for example as in 4-($H_2NCO$)-piperidine) and —COOMe (for example as in 2-(MeOCO)-pyrrolidine). Suitable nitrogen substituents include methyl (for example as in 4-methyl-piperazine), and —COMe (for example as in 4-(MeCO)-piperazine).

Suitable $R_4$, $R_5$ alkyl groups include methyl, ethyl, n-propyl, isopropyl and cyclopropyl.

Suitable $R_4$,$R_5$ alkoxy groups include methoxy.

Suitable $R_4$,$R_5$—$(CH_2)_{1-4}CONR_{11}R_{12}$ groups include —$CH_2CONH_2$.

Suitable $R_4$,$R_5$—CO—$C_{1-4}$alkyl groups include —COMe.

Suitable $R_1$ alkyl groups include methyl, ethyl and propyl.

Suitable $R_1C_{2-6}$ alkenyl groups include CH=CH—$CH_3$.

Suitable $R_1$ aryl groups have up to two rings. They suitably include phenyl and naphthyl, most suitably phenyl.

Suitable $R_1$ arylalkyl groups include phenylmethyl and phenylethyl.

Suitable $R_1$ arylalkenyl groups include styryl.

Especially suitable $R_1$ aryl substituents include $C_{1-4}$ alkyl, such as methyl or ethyl; $C_{1-6}$ alkoxy, such as methoxy, ethoxy and n-butyloxy; halo such as chloro, bromo or iodo; —$SO_2C_{1-6}$ alkyl, such as —$SO_2Me$; tetrazolyl bonded through carbon; —$CF_3$; —$NO_2$; —CN; —$(CH_2)_m$—$NR_4R_5$ such as —$NH_2$, —$CH_2NH_2$, —$CH_2NH$(cyclopropyl), —$CH_2N(Me)(nPr)$, —$CH_2$(4-Me-piperazin-1-yl) and 2-oxopyrrolidin-1-yl; and —$NR_9COC_{1-8}$ alkyl such as —NHCOMe. Often there will be 1, 2 or 3 such substituents.

Suitable $R_1$ heteroaryl groups include those containing sulphur, nitrogen or oxygen heteroatoms. Suitable $R_1$ heteroaryl groups will have up to two rings. Examples include imidazolyl, optionally N-substituted by $C_{1-4}$alkyl; pyridyl; furanyl; pyrrolyl and thienyl.

Suitable $R_1$ heteroaryl alkyl and alkenyl groups include pyridylmethyl, pyridylethyl and pyridylethenyl.

Suitable $R_1$ heteroaryl substituents include those as described above in regard to aryl substituents.

Suitable —$(CH_2)_n$—$NR_4R_5$ groups for $R_1$ also include those of the above formula (Ia) in which $n^1$ is 0, a is 2 and b is 2 or $n^1$ is 0, a is 0 and b is 3. $R_6$ carboxy alkyl ester groups include t-butyl.

Suitable $R_1$ $C_{2-8}$ alkenyl $NR_4R_5$ groups especially include —CH=CH—$CH_2$—$NR_4R_5$ groups. Suitable such $NR_4R5$ groups include morpholine, azepine; pyrrolidine (optionally substituted by COOMe or methyl); piperidine (optionally substituted by —$CONH_2$ or methyl); piperazine (optionally 4-substituted by methyl or —MeCO); —$NHC_{1-4}$ alkyl, such as —NH(cyclopropyl) and —NH(iPr); —$N(C_{1-4}alkyl)_2$, such as —NMe(nPr), —$N(iPr)_2$, —$N(Et)_2$—$N(Me)_2$; and —$N(C_{1-4}alkyl)(C_{1-6}alkoxy)$ such as —NMe(OMe).

Suitable $R_1$—$(CH_2)_n$ $CONR_4R_5$ groups include —$(CH_2)_2$ $CONH_2$.

Suitable $R_1$—$(CH_2)_n NR_9COC_{1-6}$ alkyl groups include —$(CH_2)_2$ NHCOMe and —$CH_2$ NHCOMe.

Suitable $R_1$ —$(CH_2)_n$—$COOR_9$ groups include —$CH_2COOH$, —$CH_2COOMe$, —$(CH_2)_2COOH$ and —$(CH_2)_2COOMe$.

Suitable $R_1$—$C_{2-8}$alkenyl—$COOR_9$ groups include —CH=CH—COOEt and —CH=CH—COOH.

Suitable $R_1$—$C_{2-8}$alkenylCONR_4R_5$ groups include CH=CH—CO—(4-methyl-1-piperazine).

Preferred $R_1$ groups include $C_{2-8}$ alkenyl-$NR_4R_5$; phenyl, furanyl, thiophenyl or pyrrolyl substituted by the group $(CH_2)_n'$—$NR_4R_5$ (wherein n' represents an integer 1 to 5) and phenyl substituted by —NHCO—$C_{1-8}$alkyl. Particularly preferred $R_1$ groups include those just defined in which $NR_4R_5$ together represents morpholine, pyrrolidine, piperidine, azepine, piperazine or 4-methyl-piperazine or one or both of $R_4$ and $R_5$ represent $C_{1-4}$ alkyl (for example, methyl, n-propyl or cyclopropyl) and the other it is does not represent $C_{1-4}$ alkyl) represents hydrogen. It is also preferred that n' represents an integer 1 to 3, particularly 1. When $R_1$ represents phenyl substituted by —NHCO—$C_{1-8}$alkyl, the preferred $C_{1-8}$alkyl group is methyl.

When $R_1$ represents $C_{2-8}$ alkenyl-$NR_4R_5$, the preferred group is $C_{3-6}$alkenyl-$NR_4R_5$, particularly CH=CH—$CH_2$—$NR_4R_5$.

Preferred X groups include —CO— and —$SO_2$—. It is particularly preferred that X represents —CO—.

Suitable $R_2$ alkyl groups include ethyl, n-propyl and isopropyl.

Suitable $R_2$ alkenyl groups include —$CH_2$—CH=$CH_2$.

Suitable $R_2$ alkoxy and alkylthio groups include methoxy and methylthio.

We prefer $R_2$ to represent $C_{2-4}$alkyl, especially n-propyl or isopropyl, most especially isopropyl.

Suitable $R_3$ alkyl groups include methyl, ethyl and propyl, especially methyl.

Suitable $R_3$ —$CH_2(CF_2)_{0-4}$ $CF_3$ groups include $CH_2$ $CF_3$.

Suitable $R_3$ aryl groups include phenyl, naphthyl, and tetrahydronaphthalene.

Suitable substituents of such $R_3$ aryl groups include $NH_2$, $N(CH_3)_2$, $SO_2N(CH_3)_2$, $NO_2$, and alkyl, alkoxy and halo groups stated to be suitable above regarding $R_1$ aryl substituents. Suitable other substituents also include $CONH_2$, methyl ester (—COOMe) and methoxy.

Suitable $R_3$ heteroaryl groups include those containing sulphur, nitrogen or oxygen, such as benzothiophenyl, benzothiadiazolyl, thiophenyl, isoxazolyl, pyridinyl, quinolinyl, isoquinolinyl, tetrahydroquinolinyl, and tetrahydroisoquinolinyl. Suitable substituents for such groups include those $R_3$ aryl substituents mentioned above.

Suitable $R_3$ arylalkyl and arylalkyl amino groups include phenylmethyl, phenylethyl, phenylpropyl, phenylmethylamino and phenylethylamino. Suitable $R_3$ aralkenyl groups include styryl. Suitable substituents for such $R_3$ groups include alkyl (especially methyl) or halo, We prefer $R_3$ to represent $C_{1-6}$ alkyl, especially methyl or ethyl, most especially methyl.

$R_7$, $R_8$, $R_9$, $R_{10}$, $R_{11}$, and $R_{12}$ preferably represent hydrogen or methyl.

n preferably represents an integer 1 to 5, more preferably an integer 1 to 3, particularly 1.

m preferably represents an integer 0 to 3, especially 1 or 2.

Where compounds of formula (I) are able to form salts the present invention covers the physiologically acceptable salts of the compounds of formula (I). Suitable physiologically acceptable salts of the compounds of formula (I) include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine). procaine, ethanolamine, diethanolamine, N-methylglucosamine and tri(hydroxymethyl)methylamine salts and amino acid salts (e.g. lysine and arginine salts). Suitable inorganic and organic acid salts include the hydrochloride, trifluoroacatate and tartrate.

The most preferred compounds of the invention have structure as follows:

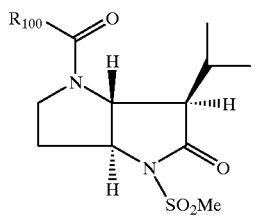

(relative stereochemistry indicated)

wherein $R_{100}$ represents a moiety of formula —CH=CH—$CH_2$-piperidin-1-yl (E-isomer), CH=CH—$CH_2$—NH(cyclopropyl) (E-isomer), -phenyl-4-[$CH_2$(4-methylpiperazin-1-yl)], phenyl-4 [$CH_2$—NH(cyclopropyl)] or phenyl-4-[$CH_2$N(Me)(n-propyl)]. The (3S, 3aS, 6aR) enantiomer is particularly preferred.

The potential for compounds of formula (I) to inhibit neutrophil elastase activity may be demonstrated, for example, using the following in vitro and in vivo assays:

In Vitro Assays of Human Neutrophil Elastase

Assay contents:
50 mM Tris/HCl (pH 8.6)
150 mM NaCl
118 nM purified human neutrophil elastase
Suitable concentrations of compound under test diluted with water from a 10 mM stock solution in dimethylsulphoxide. Values above are final concentrations after the addition of substrate solution (see below).

The mixture above is incubated for fifteen minutes at 30° C. at which time the remaining elastase activity is measured for 10 minutes in a BioTek 340i plate-reader, after the addition of 0.6 mM MeO-succinyl-alanyl-alanyl-prolyl-valyl-p-nitroanilide. The rate of increase in absorbance at 405 nm is proportional to elastase activity. Enzyme activity is plotted against concentration of inhibitor and an $IC_{50}$ determined using curve fitting software.

In Vivo Activity of Inhibitors of Human Neutrophil Elastase

Female hamsters (100–150 g) are anaesthetised and 0.1 ml of vehicle (7% dimethylsulphoxide) or inhibitor solution is instilled (via a small incision) into the trachea. At a specified time after application of inhibitor human neutrophil elastase (75 international units in 0.1 ml) is instilled by the same route. 45 minutes after instillation of elastase animals are sacrificed. Sterile saline is delivered to the lungs via a 23 gauge cannula attached to a hypodermic syringe. After flushing five times with 2.5 ml aliquots, bronchoalveolar lavage fluid (approximately 1.52–2.0 ml) is collected. Lavage fluids are diluted with an equal volume of 2% sodium carbonate solution. Sonication is used to ensure cellular disruption prior to spectrophotometric determination of haemoglobin concentration. The level of haemorrhage is expressed as concentration of haemoglobin and the effects of an elastase inhibitor expressed as % inhibition of haemorrhage in comparison to a vehicle control.

Accordingly, compounds of formula (I) are of potential therapeutic benefit in the treatment and amelioration of symptoms of diseases where elastase activity is implicated. Such diseases particularly include bronchitis, including chronic bronchitis. Also any chronic obstructive pulmonary disease (COPD).

Examples of disease states in which the compounds of the invention have potentially beneficial effects include inflammatory diseases of the respiratory tract such as bronchitis (including chronic bronchitis), bronchiectasis, asthma and hyper-reactivity states of the lung, acute respiratory distress syndrome and septic shock, inflammatory or destructive conditions of the lung such as emphysema and cystic fibrosis and inflammatory or destructive conditions of external tissue such as skin diseases (e.g. lupus and psoriasis) and periodontal disease including gingivitis.

Further examples of disease states and conditions in which compounds of the invention have potentially beneficial effects include wound healing and treatment of burns, cardiovascular diseases such as myocardial infarction and stroke, peripheral vascular disease including intermittent claudication, atherosclerosis, reperfusion injury, cardiovascular changes occurring during cardiopulmonary bypass surgery and septicemia.

Compounds of the invention may also be useful in the treatment of connective tissue disorders such as rheumatoid arthritis, osteoarthritis and spondylitis and inflammatory conditions of the kidney such as glomerulonephritis.

They may also be useful in the treatment of certain leukemias including acute myelogenous leukemia, acute myelomonocytic leukemia and the chronic monocytic leukemias and in prevention or inhibition of metastasis of solid tumours e.g. lung, breast, prostate and stomach cancers and melanomas.

A particular aspect of the present invention is the use of compounds of formula (I) in the treatment of chronic bronchitis. Chronic bronchitis is a condition which results from the exposure of the airway surface to noxious chemicals or agents or is secondary to another disease. The symptoms of the condition are caused by the excessive secretion of mucus onto the surface of the airways. This excess mucus cannot be cleared effectively and the result is reduced gas exchange within the lungs resulting in laboured breathing and hypoxemia, recurrent microbial infections and persistent cough associated with the expectoration of mucoid material. The proposed mechanism for the excessive secretion of mucus involves the recruitment of neutrophils into the airways following the exposure of the epithelium to irritant materials; the neutrophils secrete elastase onto the surface of the airways and the enzyme brings about both an increase in the amount of mucus secreted onto the airway surfaces and a dramatic change in the cellular composition of the airway epithelium. Inhibition of elastase activity by the administration of compounds of this invention is therefore an approach to the treatment of chronic bronchitis. Reduced lung function in COPD (eg in chronic bronchictics with airflow obstruction) is also due to elastase mediated lung damage leading to airway narrowing and inflammation. Thus an elastase inhibitor will improve lung function.

As indicated above, compounds of formula (I) are useful in human or veterinary medicine, in particular as inhibitors of the enzyme neutrophil elastase.

Thus, there is provided as a further aspect of the present invention a compound of formula (I) or a physiologically acceptable salt or solvate thereof for use in human or veterinary medicine, particularly in the treatment of conditions where elastase activity is implicated such as chronic bronchitis.

It will be appreciated that references herein to treatment extend to prophylaxis as well as the treatment of established conditions.

According to another aspect of the invention, there is provided the use of a compound of formula (I) or a physiologically acceptable salt or solvate thereof for the manufacture of a medicament for the treatment of conditions where elastase activity is implicated, particularly in chronic bronchitis.

In a further or alternative aspect there is provided a method for the treatment of a human or animal subject with a condition caused or mediated by elastase activity which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in therapy, comprising a compound of formula (I) or a physiologically acceptable salt or solvate thereof in admixture with one or more physiologically acceptable diluents or carriers.

There is also provided according to the invention a process for preparation of such a pharmaceutical composition which comprises mixing the ingredients.

The compounds according to the invention may, for example, be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize- starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucosel/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buscal administration the compositions may take the form of tablets or lozenges formulated in conventional manner.

The compound may also be formulated as suppositories, e.g. containing conventional suppository bases such as cocoa butter or other glycerides.

The compound according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutic agents, for example anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), lung surfactants and/or antimicrobial and anti-viral agents. The compositions according to the invention may also be used in combination with gene replacement therapy.

The invention thus provides, in a further aspect, a combination comprising a compound of formula (I) or a physiologically acceptable salt or solvate thereof together with another therapeutically active agent.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

Compounds of the invention may conveniently be administered in amounts of, for example, 0.01 to 50 mg/kg body weight, suitably 0.05 to 25 mg/kg body weight orally, one or more times a day. The precise dose will of course depend on the age and condition of the patient, the particular route of administration chosen, and the disease being treated. The compounds specifically named earlier are preferably administered orally for the treatment of bronchitis. Other routes of administration may be needed for other indications, for instance i.v. for ARDS.

The compounds of the formula (I) have useful duration of action.

The compounds of formula (I) and salts and solvates thereof may be prepared by the methodology described hereinafter, constituting a further aspect of this invention.

A process according to the invention for preparing a compound of formula (I) comprises:

(i) condensation of a compound of formula (II):

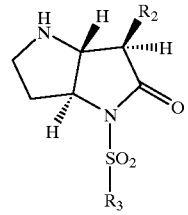

(II)

with a compound $R_1COOH$, $RCOY$, $R_1OCO.Y$ or $R_1SO_2Y$, where Y is a reactive group such as halogen; or (ii) sulphonylation of a compound of formula (III):

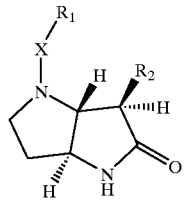

(III)

with a compound $YO_2SR_3$, wherein Y is a reactive group such as halogen, e.g. chlorine; or (iii) preparation of a compound of formula (I) wherein X is

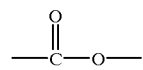

by reacting a compound of formula (IV)

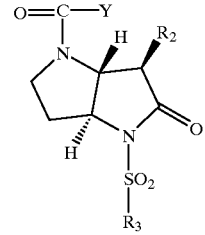

(IV)

with a compound $R_1$ OH, wherein Y is a reactive group such as those noted above; or (iv) preparation of a compound of formula (I) in which $R_2$ represents $C_{2-4}$ alkyl or $C_{2-4}$ alkenyl by reacting a compound of formula (V)

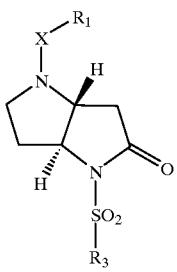 (V)

sequentially with a base and then with a compound $R_2'Y$, wherein Y is a reactive group such as those noted above and $R_2'$ represents $C_{2-4}$alkyl or $C_{2-4}$alkenyl; or (v) cyclising a compound of formula (VI):

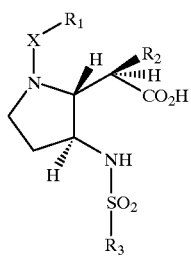 (VI)

or a carboxylic acid ester thereof; or (vi) preparation of a compound of formula (I) wherein X represents

by oxidising a compound of formula (VII)

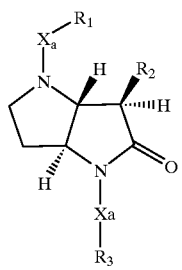 (VII)

wherein $X_a$ is sulphur or SO; or (vii) preparation of a compound of formula (I) by oxidising a corresponding compound of formula (VIII)

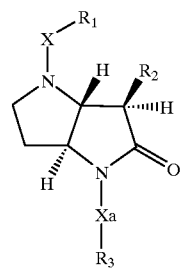 (VIII)

wherein Xa is sulphur or SO; or (viii) preparation of a compound of formula I in which $R_1$ represents aryl substituted by $-(CH_2)_{m'}NR_4R_5$ wherein m' represents an integer 1 to 8 by reductive amination of a corresponding compound of formula (IX)

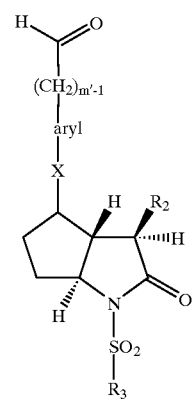 (IX)

with a compound of formula $HNR_4R_5$; or (ix) preparation of a compound of formula I in which $R_1$ represents $-(CH_2)_nNR_4R_5$ by reductive amination of a corresponding compound of formula (X)

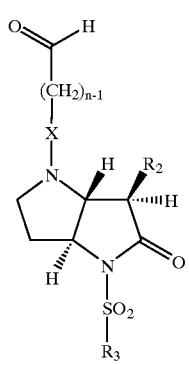 (X)

with a compound of formula $HNR_4R_5$; or (x) preparation of a compound of formula I in which $R_1$ represents aryl substituted by $-(CH_2)_{m'}NR4R_5$ wherein m' represents an integer 1 to 8 by reaction of a corresponding compound of formula (XI)

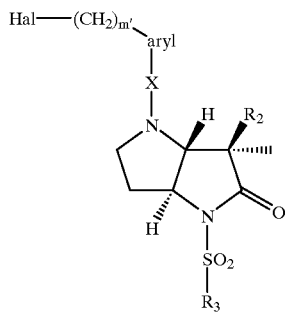

(XI)

wherein Hal represents a halide especially chlorine or bromine with a compound of formula $HNR_4R5$; or (xi) preparation of a compound of formula I in which $R_1$ represents —$(CH_2)_n NR_4R_5$ or $C_{2-8}$ alkenyl $NR_4R_5$ by reaction of a corresponding compound of formula (XII)

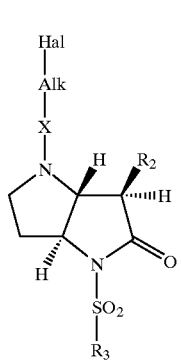

(XII)

wherein Alk represents $C_{2-8}$ alkenyl or —$(CH_2)_n$— and Hal represents a halide especially chlorine or bromine with a compound of formula $HNR_4R_5$; or (xii) preparing a compound of formula (I) wherein $R_1$ contains a N—$C_{1-4}$ alkyl piperazinyl moiety which comprises alkylating a corresponding compound of formula (I) wherein the piperazine is unalkylated; or (xiii) preparing a compound of formula (I) wherein $R_1$ contains a N—$C_{1-4}$ alkyl piperazinyl moiety which comprises performing a reductive alkylation on a corresponding unalkylated compound of formula (I); or (xiv) converting one compound of the formula (I) into another compound of the formula (I); or (xv) purifying one enantiomer of the compound of formula (I) from its racemic mixture;

and where desired or necessary converting a resultant free acid or base compound of formula I into a physiologically acceptable salt form or vice versa or converting one salt form into another physiologically acceptable salt form.

Process (i)

The condensation reaction with $R_1COOH$ is suitably carried out in the presence of a coupling agent such as 1-(3-N,N-dimethylaminopropyl)-3-ethylcarbodiimide, and a solvent such as dichloromethane, DMF or tetrahydrofuran at a temperature of suitably between 0° C. and ambient. It will be appreciated that as an alternative to using $R_1COOH$, acid derivatives such as the acid chloride, acid anhydride, or a mixed anhydride may be used. Reaction conditions will be modified accordingly, for instance by inclusion of a base.

With $R_1SO_2Y$ and $R_1OCO.Y$, the reaction is suitably carried out in the presence of a base such as triethylamine, and a solvent such as DCM, suitably at 0° C.-ambient.

Process (ii)

The sulphonylation reaction is suitably carried out in the presence of lithium bis(trimethylsilyl)amide (LHMDS), or NaH, in a solvent such as tetrahydrofuran at a temperature of suitably between −78° C. to 0° C.

Process (iii)

This reaction is suitably carried out in the presence of an organic base such as triethylamine, and a solvent such as dichloromethane, at a temperature of suitably 0°–25° C.

Process (iv)

This reaction is suitably carried out in the presence of a strong base, such as LHMDS, in the presence of a solvent such as tetrahydrofuran, at a reduced temperature such as −78° to 0° C.

Process (v)

The cyclisation reaction is suitably carried out in the presence of 2-chloro-1-methylpyridinium iodide, or 1-(3-N, N-dimethylaminopropyl)-3-ethylcarbodiimide (EDC), in a solvent such as dichloromethane, at a temperature of suitably 0° C.-reflux. This reaction may also be performed using a carboxylic acid thioester derivative of the compound of formula (VI).

Processes (vi) and (vii)

These oxidation reactions may be carried out in conventional manner such as by peracid oxidation.

Processes (viii) and (ix)

The reductive amination reaction may be performed by treating the aldehyde with amine in the presence of acid e.g. acetic acid in an inert solvent such as DCM or THF followed by addition of a mild reducing agent such as sodium triacetoxyborohydride.

Processes (x) and (xi)

These reaction may be performed by combining the reactants optionally in the presence of a base such as triethylamine or potassium carbonate in an inert aprotic solvent such as DMF or MeCN. It should be noted in connection with reaction (XI) that we have observed a tendency for an α-alkenyl halide to rearrange during the reaction to form a β-alkenyl amine.

Process (xii)

This reaction may be performed by treating the piperazinyl containing compound with an alkyl halide (eg methyl bromide), optionally with prior abstraction of a proton (e.g. with base, nBuLi).

Process (xiii)

The reductive alkylation may be performed by first producing an iminium intermediate by reaction of the unalkylated piperazinyl compound of formula (I) with a carbonyl containing compound (e.g. formaldehyde) under conventional conditions, for example in an inert solvent (such as DCM) in the presence of acid e.g. glacial acetic acid and then reducing it with a reducing agent e.g. sodium cyanoborohydride or sodium triacetoxyborohydride.

Process (xiv)

Examples of typical interconversions include reducing a $NO_2$ group to $NH_2$, and alkenyl group to alkyl; the partial or complete reduction of an aryl or heteroaryl system; and the removal of N-protecting groups such as t-butoxycarbonyl or CBZ (benzyloxycarbonyl). Such reactions may be carried out in a conventional manner, for instance by hydrogenation over palladium on carbon in solvents such as ethyl acetate or tetrahydrofuran.

Process (xv)

Purification of a single enantiomer may be achieved by conventional methods such as chiral chromatography (e.g. chiral HPLC) and crystallisation with a homochiral acid (e.g. tartaric acid).

Physiologically acceptable base salts of the compounds of formula (I) may conveniently be prepared by treating a compound of formula (I) with a suitable base such as a bicarbonate, e.g. sodium bicarbonate, in the presence of a suitable solvent. Acidsalts such as the hydrochloride, trifluoroacetate or tartrate may be prepared by treating a basic compound of formula (I) with the desired acid.

Intermediate compounds of formula (II) may conveniently be prepared according to the methodology in Scheme I below:

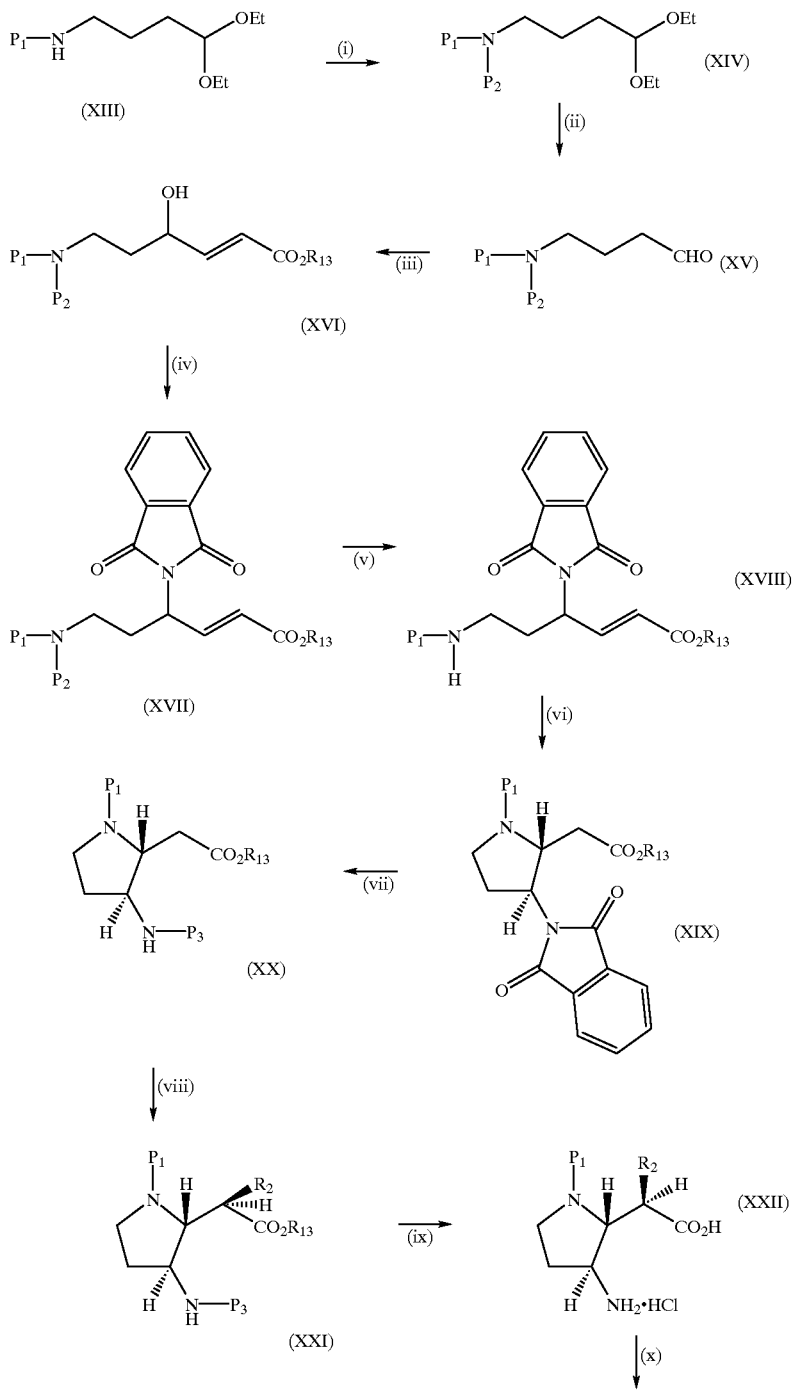

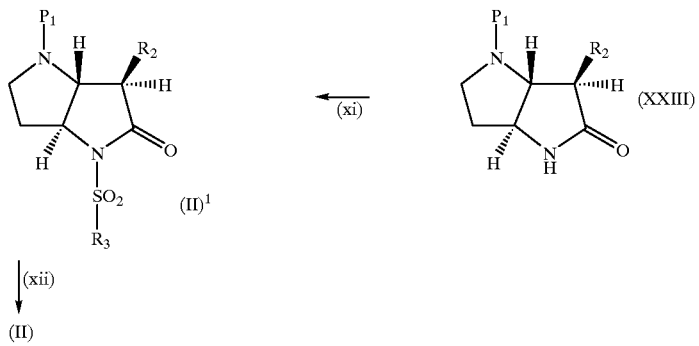

Step (i)

The compounds of formula (XIII) are either known compounds or may be made in analogous manner to known compounds. $P_1$ is a N-protecting group, preferably CBZ (benzyloxycarbonyl). Step (i) is a further N-protection reaction. $P_2$ in formula (XIV) is a different N-protecting group, preferably BOC (t-butyloxy carbonyl). When $P_2$ is BOC, the reaction is suitably carried out using $BOC_2O$.

Suitably the reaction is carried out in the presence of a base such as triethylamine or 4-dimethylaminopyridine in a solvent such as ethyl acetate, at temperature of suitably 0°–25° C.

Step (ii)

This conversion is suitably carried out with pyridinium p-toluenesulfonate, in a solvent such as acetone/water, at a temperature suitably between 25°–75° C.

Step (iii)

This is a condensation rearrangement reaction suitably carried out using a 2-phenylsulfinyl acetic acid ester ($PhSOCH_2$ $CO_2R_{13}$) and piperidine, in a solvent such as acetonitrile, suitably at ambient temperature.

$R_{13}$ is suitably a $C_{1-6}$alkyl group, preferably methyl.

Step (iv)

This is a Mitsunobu substitution reaction, using phthalimide, $PPh_3$ (triphenylphosphine) and DEAD (diethylazodicarboxylate), in the presence of a solvent such as THF, at a temperature of suitably 0°–40° C.

Step (v)

This is a deprotection reaction, preferably using a strong acid such as TFA in a solvent such as DCM, at a temperature of suitably 0°–40° C.

Step (vi)

This is a cyclisation reaction, suitably carried out as an intramolecular Michael reaction. Suitably NaH is used, in a solvent such as THF, at a temperature such 0°–25° C.

Step (vii)

In this step two reactions occur N-deprotection and re-protection. The phthalimido group is removed suitably with hydrazine hydrate in a solvent such as ethanol at a temperature between 0° C. and reflux. Protecting group $P_3$ is incorporated in a conventional manner. When $P_3$ is BOC, this is suitably achieved with $BOC_2O$.

Step (viii)

When $R_2$ represents alkyl or alkenyl, the $R_2$ side chain may be introduced by alkylation, using as reactant $R_2$—Y, wherein Y is a reactive group such as bromo or iodo. Thus the reaction is carried out using a base, preferably a strong base such as LHMDS. With LHMDS suitably a cosolvent DMPU in THF is used. Suitable reaction temperatures are −78° to 50° C. Under these conditions the reaction generally takes place with good stereochemical control.

When $R_2$ represents thioalkyl, the reaction may be performed by treatment of the compound of formula (XX) with t-butylmagnesium chloride and lithium bis(trimethylsilyl) amide followed by an alkyl disulphide. The reaction is preferably performed in a low polarity solvent, e.g. THF or a mixture of THF and N,N,N',N'-tetramethylethylenediamine at a temperature below 0° C. When $R_2$ represents alkoxy, the reaction may be performed by preparation of an intermediate hydroxy compound using the reagents potassium hexamethyldisilazide and 3-phenyl-2-(phenylsulphonyl) oxaziridine sequentially (typically at −78° C. in THF) followed, after purification, by treatment of the intermediate hydroxy compound with an alkyl halide (especially the iodide) in the presence of silver (I) oxide.

Step (ix)

This is an ester hydrolysis reaction, followed by a N-deprotection reaction. The former is carried out in a conventional manner, for example by using KOH in aqueous ethanol, at a temperature of suitably 25°–80° C. The latter is carried out in a conventional manner, for example by using HCl in dioxan, at a temperature of suitably 0°–50° C. or, if the protecting group is trifluoroacetate by treatment with base.

Step (x)

This is a cyclocondensation reaction, suitably carried out in the presence of 2-chloro-1-methylpyridinium iodide and a suitable base such as N,N-diisopropyl ethylamine in a solvent such as dichloromethane, at a temperature of suitably 0° C.-reflux. We have also found that it is possible to use the compound of formula (XXII) as a carboxylic acid ester in which case the ester hydrolysis of step (ix) is not necessary. In this case the preferred conditions for the cyclocondensation reaction involve the use of an alkyl Grignard reagent eg t-BuMgCl in THF at a temperature between −20° C. and 25° C.

Step (xi)

This is a lactam sulphonylation reaction. It is suitably carried out by reaction with $R_3SO_2$—Y, wherein Y is a reactive group, preferably chloro, in the presence of LHMDS, NaH or KH, in a solvent such as THF, at a temperature of suitably −78° to 0° C.

Step (xii)

This is a N-deprotection reaction, which can suitably be carried out in conventional manner. Thus when $P_1$ is CBZ, it is suitably carried out by hydrogenation over Pd $(OH)_2$ catalyst in solvents such as ethyl acetate or THF.

Intermediate compounds of the formula (III) may be prepared by reacting a deprotected compound of formula (XXIII) from Scheme 1 with $R_1COOH$, $R_1$ $SO_2Y$ or $R_1OCO.Y$, in the manner described above in relation to Process (i).

(The initial N-deprotection may be carried out as described above under Step (xii))

Intermediate compounds of formula (IV) may be prepared from a compound of formula (II), for example by reaction with triphosgene, in a solvent such as DCM, at a temperature of suitably 0°–25° C.

Intermediate compounds of formula (V) may be prepared by a process analogous to that for a compound of formula (I) prepared via a compound of formula (II) and Scheme 1, but wherein the alkylation step (viii) was omitted.

This latter process generates intermediates (XXIIa) and (XXIIIa) which have structures corresponding to those of intermediates (XXII) and (XXIII) save that $R_2$ represents hydrogen.

Intermediate compounds of formula (VI) may be prepared from a compound of formula (XXII) in an analogous manner to that described above for preparing a compound of formula (III) from a compound of formula (XXIII) together with main process (ii) above.

Intermediate compounds of the formula (VII) may be prepared by reacting a compound of formula (II) with a suitable $R_1$ sulphenyl or sulphinyl halide, in conventional manner.

In the case in which $R_2$ is a bulky alkyl, alkylthio or alkenyl group (especially i-Pr or t-Bu) we find it preferable to prepare compounds of formula (XXI) following Scheme 2 set out below:

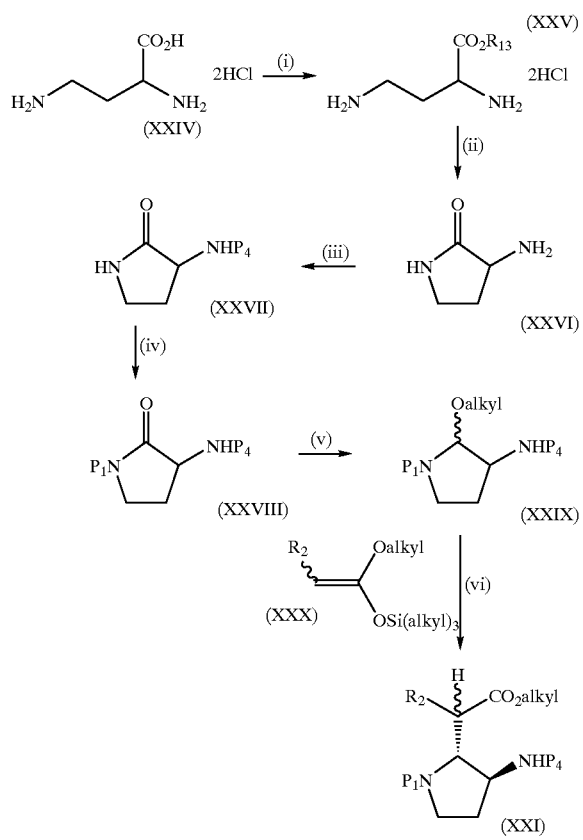

Scheme 2

Step (i)

The reaction will proceed under standard conditions for forming alkyl esters, for example by treatment with an alcohol eg methanol in the presence of $SOCl_2$.

Step (ii)

The cyclisation reaction will take place on stirring in water with Dowex 2×8 (preferably 400 mesh).

Step (iii)

$P_4$ is a protecting group. The means for protecting amine groups will be well known to a person skilled in the art, however we prefer to use trifluoroacetate (TFA). The TFA protected amine is formed by treating the compound of formula (XXVI) with methyl trifluoroacetate in a polar protic solvent, eg MeOH.

Step (iv)

Suitable protecting groups $P_1$ include CBZ. In this case, the compound of formula (XXVII) may be treated with a strong base such as LHMDS or nBuLi in an inert solvent such as THF, followed by treatment with CBZ-Cl.

Step (v)

This conversion will take place on treating the compound of formula (XXVIII) with a reducing agent eg sodium borohydride, followed by treatment with concentrated sulphuric acid in the presence of an alkyl alcohol e.g. ethanol solvent.

Step (vi)

The reaction of compounds of formula (XXIX) and (XXX) takes place in the presence of a Lewis acid e.g. boron trifluoride dietherate and an inert solvent e.g. dichloromethane. The group "alkyl" in Oalkyl and OSi(alkyl)$_3$ generally represents $C_{1-6}$alkyl. In the compound of formula (XXX), suitable alkyl groups in the silyl alkyl moiety include methyl, isopropyl and t-butyl. Preferred Oalkyl is OEt and preferred OSi(alkyl)$_3$ is OSi(i-Pr)$_3$ or OSi(Me)$_2$(t-Bu). The use of variants of compounds of formula (XXX) in which Oalkyl is replaced by OSi(alkyl)$_3$ is also envisaged.

Compounds of formula (XXX) in which $R_2$ represents $C_{1-4}$ alkyl, $C_{2-4}$ alkenyl or $C_{1-3}$alkylthio may be prepared by treatment of the corresponding carboxylic acid ester ($R_2CH_2COOEt$ or another alkyl ester, which compunds are either known or may be prepared by known methods) with a strong base (eg LHMDS) followed by a trialkylsilylchloride (such as trimethylsilylchloride) or a trialkylsilyltriflate. Typically the reaction will be performed at low temperature (less than 0° C.) in an inert solvent (such as THF) in the presence of DMPU.

Compounds of formula (VII) wherein $X_a$ represents S may be prepared by reaction of a corresponding compound of formula (III) with a compound of formula $R_3SSR_3$ under standard conditions for nucleophilic displacement. Compounds of formula (VIII) wherein $X_a$ represents SO may be prepared by peracid oxidation of a corresponding compound wherein $X_a$ represents S.

Compounds of formula (VII) may also be prepared in an analogous manner.

Compounds of formula (IX), (X), (XI) and (XII) may be prepared from compounds of formula (II) following conventional methods known per se.

A further aspect of the invention relates specifically to the preparation of compounds of formula (I) in the form of single enantiomers, rather than in the form of a racemic mixture.

Suitably, intermediates in the synthetic scheme are prepared by homochiral synthesis, or by resolution of a racemic mixture.

In one example of this aspect of the invention, the (2R, 3S) enantiomer of the compound of formula (XX) is prepared. The procedure is shown in Scheme 3:

Scheme 3

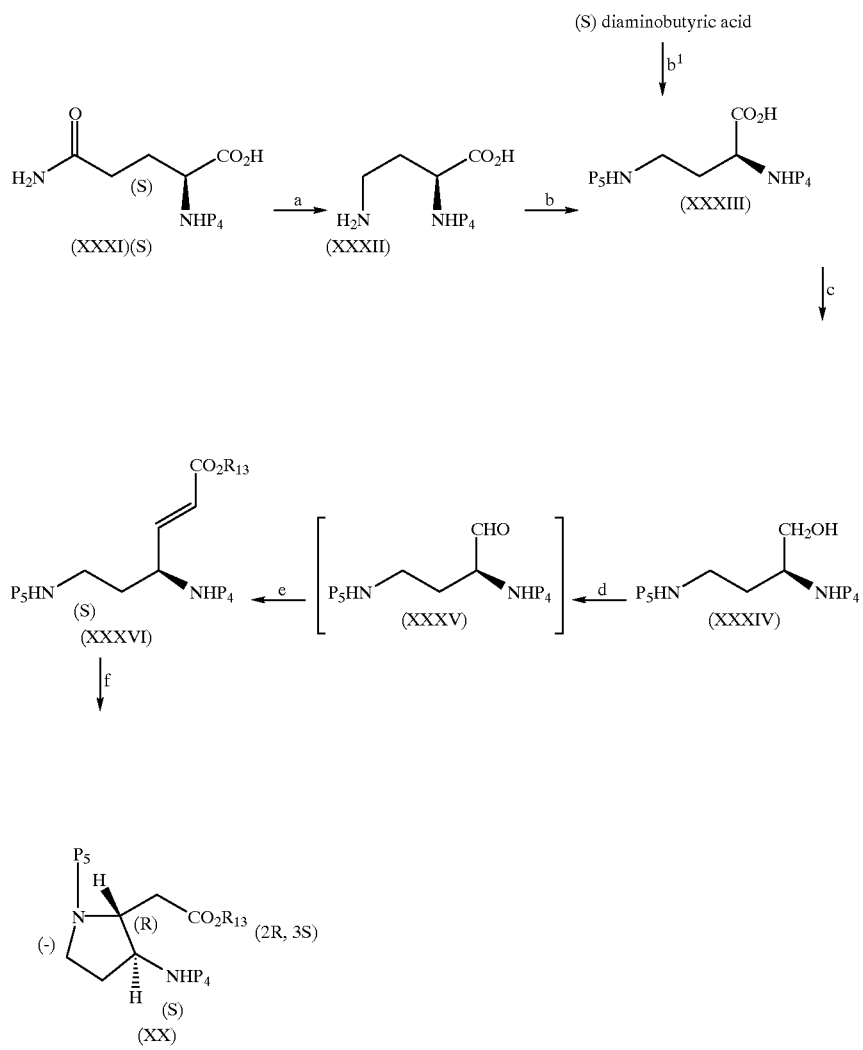

Step a

The compounds of formula (XXXI)(S) are either known compounds or may be prepared in analogous manner to known compounds. $P_4$ is a protecting group such as $P_3$ discussed above, and is suitably Boc. The reaction is suitably carried out using PIFA (phenyl iodosylbis(trifluoroacetate) and a base such as pyridine in an aqueous solvent, such as aqueous THF, dioxan or acetonitrile. This is the method of Stansfield, C.F. Organic Preparations and Procedures Int., 1990, 22(5), 593–603.

Step b $P_5$ is a protecting group eg CBZ. This protection reaction may be carried out in a conventional manner. For instance it is suitably carried out in a water miscible solvent such as THF, DMF or dioxan using N-(benzyloxycarbonyloxy) succinamide, benzyloxycarbonyl chloride, or any suitable source of the benzyloxycarbonyl group, with pH adjustment to alkaline with sodium carbonate.

As an alternative, step $b^1$, the compound of formula (XXXIII) can be prepared in conventional manner from (S) diaminobutyric acid.

Step c

This reaction is suitably carried out using in two stages. Firstly, reacting at reduced temperature with N-methylmorpholine and then an alkyl chloroformate such as ethyl chloroformate, in an organic solvent such as DCM, dioxan or THF. Secondly, the product is reduced, suitably with sodium borohydride at reduced temperature, such as −20° to 10° C., in a solvent such as THF.

Step d

This oxidation reaction may be suitably carried out in any suitable manner, for instance using oxalyl chloride in DMSO and methylene dichloride under nitrogen at reduced temperature, such as −30° to −70° C., followed by triethylamine. The intermediate (XXXV) suitably is not isolated.

Step e

This reaction is suitably carried out using a Wittig reagent such as a triphenylphosphorane $R_{13}O_2CCH=PPh_3$, or may also be carried out using a phosphonate in a Wadsworth-Emmons reaction.

Step f

This Michael addition reaction is suitably carried out using lithium bis(trimethylsilylamide) or other suitable strong base in a suitable organic solvent such as THF, ether or toluene, and preferably a complexing agent such as tetramethylethylenediamine is also present.

In another example of this aspect of the invention, the (2S, 3R) enantiomer of the compound of formula (XX) is prepared. The procedure is shown in Scheme 4.

Scheme 4

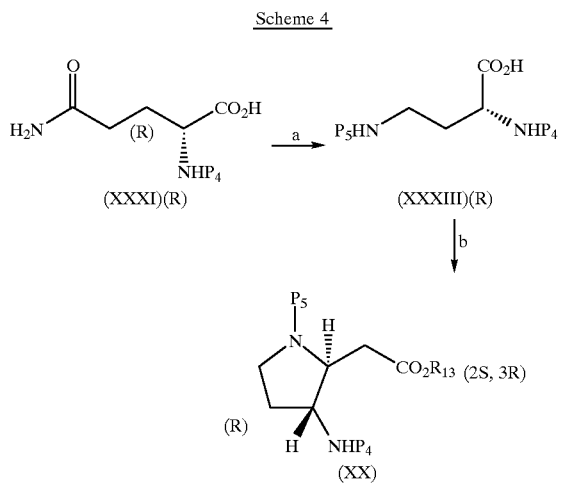

Step a

This reaction is suitably carried out using benzyl alcohol, PIFA and triethylamine at raised temperature in a suitable solvent such as DMF. This is analogous methodology to that outlined by Moutevelis-Minakakis and Photaki, J. Chem. Soc., Perkin Trans 1, 1985, 2277.

Compounds of formula (XXXI) (R) are known or analogous to known compounds (Zaoral, Collect. Czech. Chem. Commun, 1979, 44(4), 1179–86).

Step b

This is carried out in analogous manner to that described above for Scheme 3 steps c, d, e and f.

In yet a further example of this aspect of the invention, a compound of formula (XX) is resolved. This is suitably achieved by converting such a compound to the corresponding amine $(XX)^1$.

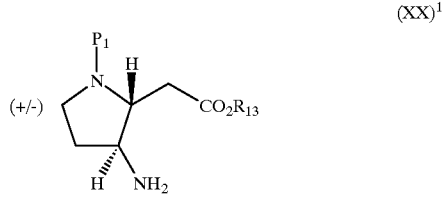

Suitably this conversion is achieved using any strong acid such as TFA, in a suitable solvent, such as DCM, and base wash.

The compound of formula $(XX)^1$ is then resolved. By way of illustration:

S-Series

Any suitable resolving agent, preferably (+) di-p-toluoyl-tartaric acid ((+) DPTTA) followed by recrystallisation suitably from ethanol, is used to give the S-series tartrate, of formula $(XX)^2$ (S):

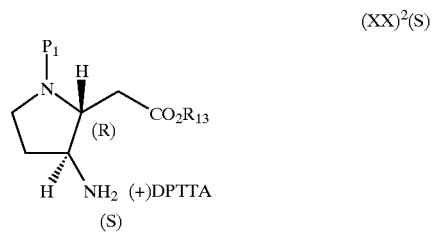

Typically two crystallisations are carried out.

R-Series

Any suitable resolving agent, preferably (−) di-p-toluoyl-tartaric acid ((−) DPTTA) followed by recrystallisation, suitably from ethanol, is used to give the R-series tartrate, of formula $(XX)^2$ (R):

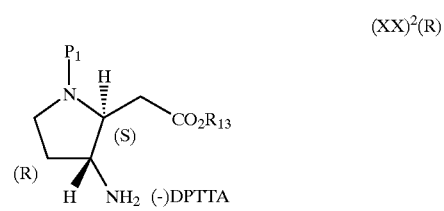

Again, typically two crystallisations are carried out. After this resolution step, the compounds of formula $(XX)^2$ (S) and $(XX)^2$ (R) can be reprotected to give the desired compounds of formula (XX) (S) and (XX) (R).

As an alternative to the above processes, intermediates can be resolved by column chromatography, for example using a chiral HPLC system. Suitably intermediates of formula (XXIII) are resolved in this way.

It will be further appreciated that the chemistry shown in Schemes 3 and 4 can be repeated using racemic compounds. For instance, Scheme 3 can be repeated using diaminobutyric acid as starting material. This is suitably used to provide another route to racemic intermediate $(XX)^1$, which can then be resolved as described above. Scheme 3 or 4 can also be used to make the other enantiomer.

An alternative homochiral synthesis of certain intermediate compounds of formula (XXIII) (notably compounds wherein $R_2$ represents alkyl, alkenyl or alkylthio) starting with D-asparagine is given in Scheme 5:

Scheme 5

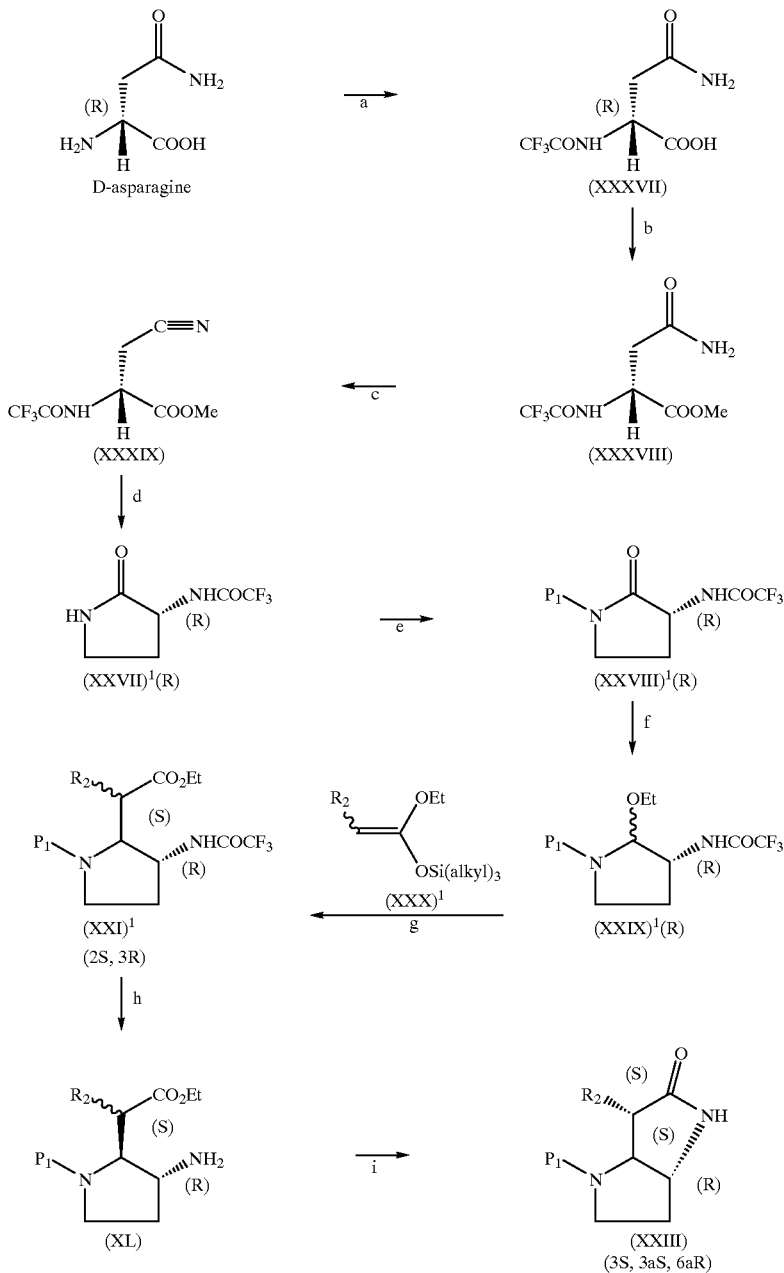

Step a
This reaction may be performed by treatment with methyltrifluoroacetate in a polar protic solvent such as methanol in the presence of a base such as triethylamine.

Step b
This reaction may be performed by treatment with acetyl choride and the appropriate alcohol such as methanol at low temperature (typically less than 0° C.).

Step c
This dehydration reaction may be performed by treating with tosyl chloride in the presence of pyridine in an inert solvent.

Step d
This reductive cyclisation reaction may be performed by stirring a solution of the compound of formula (XXXIX) in a polar protic solvent such as ethanol under an atmosphere of hydrogen gas in the presence of a suitable metallic catalyst such as 5% rhodium on alumina.

Steps e–g
These reactions follow the conditions described above for Scheme 2, steps (iv)–(vi).

Step h
This deprotection reaction will take place on treatment with base, such as potassium carbonate.

Step i
This ring closure reaction may be performed on treatment with t-butylmagnesium choride in an inert solvent such as THF in the presence of tetramethylethylenediamine or following the conditions of Scheme 1, step (x).

An alternative synthesis for compounds of formula (XXVIII)(R) based on (R)-methionine is given in Scheme 6.

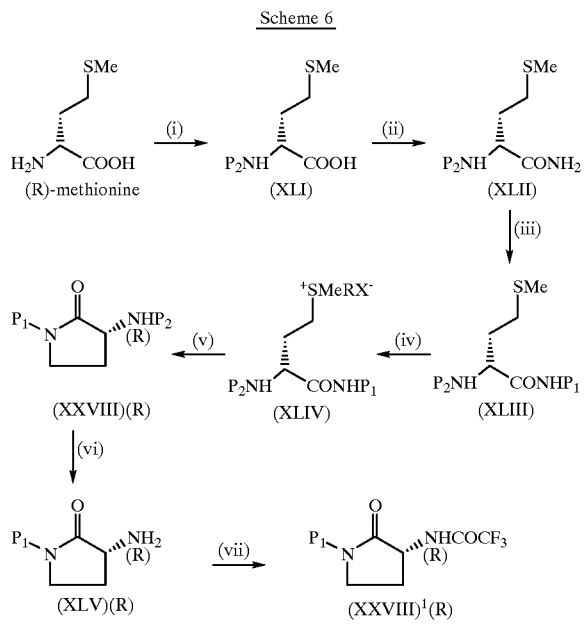

Scheme 6

Step (i)
This is a conventional protection reaction which, in the case when $P_2$ represents BOC, may be performed by reacting with $(BOC)_2O$ in the presence of base (e.g. NAOH) in a polar solvent such as dioxan/water.

Step (ii)
This conversion may be performed on treatment with ammonium bicarbonate in the presence of a suitable solvent such as pyridine/DMF and in the presence of $(BOC)_2O$ or suitable equivalent.

Step (iii)
This is a conventional protection reaction which, in the case when $P_1$ represents CBZ, may be performed by reaction with nBuLi followed by CBZ-Cl in the presence of an inert solvent such as THF below −50° C.

Step (iv)
This reaction may be performed by treatment with RX where RX is a compound capable of converting sulphur in the SMe moiety to sulphonium eg MeI, benzyliodide or $Me_2SO_4$ in a suitable solvent, e.g. propanone or acetonitrile. Generally R will represents alkyl or aralkyl and X will presents halide especially iodide or sulphate. Protection of the amide is convenient, although not essential, for this reaction.

Step (v)
This ring closure reaction may be performed by treatment with Dowex 2×8 400 mesh OH⁻ resin in a suitable solvent, e.g. MeCN. Alternatively, the ring closure may be performed by treatment with potassium carbonate in a suitable solvent e.g. MeCN.

Step (vi)
Deprotection may be performed in a conventional manner, for example, a BOC protecting group may be removed by treatment with HCl, e.g. in dioxan.

Step (vii)
This reaction may be performed by treatment with a trifluoroacetic acid alkyl ester (e.g. the methyl ester) in the presence of a suitable base e.g. N-methylmorpholine.

It will be appreciated that the the reactions of Schemes 5 and 6 may be performed starting with (L)-asparagine and (S)-methionine respectively to provide the enantiomers of the compounds set out in the Schemes. Alternatively they may be performed using racemic starting materials in which case a chiral resolution step will be necessary.

If compounds of formula (XLV) in racemic form are prepared following Scheme 6 from racemic methionine, we have found that the isomers of the compounds of formula (XLV) may be resolved by a dynamic resolution procedure. Thus a racemic compound of formula (XLV) may be treated with homochiral di-p-toluoyl tartaric acid in the presence of 3,5-dichloro-2-hydroxybenzaldehyde as catalyst in an inert solvent, e.g. THF. A homochiral salt of the compound of formula (XLV) results. A compound of formula (XXVIII)¹ may then be produced by subsequent treatment with trifluoroacetic acid methyl ester in the presence of N-methylmorpholine.

A further alternative synthesis of compounds of formula XXIII from Scheme 1 in homochiral form in which $R_2$ represents isopropyl is described in Scheme 7:

Scheme 7

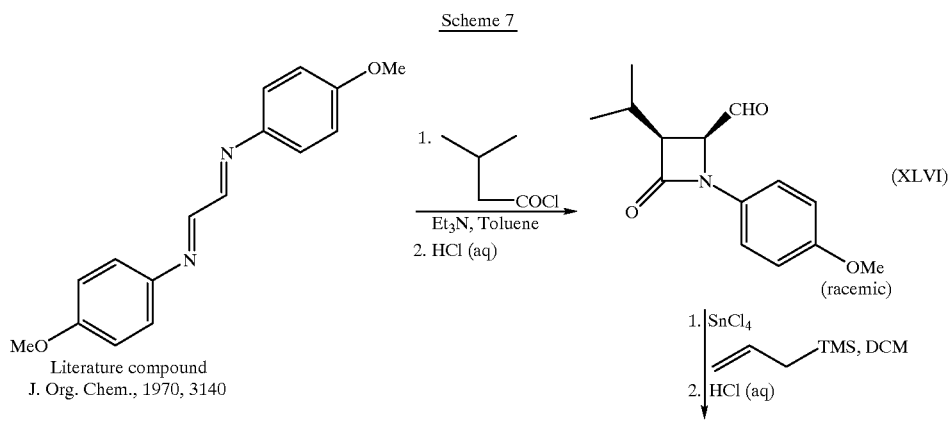

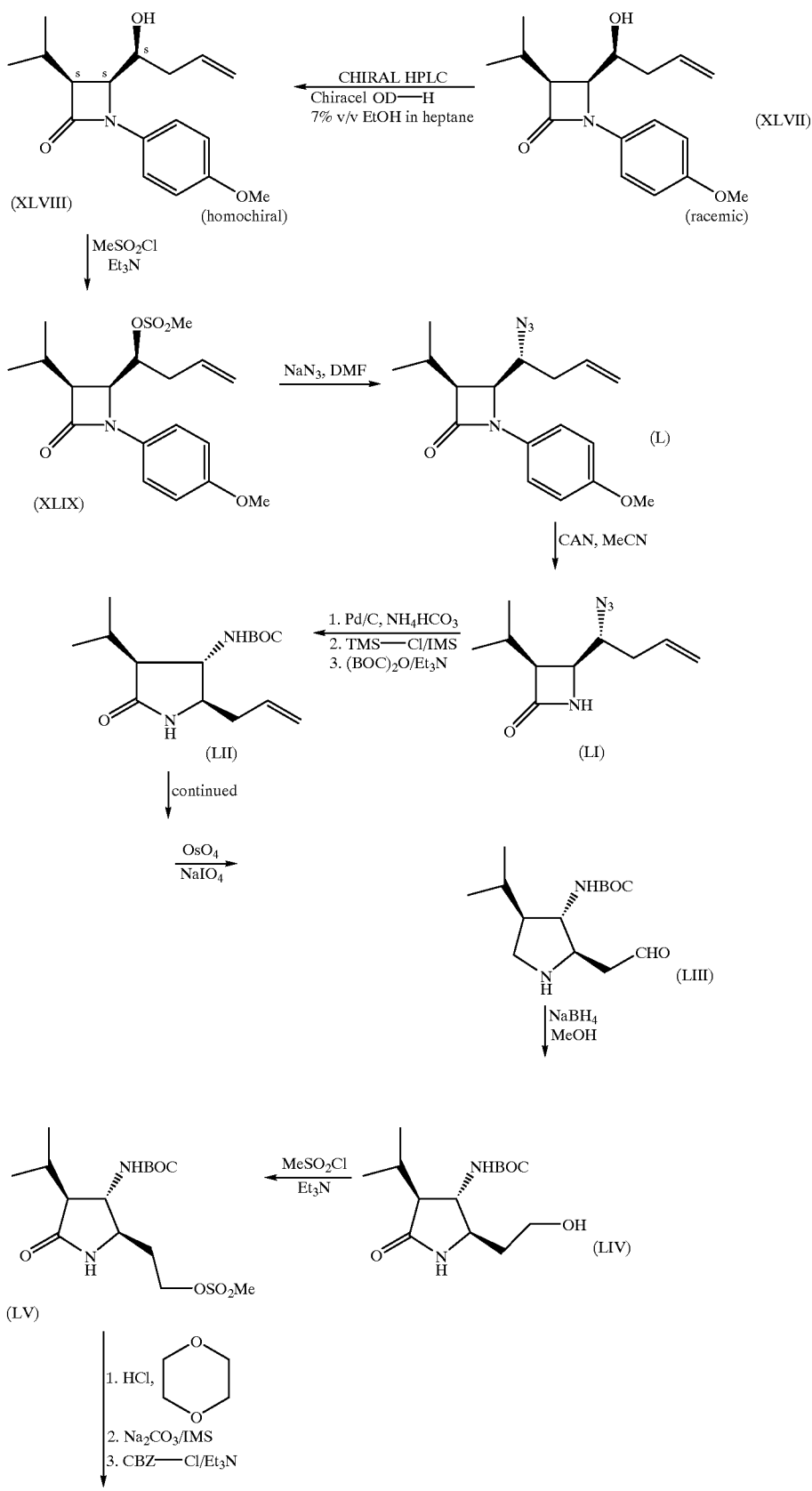

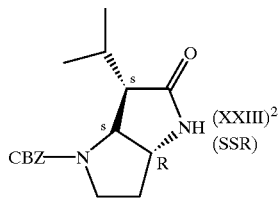
It will be apparent that the (RRS) enantiomer of (XXIII)[1] may also be prepared following isolation of the opposite enantiomer from the chiral HPLC in the third step.
The compound of formula (LIV) in Scheme 7 may alternatively be prepared following Scheme 8:
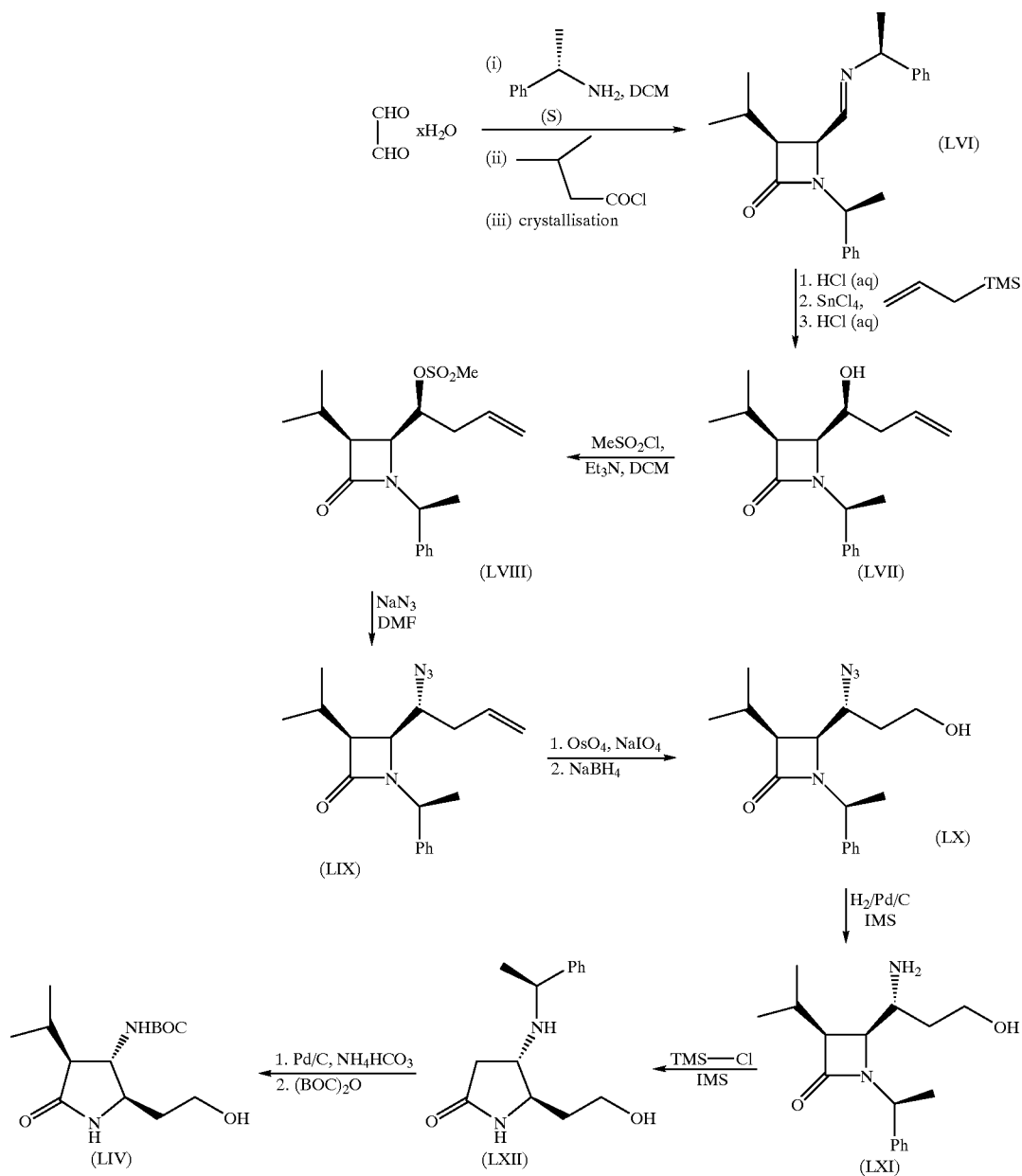

It will be appreciated that the method of Scheme 8 may also be adapted to prepare compounds of opposite chirality.

It will be apparent to a person skilled in the art that the above synthetic processes for the preparation of compounds of formula I may be modified so as to omit protecting groups or so as to use alternative protecting groups (for example those described in T W Greene "Protective Groups Inorganic Synthesis", 2nd Ed (1991) J Wiley & Sons) in the course of routine optimisation of experimental conditions.

Many of the intermediate compounds herein described are novel and form an important aspect of the invention. Accordingly, we provide according to a further aspect of the invention new compounds of formula (II) (including (II)$^1$), (III), (IV), (V), (VI), (VII), (VIII), (IX), (X), (XI), (XII), (XVI), (XVII), (XVIII), (XIX), (XX) (including (XX)$^1$) and (XX)$^2$), (XXI) (including (XXI)$^1$), (XXII), (XXIIa), (XXIII) (including (XXIII)$^1$), (XXIIIa), (XXVII) (including (XXVII)$^1$), (XXVIII) (including (XXVIII)$^1$), (XXIX) (including (XXIX)$^1$), (XXX), (XXXIV)–(XL), (XLII)–(XLIV) and (XLVI)–(LXII) and their deprotected derivatives and derivatives in which one or more nitrogen atoms is protected and/or a carboxylic acid is protected as a $C_{1-6}$alkyl ester (especially the ethyl ester). Preferred protecting groups include CBZ, BOC and trifluoroacetyl. Generally we prefer to protect the pyrrolidine or pyrrolidinone ring nitrogen with CBZ. We also provide intermediates in salt form as desired. We provide intermediates as racemic mixtures or in the form of a purified single enantiomer.

Novel chiral intermediates in the above described chiral and resolution sections also form an important aspect of this invention.

Processes for preparation of intermediates are also provided as an aspect of this invention.

Intermediates of formula II, III, V, XX, XXII, XXIIa, XXIII, XXIIIa, XXVIII and XXIX and their deprotected derivatives and derivatives in which one or more nitrogen atoms is protected and/or a carboxylic acid is protected as a $C_{1-6}$alkyl ester are of particular interest, especially when in the form of a purified single enantiomer.

The following non-limiting examples illustrate the present invention.

ABBREVIATIONS

| | |
|---|---|
| BOC | t-butyloxycarbonyl |
| CBZ | Benzyloxycarbonyl |
| DCM | Dichloromethane |
| (BOC)$_2$0 | Di-tert-butyldicarbonate |
| Et$_3$N | Triethylamine |
| Py-Ts | Pyridinium p-toluenesulfonate |
| PPh$_3$ | Triphenylphosphine |
| DEAD | Diethylazodicarboxylate |
| THF | Tetrahydrofuran |
| TFA | Trifluoroacetic Acid |
| NaH | Sodium hydride |
| LHMDS | Lithium bis (trimethylsilyl)amide |
| DMPU | 1,3-dimethyl-3,4,5,6-tetrahydro 2 (1H)-pyrimidinone |
| DMAP | 4-dimethylaminopyridine |
| NBS | N-bromosuccinimide |
| AIBN | Azoisobutyronitrile |
| DMF | Dimethylformamide |
| EDC | 1-(3-N,N-dimethylaminopropyl)-3-ethylcarbodiimide |
| CAN | Ceric ammonium nitrate |

Preparation of Intermediates

Intermediate 1
(4,4-Diethoxy-butyl)-carbamic acid benzyl ester

Three portions of benzyl chloroformate (260 ml) in dichloromethane (170 ml) were added sequentially over 1 h 40 min to a vigorously stirred mixture of 4-aminobutyraldehyde diethyl acetal (910 ml) in dichloromethane (3 l) and aqueous sodium carbonate (1M, 3 l). Stirring was continued for 50 min until gas evolution ceased. N-(2-aminoethyl)piperazine (40 ml) was added and stirring was continued for 1 h 15 min. The layers were separated and the organic layer was washed with aqueous citric acid (1M, 3.8 l) and saturated aqueous sodium bicarbonate (2 l), dried (MgSO$_4$), filtered and concentrated in vacuo to give the title compound as a yellow oil (1.6 kg). T.l.c. (Ether) Rf 0.5.

Intermediate 2
Benzyloxycarbonyl-(4,4-diethoxy-butyl)carbamic acid tert-butyl ester A solution of di-tert-butyldicarbonate (138 ml), in ethyl acetate (150 ml) was added dropwise to a stirred mixture of Intermediate 1 (84 ml), triethylamine (42 ml), and 4-dimethylaminopyridine (37 g) in ethyl acetate (150 ml). Stirring under nitrogen, at room temperature, was continued for 19 h. The reaction mixture was cooled with an ice bath and quenched with dilute hydrochloric acid (2M, 250 ml) added dropwise, maintaining the internal temperature below 25° C. The layers were separated and the organic layer was washed with dilute hydrochloric acid (1M, 200 ml) and water (200 ml), dried (MgSO$_4$), filtered and concentrated in vacuo to give the title compound as an orange oil (144.81 g). T.l.c. (1:1 Ether:Hexane) Rf 0.45.

Intermediate 3
Benzyloxycarbonyl-(3-formyl-propyl)-carbamic acid tert-butyl ester Pyridinium p-toluenesulphonate (7.5 g) was added to a stirred solution of Intermediate 2 (144.78 g) in an acetone (400 ml)/water (100 ml) mixture. The resulting mixture was warmed to 50° C. and stirring was continued for 5.5 h. The acetone was removed in vacuo and the aqueous residue treated with ether (1 l). The layers were separated and the organic layer was washed with water (200 ml), dried (MgSO$_4$), filtered and concentrated in vacuo to give the title compound as an orange oil (110 g). T.l.c. (1:1 Ether:Hexane) Rf 0.3.

Intermediate 4
6-Benzyloxycarbonyl-tert-butoxycarbonyl-amino)-4-hydroxy-hex-2-enoicacid methyl ester A solution of Intermediate 3 (520 g) in dry acetonitrile (1 l) was added dropwise to a stirred solution of 2-phenylsulfinyl acetate (267.5 g) and piperidine (160 ml) in dry acetonitrile (2 l) under nitrogen. Stirring under nitrogen at room temperature was continued for 15 h and then the mixture concentrated in vacuo to give a brown oil. The oil was partitioned between ethyl acetate (3 l) and dilute hydrochloric acid (1N, 2×1.5 l) and the organic layer washed with water (1 l) and saturated brine (500 ml), dried (MgSO$_4$) and concentrated in vacuo to give a brown oil (889.4 g). This was purified by column chromatography on silica gel using hexane:isopropyl acetate 9:1 to 1:1 as eluents to give the title compound as a yellow oil (273.5 g). T.l.c. (1:1 Ethyl acetate:Hexane) Rf 0.41.

Intermediate 5
6-(Benzyloxycarbonyl-tert-butoxycarbonyl-amino)-4-(1,3-dioxo-1,3-dihydroisoindol-2-yl)-hex-2E-enoic acid methyl ester A solution of diethylazodicarboxylate (105 ml) in dry tetrahydrofuran (95 ml) was added dropwise (2 h) to a stirred mixture of triphenylphosphine (173 g), phthalimide (97 g) and Intermediate 4 (254.7 g) in dry tetrahydrofuran (1.1 L) under nitrogen at 4–6° C. Stirring at 4° C. was continued for 2 h, then the mixture was allowed to warm to room temperature (4 h) and left to stand overnight under nitrogen. The mixture was concentrated in vacuo and the residue was triturated with t-butylmethylether (1 L) and cooled in an iced-water bath (5° C.). The precipitated triphenylphosphine oxide was filtered off, washed with ice cold t-butylmethylether (2×200 ml) and discarded. The filtrate was concentrated in vacuo to give an orange oil (428.06 g) which was purified by column chromatography on silica gel (Merck 9385; 9 kg; 28×32.5 cm) with hexane:ethyl acetate (2:1) as eluent to give an off-white solid in a viscous yellow oil (281.63 g). This was triturated with an ethyl acetate/hexane (1:1) mixture (1.2 L) and the solid was filtered off and discarded. The filtrate was concentrated in vacuo to give the title compound as a viscous yellow oil (270.2 g). T.l.c. [Ethyl Acetate:Hexane (1:2)], Rf 0.29.

Intermediate 6
6-Benzyloxycarbonylamino-4-(1,3-dioxo-1,3-dihydro-isoindol-2-yl)-hex-2E-enoic acid methyl ester Trifluoroacetic acid (148 ml, 1.92M) was added dropwise (10 min) to a stirred solution of Intermediate 5 (251.5 g) in dry dichloromethane (2.6 L) at 5° C. under nitrogen. Stirring was continued for 2 h when t.l.c. indicated complete reaction. The mixture was quenched by a slow addition (ca. 20 min) of aqueous sodium carbonate (1M, 750 ml) and stirring was continued until bubbling ceased. The layers were separated and the organic layer was washed with saturated aqueous sodium bicarbonate (750 ml) and brine (500 ml), dried ($MgSO_4$), filtered and concentrated in vacuo to give the title compound as a viscous yellow gum (204.3 g). T.l.c. [Ethyl acetate: Hexane (2:3)], Rf 0.24.

Intermediate 7
trans-3-(1,3-Dioxo-1,3-dihydro-isoindol-2-yl)-2-methoxycarbonylmethylpyrrolidine-1-carboxylic acid benzyl ester Sodium hydride (4.3 g of 60% in mineral oil) was added to a stirred, cold (4° C.) solution of Intermediate 6 (182.5 g) in dry tetrahydrofuran (2.8 L) under nitrogen. T.l.c. after 1 h indicates predominantly starting material so more sodium hydride (4.3 g of 60%, 107.5 mmol) was added and stirring under nitrogen at 4° C. was continued for 2 h. Still no reaction by t.l.c. so the mixture was allowed to warm to 10° C. (30 min) and stirring was continued for 1 h. T.l.c. indicates some reaction so more sodium hydride (2.15 g of 60%) was added and stirring was continued for a further 1 h at 10° C. whereupon t.l.c. indicates complete reaction. The reaction was quenched by adding aqueous brine (2:3, 1.6 L), initially dropwise until bubbling/gas evolution ceased then rapidly. The layers were separated and the aqueous layer was extracted with ethyl acetate (2×1 L). The organic solutions were combined, washed with saturated brine (1 L), dried ($MgSO_4$, overnight), filtered and concentrated in vacuo, to give the title compound as a viscous yellow oil (159.91 g). T.l.c. [Ethyl Acetate:Hexane (2:3)), Rf 0.26.

Intermediate 8
trans-3-Amino-2-methoxycarbonylmethyl-pyrrolidine-1-carboxylic acid benzyl ester Hydrazine hydrate (22 ml of 55%) was added to a stirred solution of Intermediate 7 (150.2 g) in ethanol (700 ml) under nitrogen. The resulting mixture was stirred and heated under reflux under nitrogen for 3 h and allowed to cool overnight. The insoluble solid was filtered off, washed with ethanol (160 ml) and discarded. The filtrate was concentrated in vacuo and the residue partitioned between ethyl acetate (800 ml) and dilute hydrochloric acid (1M, 500 ml) filtering off some solid which was washed with dilute hydrochloric acid (1M, 300 ml) before being discarded. The aqueous wash was used to re-extract the ethyl acetate solution.

The aqueous acidic extracts were combined, washed with ethyl acetate (400 ml), neutralised to ca. pH8 with aqueous sodium hydroxide (2M, 350 ml) and aqueous sodium carbonate (1M, 100 ml) then extracted with ethyl acetate (4×500 ml). These extracts were combined, washed with saturated brine (300 ml), dried ($MgSO_4$, overnight), filtered and concentrated in vacuo to give the title compound as a yellow oil (62.5 g). T.l.c. [Ethyl acetate:methanol (9:1)], Rf streak 0.25 to 0.09.

Intermediate 9
trans-3-tert-Butoxycarbonylamino-2-methoxycarbonylmethyl-pyrrolidine-1-carboxylic acid benzyl ester A solution of di-t-butyl dicarbonate (69 g) in dry acetonitrile (500 ml) was added dropwise (30 min) to a stirred solution of Intermediate 8 (80.77 g) and triethylamine (44 ml) in dry acetonitrile (950 ml) under nitrogen. Stirring at room temperature was continued for 5.5 h then the mixture was left to stand overnight at room temperature under nitrogen. The mixture was concentrated in vacuo and the residue (141.7 g) partitioned between dilute hydrochloric acid (1M, 650 ml) and ethyl acetate (1.3 L). The aqueous layer was re-extracted with ethyl acetate (650 ml). The organic extracts were combined, washed with saturated brine (500 ml), dried ($MgSO_4$), filtered and concentrated in vacuo to give a red-brown oil (120.5 g). The oil was purified by filter column chromatography on silica gel (Merck 9385, 1.2 kg, 11×18 cm) with hexane:ethyl acetate (2:1) as eluent to give the title compound as a pale yellow oil (98.23 g) which crystallised on standing to an off-white solid (90.85 g). This was triturated with an ether:hexane (1:4) mixture (250 ml) to give the title compound as a white solid (81.16 g) with m.p. 73–74° C. T.l.c. [Ethyl Acetate:Hexane (1:2)], Rf 0.21.

Intermediate 10
rel-(2R,3S)-3-tert-Butoxycarbonylamino-2-(R-methoxycarbonyl-but-3-enyl)-pyrrolidine-1-carboxylic acid benzyl ester A solution of lithium bis(trimethylsilyl)amide in tetrahydrofuran (1M, 80 ml) was added dropwise (65 min) to a stirred solution of Intermediate 9 (9.81 g) in a dry tetrahydrofuran (54 ml)/1,3-dimethyl-3,4,5,6-tetrahydro 2-(1H)-pyrimidinone (120 ml) mixture at −71±1° C. (internal) under nitrogen. After stirring for 1 h at below −70° C. allyl iodide (2.8 ml) was added at −71±1° C. (5 min) and the resulting mixture stirred at below −70° C. for 2 h. The reaction was quenched by the dropwise addition of saturated aqueous ammonium chloride (20 ml) and the mixture was allowed to warm to 0° C., more aqueous ammonium chloride (20 ml) was added and the resulting mixture was extracted with ethyl acetate (4×100 ml). The organic extracts were combined and concentrated in vacuo to give a yellow oil which was partitioned between toluene (200 ml) and water (100 ml). The organic phase was washed with water (2×80 ml) and saturated brine (80 ml), dried ($Na_2SO_4$), filtered and concentrated in vacuo to give an orange oil (15.96 g). This was purified by flash column chromatography on silica gel (Merck 9385, 700 g, 13×14 cm) with hexane:ethyl acetate (7:3) as eluent to give the title compound as a colourless oil (7.7 g). T.l.c. [Ethyl acetate:hexane (3:7)], Rf 0.24.

Intermediate 11
rel-(2R,3S)-3-tert-Butoxycarbonylamino-2-(1R-carboxy-but-3-enyl)-pyrrolidine-1-carboxylic acid benzyl ester A solution of potassium hydroxide (45 g) in water (400 ml) was added to a stirred solution of Intermediate 10 (32.17 g) in ethanol (400 ml). The resulting mixture was stirred at 55° C. under nitrogen for 5 h. The ethanol was removed in vacuo and the resulting mixture acidified to ca. pH2 with dilute hydrochloric acid (2M, 400 ml). The mixture was extracted with ethyl acetate (3×500 ml), the extracts were combined, dried ($MgSO_4$), filtered and concentrated in vacuo to give the title compound as a colourless foam (29 g). T.l.c. [Ethyl acetate:hexane (3:7)], Rf streak 0.30 to 0.12.

Intermediate 12
rel-(2R,3S)-3-Amino-2-(1R-carboxy-but-3-enyl)-pyrrolidine-1-carboxylic acid benzyl ester hydrochloride Intermediate 11 (29 g) was dissolved in a solution of hydrogen chloride in dioxan (4M, 300 ml) and the mixture stirred at room temperature under nitrogen for 3 h. The solvent was removed in vacuo and the residue (25.56 g) triturated with ether (2×80 ml) to give the title compound as a white solid (22.03 g) with m.p. 158–159° C.

Intermediate 13
rel-(3aS,6R,6aR)-6-Allyl-5-oxo-hexahydro-pyrrolo[3,2-b]pyrrole-1-carboxylic acid benzyl ester 2-Chloro-1-methylpyridinium iodide (3 g) was added in one portion to a stirred solution of intermediate 12 (2.73 g) and N,N-diisopropylethylamine (1.3 ml) in dry dichloromethane (1.25 L) at room temperature under nitrogen. After 1 h more N,N-diisopropylethylamine (2.6 ml) was added, stirring was continued for 4 h, then the mixture was left to stand for 16 h. The solution was washed with dilute hydrochloric acid (0.1M, 2×75 ml) and water (75 ml), dried ($Na_2SO_4$), filtered and concentrated in vacuo in the presence of silica gel (5 g). The solid support was applied to a silica column (Merck 9385) which was eluted with an ethyl acetate:hexane (3:1) mixture to give a yellow solid which was triturated with ether (20 ml+10 ml) to give the title compound as a pale cream solid (1.664 g) with m.p. 159.5–160° C.

Intermediate 14
rel-(3R,3aR,6aS)-1-(Naphthalene-2-sulfonyl)-3-propyl-hexahydro-pyrrol[3,2-b]pyrrol-2-one A solution of Example 1 (1.45 g) in ethyl acetate (200 ml) was hydrogenated at one atmosphere and room temperature over palladium hydroxide (2.0 g) and 4 Å activated sieves (3.6 g). After 8 hours, the catalyst was filtered onto hyflo and washed with ethyl acetate (10 ml). The filtrate was concentrated in vacuo to give, after the addition and removal in vacuo of ether (10 ml), the title compound as a pale browm foam, (985 mg). T.l.c. (Methanol:ethyl acetate; 3:7) Rf 0.49.

Intermediate 15
Piperidin-1-yl-acetic acid hydrochloride

Ethyl-1-piperidine acetate (10 g) was dissolved in ethanol (40 ml). Sodium hydroxide (9.34 g) in water (30 ml) was added, and the resulting mixture stirred at room temperature for 18 h. T.l.c. $SiO_2$ (ether:triethylamine 100:1) indicated the complete disappearance of starting material, and the appearance of baseline material. The solvent was removed in vacuo, the residue dissolved in water (100 ml), and the mixture acidified to pH1 using concentrated hydrochloric acid (25 ml). The mixture was evaporated to dryness, and the residue washed with ethanol (500 ml). The ethanol extract was evaporated in vacuo to leave a white solid. This was dried in vacuo to give the title compound as a white solid (10.2 g), m.p.=214.2°–214.8° Lit. m.p.=215°–216° C. Assay Found C,44.9; H,7.6; N,7.5%. $C_7H_{13}NO_2$·HCl 0.5$H_2O$ requires C,44.8; H,8.0; N,7.4%.

Lit. ref. A. Domow & W. Sassenburg, Chem. Ber., 90, 14, 1957.

Intermediate 16
4-Piperidin-1-yl-butyric acid benzyl ester

4-Bromobutyrichloride (6 g) was dissolved in dichloromethane (30 ml), and cooled to 0° C. under nitrogen. A solution containing benzyl alcohol (3.4 ml) and triethylamine (4.5 ml) in dichloromethane (35 ml) was added dropwise over 30 min. The mixture was stirred under nitrogen for 2 h. T.l.c. (10:1 hexane:ether) showed the complete disappearance of benzyl alcohol, and the formation of a less polar product. Piperidine (3.2 ml) was added and the resulting mixture heated under reflux for 18 h. The cooled mixture was partitioned between 2M hydrochloric acid (250 ml) and ether (250 ml). The aqueous layer was separated, basified with solid potassium carbonate until pH≧10, extracted with ether (2×250 ml), dried ($MgSO_4$), and the solvent evaporated in vacuo to leave an orange oil. T.l.c. $SiO_2$, ether:triethylamine (100:1), Rf=0.34 detection, u.v., IPA.

Intermediate 17
4-Piperidin-1-yl-butyric acid

To palladium on charcoal (10%) (700 mg) under vacuum, was added absolute ethanol (30 ml), and the resulting suspension stirred under an atmosphere of hydrogen for 10 min. A solution of Intermediate 16 (3.8 g) in absolute ethanol (100 ml) was added, and the resulting mixture stirred under an atmosphere of hydrogen. After 1 h when 360 ml of hydrogen had been taken up, the mixture was filtered through hyflo, and the filter cake washed with ethanol (100 ml). The combined filtrate was evaporated in vacuo to leave a colourless gum. Trituration with acetone (50 ml) gave the title compound as a white crystalline solid (1.7 g), m.p.=68–70° C.

Intermediate 18
6Piperidin-1-yl-hexanoic acid benzyl ester

6-Bromohexanoyl chloride (6 g) was dissolved in dichloromethane (35 ml), and cooled to 0° C. under nitrogen. A mixture containing benzyl alcohol (3.04 g) and triethylamine (4.2 ml) in dichloromethane (25 ml) was added dropwise over 20 min, and the resulting mixture stirred for 2 h, allowing it to reach room temperature. Piperidine (2.8 ml) and triethylamine (4.2 ml) were added and the resulting mixture heated under reflux for 18 h. The cooled mixture was poured into 2M hydrochloric acid (200 ml), and washed with ether (2×200 ml). The aqueous phase was basified with solid potassium carbonate (ca. 10 g), extracted with ether (2×200 ml), dried ($MgSO_4$) and the solvent evaporated in vacuo to leave a pale yellow oil (4.5 g). Flash chromatography eluting with ether triethylamine gave the title compound as a pale yellow oil (3.2 g). T.l.c. $SiO_2$ ether:triethylamine (100:1) Rf=0.21, detection u.v., IPA.

Intermediate 19
6-Piperidin-1-yl-hexanoic acid

To palladium on charcoal 10% (800 mg) under vacuum, was added absolute ethanol (30 ml), and the resulting suspension under an atmosphere of hydrogen for 10 min. A solution of the Intermediate 18 (3.2 g) in absolute ethanol (80 ml) was added, and the resulting mixture stirred under an atmosphere of hydrogen for 1 h. The mixture was filtered through hyflo, the filter cake washed with ethanol (100 ml), and the filtrate evaporated in vacuo to leave a colourless gum. Trituration with acetone (40 ml) gave the title compound as a white solid, (800 mg), m.p=74°–76° C.

Intermediate 20

3-Dimethylsulfamolyl-benzenesulfonyl chloride

Benzene-1,3disulphonylchloride (3 g) was dissolved in dichloromethane (40 ml). Dimethylamine hydrochloride (447 mg) was added, followed by triethylamine (1.52 ml), and the resulting mixture stirred at room temperature overnight. The mixture was partitioned between water (100 ml), and ethyl acetate (100 ml), the organic phase was separated, dried (MgSO$_4$), and the solvent removed in vacuo to leave a yellow gum. Flash chromatography eluting with ether:hexane (1:1) gave the title compound as a white solid (903 mg). Analysis Found: C,34.1; H,3.7; N,4.85%. $C_8H_{10}NO_4S_2Cl$ requires C,33.9; H,3.55; N,4.9%.

Intermediate 21 rel-(2R,3S)-3-tert-Butoxycarbonylamino-2-(1R-methoxycarbonyl-propyl)-pyrrolidine-1-carboxylic acid benzyl ester A 1.0M solution of lithium hexamethyldisilylamide in tetrahydrofuran (1.6 ml) was added dropwise under nitrogen to a stirred solution of intermediate 9 (196 mg) in dry tetrahydrofuran (2 ml) and 1,3-dimethyltetrahydro-2(1H)-pyrimidinone (3.6 ml), cooled to −75° C. The mixture was stirred for one hour before ethyl iodide (50 ml) was added. Stirring was continued for a further two hours at −75° C. before saturated aqueous ammonium chloride solution (2 ml) was added to the mixture. After warming to room temperature, water (10 ml) was added and the mixture was extracted with ethyl acetate (3×15 ml). The combined extracts were dried (Na$_2$SO$_4$), filtered, the solvent evaporated in vacuo and the residue purified by flash chromatography on silica (Merck 9385) using ethyl acetate:n-hexane (3:7) as eluent to give the title compound (117 mg) as a colourless oil, T.l.c. (3:7 ethyl acetate:n-hexane) Rf 0.24.

Intermediate 22 rel-(2R,3S)-3-tert-Butoxycarbonylamino-2-(1R-carboxy-propyl)-pyrrolidine-1-carboxylic acid benzyl ester Prepared in a similar manner to Intermediate 11 from Intermediate 21 to give the title compound as a colourless foam. T.l.c. (4:6 ethyl acetate:n-hexane) Rf 0.2.

Intermediate 23 rel-(2R,3S)-3-Amino-2-(1R-carboxy-propyl)-pyrrolidine-1-carboxylic acid benzyl ester hydrochloride Prepared in a similar manner to Intermediate 12 from Intermediate 22 to give the title compound as a white solid. T.l.c. (n-Butanol:acetic acid:water; 4:1:1) Rf 0.53.

Intermediate 24 rel-(3aS,6R,6aR)-6-Ethyl-5-oxo-hexahydro-pyrrolo[3,2-b]pyrrole-1-carboxylic acid benzyl ester Prepared in a similar manner to Intermediate 13 from Intermediate 23 to give the title compound as a pale yellow solid. T.l.c. (ethyl acetate) Rf 0.4.

Intermediate 25 rel-(3R,3aR,6aS)-3-Ethyl-1-(naphthalene-2-sulfonyl)-hexahydro-pyrrolo[3,2-b]pyrrol-2-one Prepared in a similar manner to Intermediate 14 from Example 4 to give the title compound as a yellow glass. T.l.c. (1:4 methanol:ethyl acetate) Rf 0.31.

Intermediate 26 rel-(3R,3aR,6aS)-1-Methanesulfonyl-3-propyl-hexahydro-pyrrolo[3,2-b]pyrrol-2-one Example 6 (517 mg) was hydrogenated over 20% moist palladium hydroxide on carbon (60 mg) in ethyl acetate (50 ml) for 4 h. The catalyst was removed by filtration and the filtrate concentrated to give the title compound as a white solid (323 mg). T.l.c. (95:5; Dichloromethane:methanol) Rf 0.27.

Intermediate 27

3-Morpholin-4-yl-propane-1-sulfonyl chloride hydrochloride

Thionyl chloride (10 ml) was added to 4-morpholinepropane sulfonic acid (4.4 g) followed by dimethylformamide (0.2 ml). The mixture was heated at reflux under nitrogen for 5 h. The thionyl chloride was removed in vacuo and the residue triturated with acetonitrile and filtered to give a white solid. This was dried at 80° C. in vacuo to give the title compound as a white solid (2.7 g). Found: C,31.9; H,5.9; N,5.1. $C_7H_{14}ClNO_3S.HCl$ requires C,31.8; H,5.7; N,5.3%.

Intermediate 28

3-Piperidin-1-yl-propane-1-sulfonyl chloride hydrochloride

Thionyl chloride (12 ml) was added to 4-piperidinepropane sulfonic acid (3.2 g) and the mixture heated at reflux for 5 h. After standing at room temperature overnight the volatiles were removed in vacuo to give a white solid which turned yellow/green on standing at room temperature over 2 h. This material was used crude without further purification.

Intermediate 29

3-(4-Methyl-piperazin-1-yl)-propane-1-sulfonic acid

N-methyl piperizine (4.68 g) was dissolved in isopropanol (25 ml) and treated with 1,3-propanesultone (5.7 g) with cooling to maintain the temperature of the reaction below 50° C. The reaction mixture was allowed to stand at room temperature overnight, then diluted with ether and the white solid filtered. On standing, the white solid became a sticky semi-solid (7.1 g). Mass spec MH$^+$ (found)=223 MH$^+$ (calc)=223.

Intermediate 30

3-(4-Methyl-piperazin-1-yl)-propane-1-sulfonyl chloride dihydrochloride

Intermediate 29 (1.0 g) was suspended in thionyl chloride (20 ml) and dimethylformamide (0.1 ml) added. The mixture was heated at reflux for 6 h. The thionyl chloride was removed in vacuo and the residue triturated with dry acetonitrile and filtered to give the title compound as a white solid (610 mg). The product was used without further purification or characterization.

Intermediate 31

4-Morpholin-4-yl-butane-1-sulfonic acid

Morpholine (3.56 g) was dissolved in isopropanol (25 ml) and treated with 1,4-butane sultone (5.58 g) at 10° C. The reaction mixture was allowed to warm to room temperature and stirred for 3 days. The white precipitate that had formed was filtered and dried to give the title compound (1.64 g). Mass spec MH$^+$ (found) 224 MH$^+$ (calc) 224.

Intermediate 32

4-Morpholin-4-yl-butane-1-sulfonyl chloride hydrochloride

Intermediate 31 (1.02 g) was suspended in thionyl chloride (10 ml) and the mixture treated with dimethylformamide (0.1 ml). The mixture was heated at reflux for 5 h. The volatiles were removed in vacuo and the residue used without further purification.

Intermediate 33
rel-(3R, 3aR,6aS)-1-(Naphthalene-1-sulfonyl)-3-propyl-hexahydro-pyrrolo[3,2-b]pyrrol-2-one Example 15 (385 mg) was hydrogenated over 5% palladium on carbon (60 mg) for 3 h. More catalyst (60 mg) was added followed by conc. hydrochloric acid (2 drops) and the hydrogenation continued for 2 h. T.l.c. (ethyl acetate:methanol; 99:1) indicated incomplete reaction. The catalyst was removed by filtration and the filtrate concentrated to give a pale yellow gum. This was hydrogenated over 20% palladium hydroxide (90 mg) in ethanol (30 ml) and ethyl acetate (25 ml) for 20 h. The catalyst was removed by filtration, the filtrate concentrated and the residue chromatographed on silica (eluting with ethyl acetate and then 5% methanol/ethyl acetate) to give the title compound as a white foam (100 mg). T.l.c. $SiO_2$ (ethyl acetate:methanol) Rf 0.15.

Intermediate 34
rel-(3R,3aR,6aS)-3-Propyl-hexahydro-pyrrolo[3,2-b]pyrrol-2-one Intermediate 13 (0.305 g) in tetrahydrofuran (15 ml) was added to a prehydrogenated suspension of 5% palladium on carbon (0.235 g) in tetrahydrofuran (5 ml), and the mixture stirred under a $H_2$ atmosphere for 2.25 h. The solution was filtered through hyflo and then concentrated in vacuo to give the title compound as a white solid (104 mg) m.p. 97–100° C. T.l.c. (7:3 ethyl acetate:hexane) Rf 0.17 streak.

Intermediate 35
rel-3R,3aR,6aS)-4-Phenylmethanesulfonyl-3-propyl-hexahydro-pyrrolo[3,2-b]pyrrol-2-one α-Toluenesulphonylchloride (0.168 g) was added to a solution of Intermediate 34 (0.099 g) in dichloromethane under nitrogen. After stirring for 0.5 h at room temperature, triethylamine (0.164 ml) was added and the resultant mixture stirred for a further 18 h. Water (20 ml) was added and the mixture extracted with ethyl acetate (2×15 ml). The combined extracts were washed with 1M hydrochloric acid (20 ml), dried ($MgSO_4$) and concentrated in vacuo. The residue was purified by flash chromatography on silica (Merck 9385) using ethyl acetate:hexane (3:1) as eluent to give the title compound as a white solid (0.090 g). T.l.c. (ethyl acetate) Rf 0.45.

Intermediate 36
5-m-Tolyl-1H-tetrazole

Tributyltinazide (3.6 g) and 3-methylbenzonitrile (0.7 g) were heated at 160° C. for 2.5 h. The mixture was cooled and partitioned between 2N sodium hydroxide solution. (80 ml), water (30 ml) and diethyl ether (50 ml). The ether layer was removed and the aqueous was washed with diethyl ether (3×30 ml). The aqueous phase was acidified with concentrated hydrochloric acid and extracted with ethyl acetate (3×30 ml). The dried ($MgSO_4$) organic extracts were concentrated in vacuo to give the title compound as a white solid (0.933 g). M.p. 150–152° C.

Intermediate 37
5-m-Tolyl-2-trityl-2H-tetrazole

Intermediate 36 (12.7 g), triethylamine (16.6 ml), 4-dimethylaminopyridine (0.25 g) and trityl chloride (22.1 g) were dissolved in dry dichloromethane (130 ml) and stirred at room temperature under $N_2$ for 48 h. The mixture was filtered and diluted with dichloromethane (100 ml). The solution was washed with 2M sodium hydroxide (2×150 ml) and saturated copper sulphate solution (100 ml). The resultant precipitate was removed by filtration. The filtrate was washed with brine (100 ml), dried ($MgSO_4$) and concentrated in vacuo to give the title compound as a pale brown solid (26.0 g). T.l.c. Silica [Hex./$Et_2O$ (4:1)] Rf 0.5.

Intermediate 38
5-(3-Bromomethyl-phenyl)-2-trityl-2H-tetrazole

A mixture of Intermediate 37 (2.0 g), N-bromosuccinimide (1.1 g) and azoisobutyronitrile (87 mg) in dry carbon tetrachloride (25 ml) was heated at reflux for 3 h. The mixture was cooled, diluted with dichloromethane (100 ml) and the succinimide removed by filtration. The organic layer was washed with water (2×100 ml), dried ($MgSO_4$) and concentrated in vacuo to give the title compound as an off-white foam (2.6 g). T.l.c. Silica (Hex./$Et_2O$ (4:1)] Rf 0.44.

Intermediate 39
5-(3-Chloromethyl-phenyl)-2-trityl-2H-tetrazole

Intermediate 38 (7.3 g) and lithium chloride (9.6 g) in dry dimethylformamide (300 ml) was stirred at room temperature for 24 h. The solution was poured into 10% lithium chloride solution (250 ml) and ethyl acetate (300 ml) was added. The aqueous layer was extracted with ethyl acetate (2×150 ml) and the combined organics were dried ($MgSO_4$). The solvent was removed in vacuo to give the title compound as a white solid (6.6 g). T.l.c. Silica [Hex./$Et_2O$ (4:1)] Rf 0.44.

Intermediate 40
5-(3-Chloromethyl-phenyl)-1H-tetrazole

Intermediate 39 (6.5 g) in a mixture of ethanol (300 ml), dichloromethane (50 ml) and concentrated hydrochloric acid (7 ml) was stirred at room temperature for 4 h. The resultant solution was concentrated in vacuo and water (20 ml) added. The mixture was partitioned between ether (200 ml) and 2N sodium carbonate solution. The aqueous layer was washed with ether (2×250 ml), acidified with concentrated hydrochloric acid and then extracted with ethyl acetate (3×200 ml). The combined extracts were dried ($MgSO_4$) and the solvent removed in vacuo to give the title compound as a pink solid (2.1 g). M.p. 152–154.5° C.

Intermediate 41
Thiosulfuric acid S-[3-(1H-tetrazol-5-yl-benzyl] ester sodium salt Sodium thiosulphate (1.3 g) in water (10 ml) was added to Intermediate 40 (1.1 g) in methanol (5 ml) and ethanol (4 ml). The suspension was heated at reflux for 20 h. The cooled solution was concentrated in vacuo and the residue triturated with ether/ethyl acetate (ca. 3:1) to give the title compound as a white solid (1.3 g). M.p.>250° C.

Intermediate 42
[3-(1H-Tetrazol-5-yl)-phenyl]-methanesulfonyl chloride

A suspension of Intermediate 41 (1.3 g) in ice/water (20 ml)/acetic acid (4 ml) was chilled below 10° C. Chlorine was rapidly passed into the stirred mixture, maintaining the temperature below 10° C., over 40 minutes. Ethyl acetate (200 ml) and water (200 ml) were added. The aqueous layer was extracted with ethyl acetate (2×100 ml). The combined organics were washed with 5% sodium metabisulphite solution (2×100 ml) and dried ($MgSO_4$). The solvent was removed in vacuo to give the title compound as a white solid (0.6 g). Mass spec: $MNH_4^+$ (calc.) 276 $MNH_4^+$ (obs) 276.

Intermediate 43
Benzo[b]thiophene-3-sulfonic acid potassium salt

Concentrated sulphuric acid (0.43 ml) was added to a cooled, stirred mixture of benzothiophene (1 g) in acetic anhydride (0.93 ml), giving a brown viscous oil, which was left to stir for 50 mins under nitrogen. The mixture was then diluted with ice to give 20 ml, extracted with ether (2×10 ml) and the aqueous phase concentrated in vacuo to give 5 ml. This was then treated with a hot saturated solution of potassium chloride (2 g), cooled and filtered to give the title compound as a pale brown solid (3.935 g).

$^1$H NMR (δDMSO) 7.34–7.42 (2H, m), 7.78 (1H, s), 7.95 (1H, dd), 8.19 (1H, dd).

Intermediate 44
Benzo[b]thiophene-3-sulfonyl chloride

Intermediate 43 (1 g) was finely powdered and mixed with powdered phosphrous pentachloride (1.2 g) and the mixture allowed to stir for 24 hours. A semisolid reaction mixture was formed. This was diluted with ice and extracted with ether (3×50 ml). The combined organic phase was washed with brine (50 ml), dried (MgSO$_4$), and the solvent evaporated in vacuo to give a yellow solid. This was chromatographed over flash silica eluting with 37% ethyl acetate/hexane to give the title compound[1] as a yellow solid (0.341 g). T.l.c. SiO$_2$ (1:1) hexane:ether Rf=0.44 detection KMnO$_4$.

Ref. 1: N. B. Chapman, C. G. Hughes, R. M. Scrowston; J. Chem. Soc. C, 2431, 1970.

Intermediate 45
Benzo[b]thiophene-2-sulfinic acid lithium salt

A mixture of n-butyllithium (1.6M in hexane; 9.3 ml) and ether (5 ml) was added dropwise during 5 minutes to a stirred solution of benzothiophene (2 g) in ether (25 ml) at 0° C., and the resulting mixture was stirred at 0° C. for 1 hour under nitrogen. This solution was gradually added through a cannula under nitrogen to a vigorously stirred solution of sulphurdioxide (50 ml) in ether (100 ml) cooled to −60° C. A white powdery precipitate started to separate almost immediately. The addition was complete after 5 minutes and the reaction mixture was allowed to warm to room temperature during about 1 hour. The solvent was removed in vacuo and the residue washed with ether to give the title compound[1] as a yellow solid (2.566 g).

$^1$H NMR (δDMSO) 7.26–7.38 (3H, m), 7.79 (1H, dd), 7.90 (1H, dd).

Ref. 1L T. Hamada, O. Yonemitsu; Synthesis, 852, 1986—for the general method.

Intermediate 46
Benzo[b]thiophene-2-sulfonyl chloride

To a stirred suspension of the finely powdered Intermediate 45 (3.04 g) in anhydrous n-hexane (75 ml) was added sulphuryl chloride (1.2 ml) in anhydrous n-hexane (35 ml) in portions at 0° C. over 1 minute. During the addition the lithium arylsulfinate did not dissolve, and then a white precipitate formed. After 10 min, ice cold ether was added and the mixture was filtered. The residue was washed with cold ether (5 ml) and the filtrate concentrated in vacuo to give the title compound as a pale yellow solid (2.462 g). Analysis Found: C,40.7; H,2.0 C$_8$H$_5$S$_2$O$_2$Cl requires C,41.3; H,2.2; T.l.c. (SiO$_2$) (1:1)=0.35 detection KMnO$_4$.

Intermediate 47
rel-(2R,3S)-2-(1R-Carboxy-but-3-enyl)-3-(quinoline-8-sulfonylamino)-pyrrolidine-1-carboxylic acid benzyl ester Intermediate 12 (0.185 g), 8-quinolylsulphonyl chloride (0.173 g), triethylamine (0.46 ml) and dichloromethane (10 ml) were mixed at 5° C. under nitrogen for 2 h. The solvent was then removed in vacuo and the residue partitioned between 1M hydrochloric acid and ethyl acetate. The organic layer was separated and washed with brine and dried (MgSO$_4$). Solvent material in vacuo gave the title compound as a colourless foam (0.219 g). T.l.c. (1:1 hexane:ethyl acetate) Rf 0.23 (streak) Mass Spec. MH$^+$ (found) 492 MH$^+$ (calculated) 492.

Intermediate 48
rel-2R-(3S-tert-Butoxycarbonylamino-pyrrolidin-2R-yl)-pentanoic acid methyl ester Intermediate 9 (6.274 g), 10% palladium on charcoal (0.250 g) and ethyl acetate were hydrogenated for 24 h. The catalyst was filtered off over hyflo and the filtrate concentrated in vacuo to afford the title compound (3.975 g) as a white solid. T.l.c. (ethyl acetate) Rf 0.12. Assay Found: C,60.04; H,9.36; N,9.78%. C$_{15}$H$_{28}$N$_2$O$_4$ requires C,59.98; H,9.39; N,9.33%.

Intermediate 49
rel-2R-(3S-tert-Butoxycarbonylamino-1-methanesulfonyl-pyrrolidin-2R-yl)-pentanoic acid methyl ester Intermediate 48 (1.670 g), methanesulphonyl chloride (0.43 ml), triethylamine (0.85 ml) and dichloromethane (25 ml) were mixed at 5° C. under nitrogen for 30 min. The solvent was then removed in vacuo and the residue partitioned between water and ethyl acetate. The organic layer was separated, washed with brine and dried (MgSO4). The solvent was removed in vacuo to afford the title compound as a white solid (1.941 g). T.l.c. (ethyl acetate) Rf 0.58. Mass Spec. MH$^+$ (found) 379 MH$^+$ (calculated) 379.

Intermediate 50
rel-2R-(3S-Amino-1-methanesulfonyl-pyrrolidin-2R-yl)-pentanoic acid methyl ester Intermediate 49 (1.872 g) and 4M hydrogen chloride in dioxan were stirred under nitrogen for 5 h. The solvent was then removed in vacuo and the residue partitioned between ether and water. The aqueous layer was separated and washed with ether (3×25 ml) and then basified with 8% sodium hydrogen carbonate. This solution was then concentrated in vacuo and the residue extracted with ethyl acetate (6×50 ml). The combined extracts were concentrated in vacuo to afford the title compound as a white solid (1.16 g). T.l.c. (ethyl acetate) Rf 0.22 (streak) Mass Spec. MH$^+$ (found) 279 MH$^+$ (calculated) 279.

Intermediate 51
rel-2R-[3S-(Isoquinoline-5-sulfonylamino)-1-methanesulfonyl-pyrrolidin-2R-yl]-pentanoic acid methyl ester Intermediate 50 (0.100 g), 5-isoquinolinesulphonyl chloride hydrochloride (0.095 g), pyridine (0.29 ml) and dichloromethane (10 ml) were mixed for 2 days. The volatiles were removed in vacuo. The residue was dissolved in 1M hydrochloric acid (3 ml) (Extract A) and extracted with ethyl acetate (3×25 ml). These were combined and the solvent removed in vacuo. The residue was dissolved in water (5 ml) and taken to pH5 with 8% sodium hydrogen carbonate solution. Extraction with ethyl acetate (3×5 ml), combination of extracts, drying (MgSO$_4$) and solvent removal in vacuo gave the title compound as a white solid (0.062 g). Extract A was concentrated in vacuo and the residue dissolved in water (5 ml). This was taken to pH5 with 8% sodium hydrogen carbonate solution and extracted with ethyl acetate (2×10 ml). The combined extracts were dried (MgSO$_4$) and the solvent removed in vacuo to afford further product (0.034 g). Further basification of the aqueous layer with 8% sodium hydrogen carbonate to pH8, followed by concentration in vacuo gave a white solid. This was extracted with ethyl acetate (3×10 ml). The combined extracts were concentrated in vacuo to afford starting material (0.024 g). Data for title compound: T.l.c. (ethyl acetate) Rf 0.19.

A. Morikawa, T. Sone, T. Asano, *J. Med. Chem.*, 1989, 32, 42.

Intermediate 52
rel-2R-[3S-(Isoquinoline-5-sulfonylamino)-1-methanesulfonyl-pyrrolidin-2R-yl]-pentanoic acid Prepared in a similar manner to Intermediate 54 from Intermediate 51 to give the title compound. Mass Spec. MH+ (found) 456 MH+ (calculated) 456.

Intermediate 53
rel-2R-[1-Methanesulfonyl-3S-(quinoline-8-sulfonylamino)-pyrrolidin-2R-yl]-pentanoic acid methyl ester Intermediate 50 (0.100 g), 8-quinolinesulphonyl chloride (0.082 g), pyridine (0.29 ml) and dichloromethane (20 ml) were mixed together for 24 h. The volatiles were then removed in vacuo and the residue partitioned between ethyl acetate and 1M hydrochloric acid. The acidic layer was separated and extracted with ethyl acetate (20 ml). The combined organic extracts were washed with brine (10 ml), dried (MgSO$_4$) and concentrated in vacuo to afford the title compound as a white foam (0.094 g). Further work-up on the aqueous acidic extracts according to Intermediate 51 gave unreacted starting material (0.034 g). Title compound: T.l.c. (ethyl acetate) Rf 0.48.

Intermediate 54
rel-2R-[1-Methanesulfonyl-3S-(quinoline-8-sulfonylamino)-pyrrolidin-2R-yl]-pentanoic acid Intermediate 53 (0.090 g), potassium hydroxide (0.110 g), water (3.5 ml) and ethanol (5 ml) were warmed at 80° C. for 11 h. After neutralisation to pH7 with 8% sodium hydrogen carbonate solution, the mixture was concentrated in vacuo and azeotroped with toluene (20 ml). The residue was washed with acetone (3×20 ml) and this residue then used in the next reaction without further purification. Mass Spec. MH+ (found) 456 MH+ (calculated) 456.

Intermediate 55
4-Amino-2S-tert-butoxycarbonylamino-butyric acid

N$^\alpha$-$^t$BOC-(L)glutamine (5.0 g) was added in one portion to a solution of phenyl iodosylbis(trifluoroacetate) [PIFA] (11.64 g) in 50% aqueous acetonitrile (150 ml) at room temperature and the solution stirred for 15 min. Pyridine (2.71 ml) was then added and the solution aged for 64 h. The solution was then evaporated to dryness in vacuo, and the residual brown oil dissolved in water (50 ml), washed with ether (2×75 ml) and the aqueous again evaporated to dryness in vacuo, to give the title compound as a brown oil (11.46 g): $^1$H NMR (DMSO-d$_6$) d 1.40 (s, 9H), 2.10–1.80 (m, 2H), 2.85 (m, 2H), 4.05, (m, 1H).

Intermediate 56
4-Benzyloxycarbonylamino-2S-tert-butoxycarbonylamino-butyric acid A solution of Intermediate 55 (11.4 g) (crude) in 50% aqueous dioxan (120 ml) was cooled to 0° to 10° C. (ice bath) and the pH adjusted to 8.8 with sodium bicarbonate. A solution of N-(benzyloxycarbonyloxy)succinimide (5.57 g) in dioxan (20 ml) was added in one portion, the pH readjusted to 8.8 and the mixture stirred at room temperature for 18 h. The mixture was then filtered, the filtrate washed with diethyl ether (2×100 ml) and the aqueous acidified to 2 with 2 N HCl, and extracted with ethyl acetate (3×150 ml). The combined organic extracts were dried (MgSO$_4$) and evaporated to dryness in vacuo to give the title compound as a brown oil (7.35 g):

$^1$H NMR (DMSO-d$_6$) d 1.39 (s, 9H), 1.70 (m, 1H), 1.85 (m, 1H), 3.05 (m, 2H), 3.90 (m, 1H), 5.05 (s, 2H), 7.10 (d, 1H), 7.35 (s, 5H).

Intermediate 57
(3-Benzyloxycarbonylamino-1S-hydroxymethyl-propyl)-carbamic acid tert-butyl ester N-methyl morpholine (2.5 ml) was added dropwise to a stirred solution of the crude N$^\alpha$-$^t$BOC-N$^g$-Z-(L)-diaminobutryic acid of Intermediate 56. (7.15 g) in dry THF (70 ml) under nitrogen at −15° to −10° C. over 5 min. Ethyl chloroformate (2.2 ml) was then added dropwise maintaining the temperature below −10° C., the mixture cooled to −16° C., and stirred for 15 mins. A freshly prepared solution of sodium borohydride (2.31 g) in water (20 ml) was then added over 30 mins, maintaining the temperature below −10° C., and the mixture aged at −16° C. for 5 min. The mixture was then poured into water (400 ml) and stirred vigorously for 15 min before being extracted with ethyl acetate (5×50 ml). The combined organic extracts were then washed with 1 N HCl (100 ml), water (100 ml), saturated aqueous sodium bicarbonate (100 ml), and brine (100 ml), dried (MgSO$_4$) and evaporated to dryness in vacuo. The residual clear oil was purified further by chromatography on silica gel. Elution with neat dichloromethane and dichloromethane/methanol (19/1) gave the title compound as a semi-crystalline oil, which after trituration with cyclohexane/diethyl ether (10/1), gave the title compound as a white solid (3.31 g, 48% from N$^\alpha$-BOC-(L)-glutamine): mp 78–79° C.; $[\alpha]^{26}_D$ −37.05° (c 1, MeOH)s;

Intermediate 58
6-Benzyloxycarbonylamino-4S-tert-butoxycarbonylamino-hex-2E-enoic acid ethyl ester Oxalyl chloride (0.74 ml) was added dropwise to a stirred solution of DMSO (0.63 ml) in anhydrous DCM (19 ml) under nitrogen at −70° C. over 5 min and the solution stirred for 15 min. A solution of the aclohol, of Intermediate 57, (1.10 g) in DCM (10 ml) was then added over 15 mins, and the solution stirred for a further 15 min, while warming to ca −50° C. Triethylamine (4.35 ml) was then added over 10 min and the cooling adjusted to allow the mixture to attain ca −30 ° C. (Carbethoxymethylene) triphenylphosphorane (1.70 g) was then added in one portion, and then mixture allowed to warn to room temperature over 1 h, before being partitioned between diethyl ether (35 ml) and satured brine (35 ml). The aqueous phase was further extracted with diethyl ether (2×10 ml) and the combined organics dried (MgSO$_4$) and evaporated to dryness in vacuo. The residual yellow oil was purified further by chromatography on silica gel. Elution with cyclohexane/ethyl acetate (3:2) gave the title compound as a clear foam (611 mg. 46.2%):

$^1$H NMR (DMSO-d$_6$) d 1.25 (t, 3H), 1.40 (s, 9H), 1.65 (m, 2H), 3.05 (m, 2H), 4.15 (q, 2H), 5.05 (s, 2H), 5.90 (d, 1H), 6.80 (dd, 1H), 7.20 (d, 1H), 7.25 (d,1H) 7.40 (s, 5H).

Intermediate 59
(2R,3S)-3-tert-Butoxycarbonylamino-2-ethoxycarbonylmethyl-pyrrolidine-1-carboxylic acid benzyl ester Tetramethylethylenediamine (0.23 ml) and lithium bis (trimethylsilylamide) (1.0M in hexanes, 1.56 ml) were added dropwise to a solution of the ester, of Intermediate 58 (2.53 g) in anhydrous toluene (35 ml) under nitrogen and the solution stirred at room temperature for 1 h. The solution was then partitioned between saturated aqueous ammonium chloride (65 ml) and ethyl acetate (65 ml). The aqueous phase was further extracted with ethyl acetate (2×10 ml), and the combined organics washed with saturated brine (30 ml), dried (MgSO$_4$) and evaporated to dryness in vacuo. The residual yellow oil was purified further by chromatography on silica gel. Elution with cyclohexane/ethyl acetate (3:2) gave the title compound as a clear oil (1.85 g, 73.1%): [α]$^{23}_D$ −30° (c 1.1, MeOH); $^1$H NMR (DMSO-d$_6$) d 1.15 (t, 3H), 1.35 (s, 9H), 1.70 (m, 1H), 2.05 (m, 1H), 2.60–2.40 (m, 2H), 3.45 (m, 1H), 3.85 (d, 2H), 4.00 (q, 2H), 5.05 (s, 2H), 7.25 (m, 1H), 7.35 (s, 5H).

Intermediate 60

4-Benzyloxycarbonylamino-2R-tert-butoxycarbonylamino-butyric acid

Benzyl alcohol (4.0 ml) was added to a stirred solution containing N$^α$-$^t$BOC-(D)-glutamine (510 mg), phenyl iodosylbis(trifluoroacetate) (902 mg) and triethylamine (0.56 ml) in DMF (7 ml) and the solution stirred between 40–50° C. under nitrogen for 2 h. The solution was then cooled, diluted with ethyl acetate (100 ml), and extracted with saturated aqueous sodium bicarbonate (3×100 ml). The combined aqueous extracts were washed with ethyl acetate (50 ml), acidified to pH 2 with concentrated HCl and the solution extracted with ethyl actetate (3×100 ml). The combined organic extracts were washed with brine (50 ml), dried (MgSO$_4$) and evaporated to dryness in vacuo, and the residual pale yellow syrup was purified further by chromatography on silica gel. Elution with dichloromethane/methanol (9/1) gave the title acid as a white foam (626 mg, 86%): [a]$^{21}_D$ +5.1° (c 1.2, MeOH);

$^1$H NMR (DMSO-d$_6$) d 1.38 (s, 9H), 1.65 (m, 1H), 1.85 (m, 1H), 3.05 (m, 2H), 3.76 (m, 1H), 5.00 (s, 2H), 6.33 (d, 1H), 7.13 (t, 1H), 7.34 (s, 5H).

Intermediate 61

(3-Benzyloxycarbonylamino-1R-hydroxymethyl-propyl) carbamic acid tert-butyl ester N-methyl morpholine (6.0 ml) was added dropwise to a stirred solution of the crude N$^α$-$^t$BOC-N$^g$-Z-(D)-diaminobutryic acid, of Intermediate 60 (19.4 g) in dry THF (160 ml) under nitrogen at −15° to −10° C. over 5 min. Ethyl chloroformate (5.26 ml) was then added dropwise maintaining the temperature below −10° C., the mixture cooled to −16° C., and stirred for 15 mins. A freshly prepared solution of sodium borohydride (6.24 g) in water (50 ml) was then added over 30 mins, maintaining the temperature below −10° C., and the mixture aged at −16° C. for 5 min. The mixture was then poured into water (250 ml) and stirred vigorously for 15 min before being extracted with ethyl acetate (2×450 ml). The combined organic extracts were then washed with 1 N HCl (2×100 ml), water (100 ml), saturated aqueous sodium bicarbonate (2×100 ml), and brine (100 ml), dried (MgSO$_4$) and evaporated to dryness in vacuo. The residual clear oil was purified further by chromatography on silica gel. Elution with neat dichloromethane and dichloromethane/methanol (19/1) gave the title compound as a semi-cystalline oil, which after trituration with cyclohexane/diethyl ether (10/1), gave the title compound as a white solid (11.5 g, 61.6%): [α]$^{21}_D$ +52.2° (c 0.94, CHCl$_3$) $^1$H NMR (DMSO-d$_6$) d 1.40 (s, 9H), 3.00 (m, 2H), 3.23 (m, 2H), 4.60, (t, 1H), 5.00 (s, 2H), 6.50 (d 1H), 7.05 (s, 1H) 7.38 (m. 5H), 12.50 (m, 1H).

Intermediate 62

6-Benzyloxycarbonylamino-4R-tert-butoxycarbonylamino-hex-2E-enoic acid ethyl ester Oxalyl chloride (6.26 ml) was added dropwise to a stirred solution of DMSO (6.08 ml) in anhydrous DCM (105 ml) under nitrogen at −70° C. over 5 min and the solution stirred for 15 min. A solution of the alcohol, of Intermediate 61 (11.14 g) in DCM (100 ml) was then added over 15 mins, and the solution stirred for a further 15 min, while warming to ca −50° C. Triethylamine (44.9 ml) was then added over 10 min and the cooling adjusted to allow the mixture to attain ca −30° C. (Carbethoxymethylene) triphenylphosphorane (17.2 g) was then added in one portion, and then mixture allowed to warm to room temperature over 1 h, before being partitioned between diethyl ether (600 ml) and satured brine (200 ml). The aqueous phase was further extracted with diethyl ether (2×600 ml) and the combined organics dried (MgSO$_4$) and evaporated to dryness in vacuo. The residual yellow oil was purified further by chromatography on silica gel. Elution with cyclohexane/ethyl acetate (3:2) gave the title compound as a clear foam (10.8 g, 80.1%): [α]$^{21}_D$ +25.7° (c 0.74, CHCl$_3$).

Intermediate 63

(2S,3R)-3-tert-Butoxycarbonylamino-2-ethoxycarbonylmethyl-pyrrolidine-1-carboxylic acid benzyl ester Tetramethylethylenediamine (0.99 ml) and lithium bis (trimethylsilylamide) (1.0M in hexanes, 6.56 ml) were added dropwise to a solution of the ester, of Intermediate 62 (10.67 g) in anhydrous toluene (94 ml) under nitrogen and the solution stirred at room temperature for 1 h. The solution was then partitioned between saturated aqueous ammonium chloride (200 ml) and ethyl acetate (500 ml). The aqueous phase was further extracted with ethyl acetate (2×500 ml), and the combined organics washed with saturated brine (2×200 ml), dried (MgSO$_4$) and evaporated to dryness in vacuo. The residual yellow oil was purified further by chromatography on silica gel. Elution with cyclohexane/ethyl acetate (3:2) gave the title compound as a clear oil (6.01 g, 56.3%).

Intermediate 64

(2R,3S)-3-tert-Butoxycarbonylamino-2-(1R-ethoxycarbonyl-but-3-enyl)-pyrrolidine-1 carboxylic acid benzyl ester Lithium hexamethyldisilylamide (1.0M, tetrahydrofuran, 1.92 ml) was added dropwise to a stirred solution of Intermediate 59 (245 mg) in dry tetrahydrofuran (2.5 ml) and 1,3-dimethyl-3,4,5,6-tetrahydro-2-(1H)-pyrimidinone (4.3 ml) under nitrogen at −70° C. After stirring for 1 hour, allyl iodide (69 μl) was added, whilst maintaining the internal temperature below −68° C., and stirring continued for a further 2 hours. Saturated ammonium chloride (1 ml) was added and the mixture allowed to warm to room temperature. Water (5 ml) and ether (5 ml) were added to the mixture, the aqueous phase separated, extracted with ethyl acetate (2×5 ml) and the combined organic extracts washed with brine (5 ml). The solvent was removed from the organic phase in vacuo to leave a yellow oil which was purified by flash column chromatography using Merck 9385 silica and eluting with ethyl acetate/n-hexane (3:2). The required fractions were combined and the solvent removed in vacuo to give the title compound as a colourless oil, (171 mg). T.l.c. SiO$_2$, ethyl acetate:n-hexane (3:7) Rf=0.27.

Intermediate 65

(2R,3S)-3-tert-Butoxycarbonylamino-2-(1R-carboxy-but-3-enyl)-pyrrolidine-1-carboxylic acid benzyl ester A solution of potassium hydroxide (198 mg) in water (5 ml) was added to a stirred solution of Intermediate 64 (165 mg) in ethanol (5 ml). The mixture was heated at 55° C. for 6 hours before cooling to room temperature. The ethanol was removed from the mixture in vacuo before the remaining solution was adjusted to pH1 by the addition of 2M hydrochloric acid. The precipitate was extracted with ethyl acetate (3×10 ml), the combined organic extracts dried (MgSO$_4$), the solution filtered and the solvent removed in vacuo to give the title compound as a pale yellow foam (166 mg). T.l.c. SiO$_2$, Ether Rf=0.38.

Intermediate 66
(2R,3S)-3-Amino-2-(1R-carboxy-but-3-enyl)-pyrrolidine-1-carboxylic acid benzyl ester hydrochloride A solution of Intermediate 65 (163 mg) in hydrogen chloride dioxan (4.0M, 10 ml) was stirred at 22° C. for 4 hours. The solvent was removed in vacuo to give the title compound as a pale yellow solid (136 mg). T.l.c. SiO$_2$, n-butanol, acetic acid, water (4:1:1) Rf=0.51. Circular Dichroism (MeCN, 1.04×10$^{-4}$) λ=218.4 nm, δE=+0.77.

Intermediate 67
(3aS,6R,6aR)-Allyl-5-oxo-hexahydro-pyrro[3,2-b]pyrrole-1-carboxylic acid benzyl ester 2-Chloro-1-methylpyridinium iodide (125 mg) was added in one portion to a stirred solution of Intermediate 66 (116 mg) and diisopropylethylamine (57 ml) in dry dichloromethane (50 ml) at room temperature under nitrogen. After 20 minutes, a further addition of diisopropylethylamine was made (114 ml) and stirring continued for 14 hours. After removal of the solvent in vacuo, the residue was purified by flash column chromatography on silica using (Merck 9385) eluting with ethyl acetate. The required fractions were combined and the solvent removed to give the title compound as a colourless oil which upon scratching in n-hexane crystalised, (34 mg). T.l.c. (SiO$_2$, ethyl acetate) Rf=0.42.

Chiral HPLC Sumichiral OA4100 Column, 15% EtOH/heptane Flow rate=1.0 ml/min, u.v.@ 220 nm retention time=10 min Intermediate 67 and 68

A racemic sample of Intermediate 13 (500 mg) was separated into its enantiomers by chiral HPLC. (Sumichiral OA4100 column, eluent system 10% ethanol/heptane, flow rate=20 ml/min) to give:
Enantiomer 1 (Intermediate 68)
(3aR,6S,6aS)-1-allyl-5-oxo-hexahydro-pyrrolo[3,2-b]pyrrole-1-carboxylic acid benzyl ester (121 mg)

Chiral HPLC (Sumichiral OA4100 column, eluent system 15% ethanol/heptane, flow rate 1.0 ml/min). Retention time 8.6 min, >99% e.e.
Enantiomer 2 (Intermediate 67)
(3aS,6R,6aR)-6-allyl-5-oxo-hexahydro-pyrrole[3,2-b]pyrrole-1-carboxylic acid benzyl ester (136 mg)

Chiral HPLC (system as for enantiomer 1). Retention time=10.0 min, 84% e.e.

Intermediate 68 (Alternative Synthesis)
(3aR,6S,6aS)-6-Allyl-5-oxo-hexahydro-pyrrolo[3,2-b]pyrrole-1-carboxylic acid benzyl ester A solution of t-butylmagnesium chloride in tetrahydrofuran (1.0M, 96 ml) was added dropwise to a cold (−5° C.) stirred solution of Intermediate 106 (10.8 g) in dry tetrahydrofuran (24 ml) under nitrogen. Once the addition was complete the mixture was stirred for 2 h at −10° C. then quenched with dilute hydrochloric acid (2M, 70 ml) added dropwise maintaining the internal temperature below 0° C. Ethyl acetate (70 ml) was added and the layers were separated. The acqueous layer was re-extracted with ethyl acetate and the combined organic solutions were washed with saturated brine dried (Na$_2$SO$_4$) and concentrated in vacuo to give an orange oil. This was purified by flash column chromatography on silica gel with dichloromethane methanol (49:1) as eluent. Concentration of the appropriate fractions gave a yellow oil which slowly crystallised on standing. The resulting solid was triturated with ether to give the title compound (7.1 g) as a white solid. Tlc (dichloromethane:methanol;49:1) Rf=0.4.

Intermediate 69
(3S,3aS,6aR)-1-(Naphthalene-2-sulfonyl)-3-propyl-hexahydro-pyrrol[3,2-b]pyrrol-2-one Prepared in a similar manner to Intermediate 14 from Example 53 to give the title compound as a white foam.

Chiral HPLC (Chiracel OD-H column, eluent system propan-2-ol:triethylamine:heptane; 5:1:94, flow rate=1 ml/min). Retention time=23.1 min, >98% e.e.

Intermediate 70
(3R,3aR,6aS)-1-(Naphthalene-2-sulfonyl)-3-propyl-hexahydro-pyrrol[3,2-b]pyrrol-2-one Prepared in a similar manner to Intermediate 14 from Example 55 to give the title compound as a white foam.

Chiral HPLC (Chiracel OD-H column, eluent system propan-2-ol:triethylamine:heptane; 5:1:94; flow rate=1 ml/min). Retention time=24.5 min, 83% e.e.

Intermediate 71
1-{3-[(Benzyloxy-carbonyl)-amino]-1-hydroxymethyl-propyl}-carbamic acid, tert-butyl ester A solution of compound Nα-BOC,Nγ-CBZ-2,4-Diaminobutyric acid (3.198 g) in tetrahydrofuran (44 ml, dry) was cooled to −10° C. under nitrogen, 4-methylmorpholine (1.0 ml) was added followed by ethylchloroformate (0.868 ml). After stirring for 8 mins sodium borohydride (1.03 g) was added in one portion followed by methanol (88 ml) over a period of 11 mins at 0° C. The mixture was stirred at ca 0° C. for an additional 11 mins before 1M hydrochloric acid (18 ml) was added. The mixture was evaporated under reduced pressure and the aqueous residue was extracted with ethyl acetate. The organic layer was separated and washed with 1M hydrochloric acid, water, saturated aqueous sodium bicarbonate solution and water, then dried (magnesium sulphate), evaporated under reduced pressure and some of the residue (1.8 g from 2.87 g) was purified by chromatography (Merck 7734) using cyclohexane:ethylacetate (3:2) as eluent to give the title compound (1.6 g): t.l.c. (1:1 cyclohexane:ethyl acetate) Rf 0.23 ir (CHBr$_3$) 3432, 1704 cm$^{-1}$.

Intermediate 72
6-Benzyloxycarbonylamino-4-tert-butoxycarbonylamino-hex-2E-enoic acid ethyl ester A solution of dimethyl sulfoxide (6.82 ml) in dry dichloromethane (135 ml) was stirred under N$_2$ and cooled (dry ice/acetone) to −72° C. Oxalyl chloride (7.4 ml) was added dropwise over 10 minutes (temp kept in the range −60→65° C.) and the reaction was stirred for 15 minutes. A solution of the alcohol, Intermediate 71, (12.6 g) in dry dichloromethane (135 ml) was added over 20 minutes (temp kept in the range −60→63° C.) and the reaction mixture then stirred for 20 minutes by which time the temperature had risen to −52° C. Triethylamine (53.7 ml) was added dropwise over 10 minutes followed by the immediate addition of the Wittig reagent (19.3 g). The cooling bath was removed and the internal temperature allowed to rise to 17° C. The reaction mixture was poured into ether (400 ml) and brine (400 ml). The organic phase was separated and the aqueous phase extracted with ether (2×100 ml). The combined organic phases were dried (MgSO$_4$) and evaporated under reduced pressure to give a tan oil (36.22 g). This was purified by flash column chromatography (Merck 9385 silica eluting with 40% ethyl acetate in cyclohexane) to give the product (15.71 g) as an oil: $^1$H NMR (CDCl$_3$); 7.40–7.30 (5H, m), 6.86 (1H, dd), 5.93 (1H, dd), 5.42–5.28 (1H, br), 5.12 (2H, ABq), 4.72–4.60 (1H, m), 4.50–4.32 (1H, m), 4.19 (2H, q), 3.60–3.30 (1H, m), 3.15–2.98 (1H, m), 2.00–1.80 (1H, m), 1.65–1.50 (1H, m), 1.45 (9H, s) and 1.28 (3H, t), R$_f$ 0.45 (2:3 ethyl acetate/cyclohexane).

Intermediate 73
rel-(2R,3S)-3-tert-Butoxycarbonylamino-2-ethoxycarbonylmethyl-pyrrolidine-1-carboxylic acid benzyl ester Intermediate 72 (12.2 g) was suspended in dry toluene (175 ml) with stirring under N$_2$. Tetramethylethylenediamine (1.1 ml) was added followed by lithium bis-(trimethylsilyl)amide (1.0M in hexanes, 7.6 ml). On completion of the addition a solution had formed. The reaction mixture was stirred for 15 minutes and then poured into ethyl acetate (300 ml) and saturated aqueous ammonium chloride (300 ml). The organic phase was separated and the aqueous phase extracted with ethyl acetate (2×50 ml). The combined organic extracts were washed with brine (150 ml) and the aqueous phase extracted with ethyl acetate (2×25 ml). The combined organic extracts were dried (MgSO$_4$) and evaporated under reduced pressure to give a tan oil (12.86 g) which was filtered through a plug of silica gel using ethyl acetate/cyclohexane (2/3) as eluant to give a crude mixture including title compound (10.74 g) as an oil. This oil was purified further by flash column chromatography on silica gel. Elution with ethyl acetate/cyclohexane (2/3) gave the title compound, as a solid (8.49 g, 69.7%). A small sample of the title compound was crystallised from ether to give a white solid: $^1$H NMR (CDCl$_3$); 7.40–7.30 (5H, m), 5.12 (2H, s), 4.72–4.53 (1H, m), 4.20–3.95 (4H, m), 3.65–3.40 (2H, m), 2.95–2.65 (1H, m), 2.60–2.40 (1H, m), 2.25–2.10 (1H, m), 1.92–1.75 (1H, m), 1.40 (9H, s) and 1.30–1.15 (3H, m). R$_f$ 0.8 (1:1, ethyl acetate/cyclohexane).

Intermediate 74
rel-(2R,3S)-3-amino-2-ethoxycarbonylmethyl-pyrrolidine-1-carboxylic acid benzyl ester Intermediate 73 (30.0 g) was dissolved in 1:1 TFA/DCM (300 ml) and stirred at room temperature for 2.5 h under nitrogen. The solution was evaporated to dryness in vacuo, dissolved in DCM (500 ml) and washed with saturated aqueous potassium bicarbonate (3×250 ml). The combined aqueous phases were extracted with DCM (300 ml) and the organics dried (MgSO$_4$) and evaporated to dryness in vacuo to a give yellow oil (20.9 g, 92%): $^1$H NMR (DMSO-d$_6$) 7.50–7.30 (5H, m), 5.10 (2H, s), 4.15–4.00 (2H, m), 3.75 (1H, bs), 3.62–3.45 (1H, m), 3.45–3.30 (1H, m), 3.30 (1H, m), 2.70–2.40 (2H, m), 2.10–21.90 (1H, m), 1.68–1.52 (1H, m), 1.28–1.12 (3H, m); Anal. (C$_{16}$H$_{22}$N$_2$O$_4$, 0.15 H$_2$O requires C: 62.12; H: 7.00; N:, 9.10 found C: 62.12; H: 7.00; N:, 9.10 found C: 62.18; H: 7.27; N:, 9.06.

Intermediate 75
(2S,3R)-3-Amino-2-ethoxycarbonylmethyl-pyrrolidine-1-carboxylic acid benzyl ester(−)tartrate
(−)-Di-p-toluoyl-(L)-tartaric acid monohydrate [(−)-DPTTA] (26.4 g, 65.3 mmol) was added to a solution of Intermediate 74; (20.0 g, 65.3 mmol) in ethanol (930 ml). The solution was aged at 5° C. for 18 hr and the white solid harvested and washed with cold ethanol to yield white crystals (21.6 g). The solid was recrystallised from hot ethanol (250 ml) to give the salt as a white solid (7.2 g): [a]$^{23.5}_D$ −85.9° (c 1.06, MeOH); Mp 174–175° C.; Chromatography Chiralpak AD Col 287; 10% IPA/Heptane (+0.1% TEA); 1 ml/min; 254 nm; >97% e.e.;

Intermediate 76
(2R,3S)-3-Amino-2-ethoxycarbonylmethyl-pyrrolidine-1-carboxylic acid benzyl ester(+)tartrate The mother liquors from the first crystallisation during the preparation of Intermediate 75 were evaporated to dryness in vacuo to yield a white solid (23.5 g) which was suspended in EtOAc/H$_2$O (1:1; 300 ml) and treated with a solution of potassium carbonate (4.8 g, 34 mmol) in water (50 ml). This was partitioned with a further portion of EtOAc (50 ml). The aqueous phase was further extracted with ethyl acetate (3×100 ml), and the combined organics washed with saturated brine (100 ml), dried (MgSO$_4$) and evaporated to dryness in vacuo to yield a brown oil (12.9 g). Analysis of the oil by HPLC revealed continuing presence of tartrate so the partitioning and extraction were repeated and the combined organics evaporated to dryness in vacuo to yield a brown oil (10.7 g). The oil was suspended in ethanol (215 ml) and treated with a solution of (+)-Di-(p)-toluoyl-tartaric acid monohydrate [(+)-DPTTA] (13.2 g, 32.7 mmol) in ethanol (250 ml) and the mixture stirred at 20° C. for 30 mins, and then aged at 5° C. for 18 hr. The white solid formed was harvested and washed with cold ethanol to yield white crystals (14.2 g). The solid was recrystallised from hot ethanol (590 ml) to give a white solid (6.2 g): [a]$^{23.5}_D$ +56.82° (c 0.86, MeOH); Mp 180–181° C.; Chromatography Chiralpak AD Col 287; 10% IPA/Heptane (+0.1% TEA); 1 ml/min; 254 nm; >97% e.e.

Intermediate 59
(2R,3S)-3-tert-Butoxycarbonylamino-2-ethoxycarbonylmethyl-pyrrolidine-1-carboxylic acid benzyl ester Triethylamine (6.5 ml) was added to a suspension of the salt Intermediate 76 (5.5 g) in dioxan (107 ml) and stirred vigorously for 40 mins. Di$^t$butyl dicarbonate (3.4 g) was then added and the mixture stirred for 1 hr. Analysis of mixture (HPLC) showed incomplete reaction so a further portion of the di$^t$butyl dicarbonate (0.3 g, 1.4 mmol) was added and the mixture stirred for a further 30 mins and was diluted with ethyl acetate (100 ml). This mixture was washed with 10% aqueous citric acid (3×100 ml), water (100 ml), saturated aqueous sodium bicarbonate (100 ml) and brine (100 ml). The organics evaporated to dryness in vacuo and the residual clear oil purified further by chromatography on silica gel. Elution with cyclohexane/ethyl acetate (3/1) gave the title compound as a clear oil(6.5 g): [a$^{22.5}_D$ −31.7° (c 0.79, MeOH);

Intermediate 63
(2S,3R)-3-tert-Butoxycarbonylamino-2-ethoxycarbonylmethyl-pyrroldine-1-carboxylic acid benzyl ester Triethylamine (7.8 ml) was added to a suspension of the salt Intermediate 75 (12.8 g) in dioxan (127 ml) and stirred vigorously for 40 mins. Di t-butyl dicarbonate (4.8 g) was then added and the mixture stirred for 1 hr. The suspension was diluted with ethyl acetate (1000 ml) and was washed with 10% aqueous citric acid (2×150 ml), water (100 ml), saturated aqueous sodium bicarbonate (100 ml) and brine (100 ml). The organics evaporated to dryness in vacuo and the residual clear oil purified further by chromatography on silica gel. Elution with a cyclohexane/ethyl acetate gradient system (neat cyclohexane to 31/9 cyclohexane/ethyl acetate) gave the title compound as a clear oil (7.6 g): $[\alpha]^{21}_D$ +5.0° (c 0.8, $CHCl_3$); circular dichroism [CD 520] 215 nm, dE –1.34;

Intermediate 77
2,4-Diamino-butyric acid methyl ester dihydrochloride

To D,L-diaminobutyric acid dihydrochloride (350 g) in methanol (1.6l) at 0° C. was added thionyl chloride (200 ml) over ½ h. After reflux for 3 h, the solvent was removed in vacuo and the residue triturated with toluene (650 ml) to give the title compound as a white solid (385 g). Mass spec. of free base $M^+$ (found) 133 $M^+$ (calculated) 133.

Intermediate 78
3-Amino-pyrrolidin-2-one

Intermediate 77 (1 g), water (70 ml) and Dowex 2×8-400 mesh (16.4 ml) were stirred for 1 h. The resin was then filtered and the filtrate concentrated in vacuo to give the title compound as a white solid (0.40 g), T.l.c (18:3 ethyl acetate:methanol) Rf 0.07.

Intermediate 79
2,2,2-Trifluoro-N-(2-oxo-pyrrolidin-3-yl)-acetamide

Intermediate 78 (181 g), methyl trifluoroacetate (218 ml) and methanol (2.6 l) were suspended for 2 h. The solvent was then removed in vacuo to afford the title compound as a cream solid (355 g). Mass spec. $MNH_4^+$ (found) 214 $MNH_4^+$ (calculated) 214.

Intermediate 80
2-Oxo-3-(2,2,2-trifluoro-acetylamino)-pyrrolidine-1-carboxylic acid benzyl ester To intermediate 79 (3.5 g) and tetrahydrofuran (100 ml) at –70° C. was added lithium hexamethyidisilazide (20 ml). After ¼ h, benzyl chloroformate (2.8 ml) was added. The mixture was warmed to room temperature for 1 h and 1M hydrochloric acid (25 ml) added. After extraction with ethyl acetate (3×25 ml), the combined extracts were washed with 2% ammonia solution, 2M hydrochloric acid, brine and dried ($MgSO_4$). After solvent removal, the white solid was recrystallised from ethyl acetate:hexane 5:1 to give the title compound (4.2 g), T.l.c. (18:2 ethyl acetate:methanol) Rf 0.7.

Intermediate 81
2-Ethoxy-3-(2,2,2-trifluoro-acetylamino)-pyrrolidine-1-carboxylic acid benzyl ester To Intermediate 80 (34 g) in ethanol (1070 ml) at –5° C. was added sodium borohydride (9.86 g). A solution of 4M hydrogen chloride in 1,4-dioxan (20 ml) was then added dropwise. Periodically further portions of 4M hydrogen chloride in 1,4-dioxan (2×5 ml, 1×10 ml) and sodium borohydride (2 g) were added. After 3 h, concentrated sulphuric acid (11 ml) was added and the mixture warmed to room temperature for 2 h. Saturated aqueous sodium bicarbonate (300 ml) was then added and the ethanol and dioxan removed in vacuo. The residue was diluted with water (500 ml) and extracted with ethyl acetate (3×500 ml). The combined extracts were washed with brine and dried ($MgSO_4$). The solvent was removed in vacuo and the residue purified by flash chromatography on silica gel 9385 eluting with ether, to give the title compound (21 g). Mass spec. $MNH_4^+$ (found) 378 $MNH_4^+$ (calculated) 378.

Intermediate 82
trans-2-(1-Ethoxycarbonyl-2-methyl-propyl)-3-(2,2,2-trifluoro-acetylamino)-pyrrolidine-1-carboxylic acid benzyl ester Intermediate 81 (10 g), ethyl trimethylsilyl isopropylketene acetal (11 ml) and dichloromethane (250 ml) were cooled to 5° C. and boron trifluoride dietherate (17 ml) added over ¼ h. After 1 h, further boron trifluoride dietherate (3.4 ml) and ketene acetal (11 ml) were added. After a further 1 h, 1M hydrochloric acid (200 ml) was added and the organic layer separated and washed with brine and dried ($MgSO_4$). Solvent removal in vacuo gave the title compound (16.7 g), T.l.c. (2:1 ether:cyclohexane) Rf 0.18 and 0.27.

Intermediate 83
trans-3-Amino-2-(1-ethoxycarbonyl-2-methyl-propyl)-pyrrolidine-1-carboxylic acid benzyl ester Intermediate 82 (31 g), potassium carbonate (71 g), water (930 ml) and ethanol (930 ml) were warmed at 60° C. for 3 h. The ethanol was removed in vacuo and the aqueous residue extracted with ethyl acetate (3×300 ml). The combined extracts were washed with brine and dried ($MgSO_4$) and concentrated in vacuo to give the title compound as a brown oil (17.5 g). Mass spec. $MH^+$ (found)) 349 $MH^+$ (calculated) 349.

Intermediate 84
rel-(3R,3aR,6aS)-6-propyl-5-oxo-hexahydro-pyrrolo[3,2-b]-pyrrole-1-carboxylic acid benzyl ester Intermediate 83 (17.5 g) in tetrahydrofuran (1,800 ml) was cooled to –5° C. and 1M t-butylmagnesium chloride in tetrahydrofuran(204 ml) was added over ½ h. After 2 h, 1M hydrochloric acid (250 ml) and brine (300 ml) were added and then extracted with ethyl acetate (250 ml). After concentrating the extracts to half the volume in vacuo, the extracts were washed with brine and dried ($MgSO_4$). Solvent removal in vacuo followed by trituration with diethyl ether (60 ml) gave a white solid. This was recrystallised from ethyl acetate to give the title compound (3.4 g). Mass spec. $MH^+$ (found) 303 $MH^+$ (calculated) 303.

Intermediate 85
rel-(3R,3aR,6aS)-6-Isopropyl-4-methanesulfonyl-5-oxo-hexahydro-pyrrolo[3,2-b]pyrrole-1-carboxylic acid benzyl ester To a stirred solution of Intermediate 84 (15.01 g) in anhydrous tetrahydrofuran (950 ml) at –74° C. under nitrogen, was added 1.0M lithium hexamethyidisilylazide in tetrahydrofuran (69.5 ml) dropwise. After stirring at –74° C. for 10 min, the mixture was allowed to warm up to 0° C. over 45 min, then left at this temperature for 20 min. It was then cooled to –76° C., treated dropwise with methanesulfonyl chloride (9.61 ml) and left to stir at this temperature for 1.5 h. It was then warmed to –50° C., quenched with saturated ammonium chloride solution (480 ml) and allowed to warm up to room temperature. The mixture was partitioned between water (300 ml) and ethyl acetate (750 ml), the aqueous layer extracted with further ethyl acetate (750 ml), then the combined organic extracts washed with brine (450 ml), dried ($Na_2SO_4$) and concentrated in vacuo to a cream solid. Purification by flash column chromatography on silica (Merck 9385) eluting with ethyl acetate:cyclohexane (1:3, 1:2, 1:1 then 3:1) gave the title compound as a white crystalline solid (13.65 g). Tlc (dichloromethane) Rf 0.22 Mass spec $MNH_4^+$ (found)=398 $MNH_4^+$ (calculated)=398.

Intermediate 86
rel-(3R,3aR,6aS)-3-Isopropyl-1-methanesulfonyl-hexahydro-pyrrolo[3,2-b]pyrrol-2-one A suspension of Intermediate 85 (13.63 g) in ethyl acetate (900 ml) was added to 20% palladium hydroxide (moist) on carbon (3.16 g) and the resulting black suspension stirred vigorously under hydrogen at room temperature for 90 min. The mixture was then filtered through Harborlite J2 and concentrated in vacuo to give the title compound as a fine white powder (8.63 g). Tlc (Methanol:dichloromethane 1:9) Rf 0.50 Mass spec MH$^+$ (found)=247 MH$^+$ (calculated)= 247.

Intermediate 87 rel-4-(4-Methanesulfonyl-5-oxo-6R-propyl-hexahydro-(3aS,6aR)-pyrrolo[3,2-b]pyrrole-1-carbonyl)-benzaldehyde To a stirring solution of Intermediate 26 (100 mg) in acetonitrile (10 ml) was added 4-carboxy benzaldehyde (121 mg), 1-hydroxybenzotriazole (109 mg) then 1-(3-dimethylaminopropyl)-3-ethylcarbodiimide hydrochloride (156 mg). The resulting mixture was stirred at room temperature for 4 hours. The acetonitrile was removed in vacuo to give a yellow oil. This was dissolved in dichloromethane (50 ml) and extracted with a saturated solution of aqueous sodium bicarbonate (50 ml). The aqueons layer was then extracted with dichloromethane (2×15 ml). The combined dichloromethane extract was dried (Na$_2$SO$_4$), filtered and concentrated in vacuo to give a crude yellow/white foam containing the title compound. The crude mixture was purified by flash chromatography (SiO$_2$ Merck, 9385) eluting with 1% MeOH:DCM. The resulting fractions were concentrated in vacuo to give the title compound as a colourless foam (131 mg). T.l.c. (1:9; Methanol:Dichloromethane) Rf 0.77 Mass spec MH$^+$ (found) 379 MH$^+$ (calculated) 379.

Intermediate 88 rel-(3R,3aR,6aS)-1-Methanesulfonyl-3-propyl-4-undec-10-enoyl-hexahydro-pyrrolo[3,2-b]pyrrol-2-one To a stirred solution of Intermediate 26 (900 mg) and N,N-diisopropylethylamine (1.91 ml) in dry dichloromethane (10 ml) under nitrogen was added 10-undecenoic acid (682 mg) in dry dichloromethane (5 ml) followed by bromo-tris-pyrrolidino-phosphonium hexaflouro phosphate (1.87 g). The mixture was stirred for 2 hours before being partitioned between dichloromethane (100 ml) and 8% aqueous sodium bicarbonate solution (100 ml). The phases were separated, the aqueous phase further extracted with dichloromethane (100 ml), the combined organic phases dried (MgSO$_4$) and the solvent evaporated in vacuo to leave a yellow gum. The gum was purified by flash chromatography eluting with diethylether and the solvent removed in vacuo to give the title compound as a white solid (1.31 g), m.p=62–64.6° C. T.l.c SiO$_2$ (Diethylether) R.f=0.43.

Intermediate 89 rel-10-(4-Methanesulfonyl-5-oxo-6R-propyl-hexahydro-rel-(3aS,6aS)-pyrrolo[3,2-b]pyrrol-1-yl)-10-oxo-decanal A stirred solution of Intermediate 88 (1.28 g), in dry dichloromethane (45 ml) was cooled to −78° C. Dry ozone was passed through the solution until a deep blue colour persisted. Oxygen was bubbled through the solution for 5 minutes, followed by nitrogen for 5 minutes. Triphenylphosphine (1.63 g) was added and the solution stirred under nitrogen overnight. The solvent was removed in vacuo and the residue purified by flash chromatography, eluting with diethylether to give the title compound as a white solid (850 mg). T.l.c SiO$_2$ (Diethylether) R.f.=0.31.

Intermediates 90–91

The above Intermediates were prepared in a similar manner to Intermediate 89 from Intermediate 26.

rel-4-(4-Methanesulfonyl-5-oxo-6R-propyl-hexahydro-(3aS,6aR)-pyrrolo[3,2-b]pyrrol-1-yl)-6-oxo-hexanal Tlc (Ether:Ethyl acetate; 4:1) Rf 0.18. (Intermediate 90)

rel-4-(4-methanesulfonyl-5-oxo-6R-propyl-hexahydro-(3aS,6aR)-pyrrolo[3,2-b]pyrrol-1-yl)-4-oxo-butyraldehyde Mass spec. (found) MH$^+$=331, (calc) MH$^+$=331. (Intermediate 91)

Intermediate 92 rel-(3R,3aR,6aS)-4-Acryloyl-1-methanesulfonyl-3-propyl-hexahydro-pyrrolo[3,2-b]pyrrol-2-one A solution of 3-bromopropionyl chloride (140 mg) in dichloromethane (1 ml) was added dropwise to a stirred solution of Intermediate 26 (158 mg) and triethylamine (202 mg) in dichloromethane (15 ml). The mixture was stirred at room temperature for 4.5 hours, washed with 8% sodium bicarbonate (15 ml), 0.5 m hydrochloric acid (15 ml) and water (10 ml), dried (Na$_2$SO$_4$), filtered and concentrated in vacuo to give the title compound (161 mg) as a white powder. m.p. 177–181° Mass spec MH$^+$ (found)=301 MH$^+$ (calculated)=301 Microanalysis found: C, 50.1; H, 6.5; N, 8.75; S,10.2 C$_{13}$H$_{20}$N$_2$O$_{4S}$. requires: C, 50.2; H, 6.9; N, 9.0; 5, 10.3%.

Intermediates 93–94

The above Intermediates were prepared in a similar manner to Example 29, from Intermediate 26.

[2-(4-Methanesulfonyl-5-oxo-6R-propyl-hexahydro-(3aS,6aR)-pyrrolo[3,2-b]pyrrol-1-yl)-2-oxo-ethyl]-carbamic acid tert-butyl ester Mass spec. (found) MH$^+$404, (calc.) MH$^+$=404. (Intermediate 93)

rel-[2-(4-Methanesulfonyl-5-oxo-6R-propyl-hexahydro-(3aS,6aR)-pyrrolo[3,2-b]pyrrol-1-yl)-2-oxo-ethyl]methyl-carbamic acid tert-butyl ester Mass spec. (found) MH$^+$=418, (calc.) MH$^+$=418. (Intermediate 94)

Intermediate 95

(1-Ethoxy-3-methyl-but-1-enyloxy)-triisopropyl-silane

Tetrahydrofuran (100 ml) and 1,3-dimethyl-3,4,5,6-tetrahydro 2 (1H)-pyrimidinone (140 ml) were mixed at −20° C. and lithium bis (trimethylsilyl) amide (1M in tetrahydrofuran, 100 ml) was added. The mixture was cooled to −70° C., ethyl isovalerate (18.75 ml) added and stirred for ½ hour at −70° C. Triisopropylsilyl trifluoromethane sulfonate was added and the mixture left to stir at −75° C. for ½ hour before warming to room temperature and stirring for 3 hours. The reaction mixture was quenched with aqueous sodium bicarbonate (8%, 150 ml) and extracted with hexane (1000 ml). The hexane extract was washed with water (4×500 ml), dried (MgSO$_4$), filtered and concentrated in vacuo to afford a crude yellow oil containing the title compound.

Purification by vacuum short path distillation (2.0×10$^{-2}$ mbar, 68–80° C.) gave the title compound as a colourless oil (15.69 g). Boiling point range at 2.0×10$^{-2}$ mbar, 68–80° C.

Intermediate 96

2R-(2,2,2-Trifluoro-acetylamino)-succinamic acid

To a stirring suspension of D-Asparagine (37.9 g, powdered and dried at 110° C. for 48 hrs) in methanol (144 ml, dried over 3A sieves for 5 hours) under an atmosphere of nitrogen was added triethylamine (40.2 ml) followed by methyl trifluoroacetate (36 ml). The resulting mixture was left to stir for 48 hrs. To the reaction mixture was added dry methanol (145 ml) then Dowex 50 resin H$^+$ form (115 g, dried at 56° C. for 24 hours). The resultant mixture was stirred for 10 minutes, filtered and the solvent removed in vacuo to give a crude white solid containing the title compound. This crude product was combined with crude product from a similar experiment and recrystallised from hot water to afford the title compound as a white crystalline solid (106 g). Mass spec $MNH_4^+$ (found) 246 $MNH_4^+$ (calculated) 246.

Intermediate 97

2R-(2,2,2-Trifluoro-acetylamino)-succinamic acid methyl ester

A stirring solution of Intermediate 96 (95.14 g) in Methanol (1150 ml, dried over 3A molecular sieves) was cooled to −70° C. Acetyl chloride (162 ml) was slowly added whilst maintaining the reaction temperature below −60° C. The reaction mixture was allowed to warm to −20° C. and was left for 48 hours at this temperature. The solvent was removed in vacuo to give a clear and colourless oil containing the title compound. This was triturated with diethyl ether and the resultant white solid was recrystallised from boiling water to afford the title compound as a white crystalline solid (42 g). Mass spec $MH^+$ (found) 243 $MH^+$ (calculated) 243.

Intermediate 98

3-Cyano-2R-(2,2,2-trifluoro-acetylamino)-propionic acid methyl ester

To a stirring suspension of Intermediate 97 (3.0 g) in dichloromethane (20 ml) was added pyridine (4.92 ml) and p-toluene sulfonyl chloride (4.92 g). More dichloromethane (15 ml) was added and the brown solution left to stir at room temperature for 48 hours. The reaction mixture was diluted with dichloromethane (25 ml), washed with 1M aqueous $H_3PO_4$ (74 ml), dried ($Na_2SO_4$) filtered and the solvent removed in vacuo to give a crude brown solid (3.57 g) containing the title compound. The crude mixture was purified by flash chromatography ($SiO_2$, Merck, 9385) eluting with 1:3 then 1:2½ ethyl acetate:cyclohexane. The eluent was evaporated in vacuo to give the title compound as a white crystalline solid (1.62 g). T.L.C (1:1 Ethyl acetate:cyclohexane) Rf 0.5 Mass spec $MNH_4^+$ (found) 242 $MNH_4^+$ (calculated) 242.

Intermediate 99

2,2,2-Trifluoro-N-(2-oxo-pyrrolidin-3R-yl)-acetamide

A solution of Intermediate 98 (200 mg) in ethanol (10 ml) was stirred under an atmosphere of hydrogen gas with 5% Rhodium on alumina (1.00 g) for 3 hours. The catalyst was removed by filtration and the filtrate concentrated in vacuo to afford a crude gum containing the title compound. The mixture was purified by flash chromatography ($SiO_2$, Merck, 9385) eluting with acetonitrile. The eluent was evaporated in vacuo to afford the title compound as a white solid (40 mg). T.L.C (Acetonitrile) Rf 0.63 Mass spec $MNH_4^+$ (found) 214 $MNH_4^+$ (calculated) 214.

Intermediate 100

2-Oxo-3R-(2,2,2-trifluoro-acetylamino)-pyrrolidine-1-carboxylic acid benzyl ester To a stirring solution of Intermediate 99 (1.04 g) in tetrahydrofuran cooled to −70° C., was added n-butyl lithium (1.6M in hexanes, 3.31 ml). After 5 minutes benzylchloroformate (833 μl) was added and the reaction mixture was allowed to warm to room temperature. After 2½ hours the reaction mixture was diluted with ethyl acetate (100 ml) and washed with 1M hydrochloric acid (2×150 ml). The combined organic extracts were dried ($MgSO_4$), filtered and concentrated in vacuo to give a crude orange/white solid which was purified by trituration with diethyl ether to afford the title compound as a white solid (1.25 g). Mass spec $MNH_4^+$ (found) 348 $MNH_4^+$ (calculated) 348 Chiral HPLC (Chiracel AD, eluent system ethanol:heptane 15:85, flow rate=1 ml/min). Retention time of R enantiomer=10.08 min (71.8%). Retention time of S enantiomer=12.50 min (28.2%)

Intermediate 100. (Alternative Synthesis)

2-Oxo-3R-(2,2,2-trifluoro-acetylamino)-pyrrolidine-1-carboxylic acid benzyl ester Intermediate 155 (195.5 g) was suspended in dichloromethane (1500 ml) and methanol (600 ml), added. Methyl trifluoroacetate (410 g) was added followed by N-methylmorpholine (97 g). The reaction mixture was allowed to stir at room temperature for 18 h. The reaction mixture was diluted with dichloromethane (500 ml) and saturated ammonium chloride (1000 ml) added. Dilute hydrochloric acid solution (2N, 250 ml) was added and the mixture stirred vigorously for 5 min and then allowed to separate. The organic layer was separated and the aqueous extracted with dichloromethane (500 ml). The organic extracts were combined and washed with dilute HCl (2N, 1000 ml), brine (1000 ml), dried ($Na_2SO_4$) and concentrated. The residue was triturated with ether:cyclohexane (1:1, 1000 ml) and the solid filtered to give the title compound as a pale pink solid (197.9 g). Tlc (ether) Rf=0.46 Mass spec:$MNH_4^+$ (found)=348 $MNH_4^+$ (calc)=348.

Intermediate 101

2-Ethoxy-3R-(2,2,2-trifluoro-acetylamino)-pyrrolidine-1-carboxylic acid benzyl ester Intermediate 100 (100 mg) was dissolved in dry tetrahydrofuran (1 ml), cooled to −20° C. and lithium borohydride (2.0M in THF, 0.15 ml) added. After ½ hour ethanol (1 ml) was added followed by concentrated $H_2SO_4$ (33 μl) and the resultant stirring solution was left at room temperature for 3½ hours. The reaction mixture was adjusted to pH8–9 by addition of saturated aqueous sodium bicarbonate and the organic solvents were removed in vacuo. The resultant residue was partitioned between ethyl acetate (20 ml) and water (10 ml) and the acqueous phase extracted with further ethyl acetate (10 ml). The combined organic layers were dried ($Na_2SO_4$), filtered and concentrated in vacuo to afford the title compound as a clear oil (101 mg) which was used without further purification. Mass Spec. $MNH_4^+$ (found) 378 $MNH_4^+$ (calculated) 378

Intermediate 101. (Alternative Synthesis)

2-Ethoxy-3R-(2,2,2-trifluoro-acetylamino)-pyrrolidine-1-carboxylic acid benzyl ester A solution of Intermediate 100 (214.8 g) in dry THF (1200 ml) was stirred and cooled to −30° C. Lithium borohydride (2.0M in THF, 336 ml) was added (after an initial temperature rise to −12° C., the temperature was maintained below −17° C. throughout the addition). The mixture was stirred at −20° C. for 90 minutes before ethanol (760 ml) was added to the mixture whilst maintaining the temperature below −19° C. A cooled mixture of concentrated sulphuric acid (75 ml) in ethanol (215 ml) was slowly added to the mixture whilst maintaining the internal temperature below −18° C. The cooling bath was removed and the reaction left to stir for 90 minutes, whereupon the internal temperature had risen to +15° C. A saturated solution of sodium bicarbonate (1600 ml) was carefully added to the mixture over 35 min before removal of the volatiles in vacuo. The residual aqueous phase was extracted with ethyl acetate (1000 ml+2×800 ml)

the combined extracts washed with brine (800 ml), dried (Na$_2$SO$_4$) overnight and the solvent removed in vacuo to give the title compound (211.6 g) as an orange oil. Tlc (4:1; CH$_2$Cl$_2$:Et$_2$O) Rf 0.64 and 0.43.

Intermediate 102
(2S,3R)-2-(rel-1S-Ethoxycarbonyl-2-methyl-propyl)-3-(2,2,2-trifluoro-acetylamino)-pyrrolidine-1-carboxylic acid benzyl ester Intermediate 101 (90 mg), Intermediate 95 (0.22 g) and dichloromethane (1.1 ml) were cooled to 5° C. and boron trifluoride dietherate (0.15 ml) added. After 55 min the reaction was quenched with 2M aqueous sodium bicarbonate (15 ml) and diluted with dichloromethane (10 ml). The aqueous layer was separated and the organic layer was washed with a saturated aqueous solution of sodium chloride (10 ml). The organic extract was dried (MgSO$_4$), filtered and concentrated in vacuo to afford the title compound as a colourless oil (106 mg). Mass spec MH$^+$ (found) 445 MH$^+$ (calculated) 445

Intermediate 102. (Alternative Synthesis)
(2S,3R)-2-(rel-1S-Ethoxycarbonyl-2-methyl-propyl)-3-(2,2,2-trifluoro-acetylamino)-pyrrolidine-1-carboxylic acid benzyl ester Intermediate 101 (97.9 g), (Z)-(1-ethoxy-3-methyl-but-l-enyloxyl-triisopropylsilane) (233 g) and dichloromethane (600 ml) were cooled to 5° C. under nitrogen and boron trifluoride diethyl etherate (200 ml) added over 15 minutes. After a further 15 minutes, 2M sodium carbonate (750 ml) was added, keeping the temperature below 20° C. The reaction mixture was filtered through Hyflo and the solid material washed with dichloromethane (2×200 ml). After adding the washes to the 2-phase mixture the aqueous layer was separated and extracted with dichloromethane (2×400 ml). The combined extracts were washed with brine (2×250 ml), dried (MgSO$_4$) and concentrated in vacuo to give the title compound contaminated with some of Intermediate 103 (154 g). Tlc SiO$_2$ (1:3; ethyl acetate:cylcohexane) Rf=0.49 (β-anomer), 0.42 (α-anomer). Mass spec. (found) MH$^+$=445 (calc) MH$^+$=445.

Intermediate 103
(2S,3R)-3-Amino-2-(1-ethoxycarbonyl-2-methyl-propyl)-pyrrolidine-1-carboxylic acid benzyl ester Intermediate 102 (97 mg), potassium carbonate (300 mg), ethanol (2 ml) and water (2 ml) were warmed at reflux for 2¼ hours. The ethanol and water were evaporated in vacuo and the residue was partitioned between ethyl acetate (10 ml) and water (10 ml). The aqueous extract was taken to pH9–10 by addition of 2M aqueous sodium hydroxide solution and extracted with diethyl ether (3×20 ml). The combined organic extracts were dried (MgSO$_4$), filtered and concentrated in vacuo to afford the title compound as a clear oil (56 mg).

Intermediate 103 (Alternative Synthesis)
(2S,3R)-3-Amino-2-(1-ethoxycarbonyl-2-methyl-propyl)-pyrrolidine-1-carboxylic acid benzyl ester Intermediate 102 (contaminated with some Intermediate 103) (1539), potassium carbonate (183.3 g), ethanol (1000 ml) and water (1000 ml) were refluxed together for 5 h. The organic layer was then separated and concentrated in vacuo. The residue, the aqueous layer and brine (200 ml) were extracted with ether (2×500 ml, +250 ml) and the combined extracts extracted with 1M hydrochloric acid (3×500 ml). The combined acidic extracts were then taken to pH8 with solid sodium hydrogen carbonate (150 g) and extracted with dichloromethane (600 ml, +3×300 ml). The combined dichloromethane extracts were dried (MgSO$_4$) and concentrated in vacuo to afford the title compound (87.9 g). Tlc SiO$_2$ (100:8:1 dichloromethane:ethanol:ammonia) Rf=0.55 Mass spec (found) MH$^+$=349 (calc) MH$^+$=349.

Intermediate 104
(3aR,6S,6aS)-6-Isopropyl-5-oxo-hexahydro-pyrrolo[3,2-b]pyrrole-1-carboxylic acid benzyl ester Intermediate 103 (50 mg) was dissolved in tetrahydrofuran (1 ml) and tetramethylethylenediamine (1 ml) then 1M t-butylmagnesium chloride in tetrahydrofuran (0.4 ml) added. After 3 hours the reaction was quenched with saturated ammonium chloride solution (1 ml). The acqueous layer was separated and extracted with ethylacetate (4 ml). The combined organic extracts were evaporated in vacuo. The residue was partitioned between dichloromethane (10 ml) and 2M hydrochloric acid (10 ml). The aqueous phase was separated and extracted with dichloromethane (3×5 ml). The combined organic extracts were dried (MgSO$_4$), filtered and concentrated in vacuo to give a crude white solid containing the title compound. Purification by flash chromatography (SiO$_2$, Merck, 9385) eluting with 1:1 ethyl acetate:cyclohexane afforded the title compound as a white solid (16 mg). T.L.C (2:1 ethyl acetate:cyclohexane) Rf 0.38 Chiral HPLC (chiracel AD Column, eluent system ethanol:heptane 10:90, flow rate 1 ml/min). Retention time of SSR lactam=9.92 min (73.6%). Retention time of RRS lactam= 13.12 min (26.4%).

Intermediate 104 (Alternative Synthesis)
(3aR,6S,6aS)-6-Isopropyl-5-oxo-hexahydro-pyrrolo[3,2-b]pyrrole-1-carboxylic acid benzyl ester To Intermediate 103 (87 g), tetrahydrofuran (800 ml), N,N,N',N'-tetramethylethylenediamine (800 ml) at 0° C. under nitrogen was added 1M t-butylmagnesium chloride in tetrahydrofuran (750 ml) over 40 min. After a further 1 h, saturated ammonium chloride solution (500 ml) was added and the aqueous layer separated and extracted with ethyl acetate (250 ml). The combined organic layers were then concentrated in vacuo. To the residue was added 1M hydrochloric acid (1000 ml) and this was extracted with ethyl acetate (3×500 ml). The combined extracts were washed with brine (250 ml), dried (MgSO$_4$) and concentrated in vacuo to give a brown solid (63.4 g). This was recrystallised from ethyl acetate to afford the title compound (29.5 g). Tlc SiO$_2$ (19:1 ethyl acetate:methanol) Rf=0.64 Mass spec (found) MH$^+$=303 (calc) MH$^+$=303.

Intermediate 105
(2S,3R)-3-tert-Butoxycarbonylamino-2-(1S-ethoxycarbonyl-but-3-enyl)-pyrrolidin-1-carboxylic acid benzyl ester A solution of lithium bis (trimethylsilyl) amide (LHMDS) in tetrahydrofuran (THF) (1M 40 ml) was added dropwise to a stirred solution of Intermediate 63 (16.1 3 g) in a dry tetrahydrofuran (86 ml) 1:3dimethyl-3,4,5,6-tetrahydro-2H-(1H)-pyrimidone (200 ml) mixture at −51° C. under nitrogen. The mixture was then cooled to −64° C. and more LHMDS in THF (1M, 88 ml) was added dropwise. After 80 minutes at 65° C. allyl iodide (4.5 ml) was added dropwise and stirring at −67° C. under nitrogen was continued for a further 3 h. The reaction was quenched cold by the addition of 50% saturated acqueous ammonium chloride (64 ml) and extracted with ethyl acetate. The ethyl acetate extracts were combined and concentrated in vacuo. The residue was dissolved in toluene and the resulting solution was washed with water and saturated brine, dried (MgSO$_4$) and concentrated in vacuo to give a yellow orange oil. The oil was purified by flash column chromatography on silica with hexane:ethyl acetate (7:3) as eluent. Concentration of the appropriate fractions gave the title compound (6.2 g) as a yellow oil. Tlc Silica (Hexane:ethyl acetate; 7.3) Rf=0.26.

Intermediate 106
(2S,3R)-3-Amino-2-(1S-ethoxycarbonyl-but-3-enyl)-pyrrolidine-1-carboxylic acid benzyl ester Intermediate 105 (14.5 g) was dissolved in a solution of hydrogen chloride in dioxan (4M, 70 ml) and the resulting solution was stirred at room temperature for 3 h. The mixture was concentrated in vacuo and the resulting oil was dissolved in water. The acqueous solution was washed with ether then basified with acqueous sodium bicarbonate (1M, 50 ml) and extracted with ethyl acetate. The ethyl acetate solution was dried ($Na_2SO_4$) and concentrated in vacuo to give the title compound (11.1 g) as a yellow oil. Tlc Silica (Ethyl Acetate:Hexane; 1:1) Rf=0.07 Mass spec $MH^+$ (found) 347 $MH^+$ (calculated) 347.

Intermediate 107
(3aS,6R,6aR)-6-Allyl-4-methanesulfonyl-5-oxo-hexahydro-pyrrolo[3,2-b]pyrrole-1-carboxylic acid benzyl ester A solution of Intermediate 67 (500 mg) in dry tetrahydrofuran (30 ml) was stirred under nitrogen at −70° C. Lithium bis(trimethylsilyl)amide—1M in tetrahydrofuran (2.16 ml) was added and the mixture allowed to stir for 5 min before the cooling bath was replaced by an ice/water bath, and the mixture stirred at ~0° C. for 30 min. The mixture was recooled to −70° C., and methane sulphonyl chloride (322 ml) added. The reaction mixture was stirred for a further 1¾ h before sat. $NH_4Cl$ (5 ml) was added and the mixture allowed to warm to room temperature. The mixture was partitioned between ethyl acetate (60 ml) and water (20 ml) and the aqueous phase further extracted with EtOAc (2×40 ml). The combined organic phases were washed with brine (20 ml), dried ($MgSO_4$), filtered and the solvent removed in vacuo to give a yellow oil. The oil was purified by flash column chromatography using silica gel and eluted with 1:1 ethyl acetate/n-hexane to give the title compound as a colourless solid (275 mg). T.l.c. (Silica plate, 1:1 EtOAc/n-Hexane), Rf=0.27.

Intermediate 108
(3R,3aR,6aS)-1-Methanesulfonyl-3-propyl-hexahydro-pyrrolo[3,2-b]pyrrol-2-one A solution of Intermediate 107 (413 mg) in ethyl acetate (50 ml) was hydrogenated at room temperature and 1 atm pressure over moist 20% palladium hydroxide on carbon (300 mg) for 9 h. The catalyst was filtered off using 'hyflo' filter aid and the filter plug washed with ethyl acetate. The combined organics were concentrated in vacuo to give the title compound as a colourless solid (265 mg). Circular Dichroism C=1.5×10$^{-4}$M in MeCN path length 0.5 cm, δE=−6.67 @ 195.2 nm T.l.c. (Silica plate, Methanol/Dichloromethane 3:7) Rf=0.66.

Intermediate 109
(3aR,6S,6aS)-6-Allyl-4-methanesulfonyl-5-oxo-hexahydro-pyrrolo[3,2-b]pyrrole-1-carboxylic acid benzyl ester Intermediate 68 (300 mg) was dissolved in tetrahydrofuran (20 ml) and cooled to −70° C. (acetone/dry ice bath) under nitrogen. Lithium bis(trimethylsilyl)amide, 1M in tetrahydrofuran (1.3 ml) was added and the mixture allowed to stir at −70° C. for 6 min. The $CO_2$/acetone bath was replaced with a water/ice bath and the mixture allowed to warm to 0° C. Stirring was continued for a further 30 min before the reaction was re-cooled to −70° C. and methane sulphonyl chloride (195 ml) was added and the reaction allowed to stir at −70° C. for 4 h. The reaction was quenched with ammonium chloride (5 ml) and allowed to warm to room temperature. Water (20 ml) was added and the mixture was extracted with ethyl acetate (40 ml and 2×20 ml). The combined organic extracts were dried ($MgSO_4$), filtered and concentrated in vacuo to give a pale yellow oil (434 mg). This was purified by flash column chromatography on silica gel using ethyl acetate:hexane (1:1) as eluent, to give the title compound as a white solid (140 mg). T.l.c. (silica plate, ethyl acetate:hexane 1:1), Rf=0.31 $α_D^{20}$=+53.3 (c=5, EtOH).

Intermediate 110
(3S,3aS,6aR)-1-Methanesulfonyl-3-propyl-hexahydro-pyrrolo[3,2-b]pyrrol-2-one Intermediate 109 (127 mg) in ethyl acetate (15 ml) was added to 20% moist palladium hydroxide on carbon (62 mg) and the resulting suspension stirred under hydrogen for 5 h. The mixture was filtered through 'hyflo' filter-aid and the filtrate concentrated in vacuo to give the title compound as an off-white solid (89 mg). Circular Dichroism: c=1.16×10$^{-4}$M in MeCN path length=0.5 cm δE=+5.81 at 193.2 nm T.l.c. (Silica plate, Methanol/Dichloro-methane 3:7) Rf=0.66.

Intermediates 104 and 111

A racemic sample of Intermediate 84 (1.40 g) was separated into its enantiomers by chiral HPLC (2 inch Merck Column with chiralpak AD solid phase, eluent system 15% ethanol/heptane, flowrate=50 ml min$^{-1}$) to give:

Intermediate 104
(3S, 3aS, 6aR)-6-isopropyl-5-oxo-hexahydro-pyrrolo[3,2-b] pyrrole-1-carboxylic acid benzyl ester (510 mg)
Chiral HPLC (chiracel AD, eluent system ethanol:heptane 10:90, flowrate 1 ml/min) Retention time=9.0 min, 98.9% e.e.

Intermediate 111
(3R, 3aR, 6aS)-6-Isopropyl-5-oxo-hexahydro-pyrrolo[3,2-b]pyrrole-1-carboxylic acid benzyl ester (495 mg)
Chiral HPLC (system as for intermediate 104). Retention time=11.3 min, 97.8% e.e.

Intermediate 112
(E)-4-Piperidin-1-yl-but-2-enoic acid ethyl ester

A mixture of ethyl bromocrotonate (193 mg), piperidine (94 mg) and potassium carbonate (276 mg) in acetonitrile (10 ml) was stirred and heated at reflux for 3 hours. The reaction mixture was cooled and the solvent was removed in vacuo. The residue was partitioned between water (2×15 ml) and ethyl acetate (20 ml). The organic extracts were dried ($Na_2SO_4$), filtered and concentrated in vacuo to give the title compound as an orange oil (157 mg). Tlc Silica. (100:8:1) Mixture of dichloromethane, ethanol and ammonia (S.G= 0.88) Rf=0.55 Mass spec $MH^+$ (found)=198 $MH^+$ (calculated)=198.

Intermediate 113
(E)-4-Piperidin-1-yl-but-2-enoic acid hydrochloride

A solution of Intermediate 112 (592 mg) in dioxan (18 ml) and 2M hydrochloric acid (10 ml) was stirred and heated at reflux for 5.5 hours. The reaction mixture was cooled and the solvents were removed in vacuo, using toluene to remove

Intermediate 114
rel-(3R,3aR,6aS)-4-(4-Chloro-but-2E-enoyl)-1-methanesulfonyl-3-propyl-hexahydro-pyrrolo[3,2-b]pyrrol-2-one A solution of Intermediate 26 (40 mg) in dry tetrahydrofuran (1 ml) was added to a stirred solution of Intermediate 116 (50 mg), 1-hydroxybenzotriazole (43 mg) and 1-(3-dimethylaminopropyl)-3-ethylcarbodiimide hydrochloride (61 mg) in dry tetrahydrofuran (2.5 ml) and dimethylformamide (0.5 ml). The reaction mixture was stirred at room temperature for 2.5 hours and then partitioned between 4% sodium bicarbonate (15 ml) and ethyl acetate (2×20 ml). The combined organics were washed with water (2×15 ml), dried $Na_2SO_4$), filtered and concentrated to leave a gum. The gum was purified by flash column chromatography on silica, eluting with a (4:3) mixture of ethyl acetate and cyclohexane, to give the title compound as a cream powder (25 mg). Tlc Silica. (1:1) Mixture of cyclohexane and ethyl acetate Rf=0.22 Mass spec $MH^+$ (found)=349 $MH^+$ (calculated)=349.

Intermediate 115
rel-(3R3aR,6aS)-4-[3-(4-Methanesulfonyl-5-oxo-6-propyl-hexahydro-pyrrolo[3,2-b]pyrrol-1-yl)-3-oxo-prop-2E-enyl]-benzaldehyde A solution of Intermediate 26 (60 mg) in dry dimethylformamide (0.8 ml) was added to a stirred solution of 4-formylcinnamic acid (56 mg), 1-hydroxybenzotriazole (44 mg) and 1-(3-dimethylaminopropyl)-3-ethylcarbodiimide hyrochloride (62 mg) in dry dimethylformamide (2.7 ml). The reaction mixture was stirred at room temperature for 16 hours then partitioned between 8% sodium bicarbonate (15 ml) and ethyl acetate (20 ml). The ethyl acetate phase was separated, washed with water (2×15 ml), dried ($Na_2SO_4$), filtered and evaporated to give a solid. The solid was triturated in ether (10 ml) for 10 min. The ether was decanted. The residue was dried in vacuo to give the title compound as a yellow powder (79 mg). Melting point 183–188° Mass spec $MH^+$ (found)=405 $MH^+$ (calculated)=405.

Intermediate 116
4-Chloro-but-2E-enoic acid

A solution of ethyl-4-bromocrotonate (3.58 g) and lithium hydroxide monohydrate (0.83 g) in water (30 ml) and tetrahydrofuran (50 ml) was stirred at room temperature for 5.5 hours, acidified (to pH 1–2) with 2M hydrochloric acid (13 ml) and extracted with ethyl acetate (2×50 ml). The combined organics were washed with water (40 ml), dried ($Na_2SO_4$), filtered and concentrated to give a viscous oil. The oil was triturated in dichloromethane (10 ml) for 5 min. The solution was decanted and concentrated to leave an oil. The oil was triturated in diethyl ether (15 ml) for 10 min. The solution was decanted and concentrated to give a semi-solid. Purification by flash column chormatography on silica, eluting with a (3:2) mixture of cyclohexane and ethyl acetate, gave the title compound as a waxy, white solid (0.62 g). Tlc Silica. (1:1) Mixture of cyclohexane and ethyl acetate. Rf=0.5.

Intermediate 117
rel-(3R,3aR,6aS)-4-(4-Chloro-but-2E-enoyl)-3-isopropyl-1-methanesulfonyl-hexahydro-pyrrolo[3,2-b]pyrrol-2-one A solution of Intermediate 86 (690 mg), Intermediate 116 (500 mg), 1-hydroxybenzotriazole (541 mg) and ethyl-1-(3-dimethylaminopropyl)-3-ethylcarbodiimide hydrochloride (766 mg) in dry dimethylformamide (5 ml) and dry tetrahydrofuran (20 ml) was stirred at room temperature for 6 hours, then left to stand for a further 16 hours. The reaction mixture was partitioned between ethyl acetate (2×75 ml) and 8% sodium bicarbonate (80 ml). The combined ethyl acetate extracts were washed with 0.5M. hydrochloric acid (2×60 ml) and water (60 ml), dried ($Na_2SO_4$) and evaporated to give a semi-solid, which was purified by flash column chromatography on silica, using a mixture of cyclohexane and ethyl acetate (initially 2:1, gradually increasing the concentration of ethyl acetate to give a 1:1 mixture), to give the title compound as a white powder (328 mg). Tlc Silica (1:1) Mixture of cyclohexane and ethyl acetate. Rf=0.3 Mass spec $MH^+$ (found)=349 $MH^+$ (calculated)=349 (also isolated from the experiment was Intermediate 118).

Intermediate 118
rel-(3R,3aR,6aS)-4-(4-Chloro-but-3Z-enoyl)-3-isopropyl-1-methanesulfonyl-hexahydro-pyrrolo[3,2-b]pyrrol-2-one Intermediate 118 was isolated as a second component from the purification by flash column chromatography of Intermediate 117 (see above). The title compound was isolated as a white powder (284 mg). Melting point 165–167° C. Tlc Silica. (1:1) Mixture of cyclohexane and ethyl acetate. Rf=0.55 Mass spec $MH^+$ (found)=349 $MH^+$ (calculated)=349.

Intermediate 119

The above Intermediate was prepared in a similar manner to Intermediate 112.

(E)-4-Azepin-1-yl-but-2-enoic acid ethyl ester

Mass spec.(found) $MH^+$=212, (calc)=212.

Intermediate 120

The above Intermediate was prepared in a similar manner to Intermediate 113 from Intermediate 119.

(E)-4-Azepin-1-yl-but-2-enoic acid

Mass spec.(found) $MH^+$=184, (calc)=184.

Intermediate 121
(3aR,6S,6aS)-6-Isopropyl-4-methanesulfonyl-5-oxo-hexahydro-pyrrolo[3,2-b]pyrrole-1-carboxylic acid benzyl ester To Intermediate 104 (0.46 g) in dry tetrahydrofuran (30 ml) at −70° C. under nitrogen was added 1M lithium hexamethyidisilazide in tetrahydrofuran (2.0 ml). The solution was warmed to 0° C. for 15 minutes and then recooled to −70° C. when methane sulphonyl chloride (0.30 ml) was added. After 1.5 hours, saturated aqueous ammonium chloride was added (30 ml) and the mixture extracted with ethyl acetate (3×5 ml). The combined extracts were washed with brine (2×25 ml), dried ($MgSO_4$) and the solvent removed in vacuo. Flash chromatography of the residue on silica with 1:1 ethyl acetate:cyclohexane gave the title compound as a white solid (0.34 g). T.l.c $SiO_2$ (1:1 ethyl acetate:cyclohexane) Rf 0.4 Mass spec $MNH_4^+$ (found)=398 $MNH_4^+$ (calculated)=398.

Intermediate 122
(3S,3aS,6aR)-3-Isopropyl-1-methanesulfonyl-hexahydro-pyrrolo[3,2-b]pyrrol-2-one Intermediate 121 (0.31 g), 10% palladium hydroxide on carbon (0.24 g) 1,4-dioxan (25 ml) and ethyl acetate (25 ml) were mixed under hydrogen for 3 hours.

The catalyst was then removed by filtration through hyflo and the filtrate concentrated in vacuo to afford the title compound as a pale yellow solid (0.20 g). T.l.c. $SiO_2$(9:1 chloroform:methanol) Rf=0.36 Mass spec $MH^+$ (found)= 247 $MH^+$ (calculated)=247.

Intermediate 123
(3aS,6R,6aR)-6-Isopropyl-4-methanesulfonyl-5-oxo-hexahydro-pyrrolo[3,2-b]pyrrole-1-carboxylic acid benzyl ester To Intermediate 111 (0.46 g) in dry tetrahydrofuran (30 ml) at −75° C. under nitrogen was added 1M lithium hexamethyldisilazide in tetrahydrofuran (2.0 ml). The solution was stirred for 5 minutes before being warmed to 0° C. for 25 minutes and then recooled to −75° C. when methane sulphonyl chloride (0.30 ml) was added. After 4.5 hours, saturated aqueous ammonium chloride was added (5 ml) and the mixture allowed to warm to room temperature. Water (15 ml) was added and the mixture extracted with ethyl acetate (3×20 ml). The combined extracts were washed with water (10 ml) and brine (15 ml), dried ($MgSO_4$) and the solvent removed in vacuo. Flash chromatography of the residue on silica with 1:1 ethyl acetate:cyclohexane gave the title compound as a white solid (0.4 g). T.l.c. $SiO_2$ (1:1 ethyl acetate:cyclohexane) Rf 0.4 Mass spec $MNH_4^+$ (found)=398 $MNH_4^+$ (calculated)=398 $MH^+$ (found) 381 $MH^+$ (calculated)=381.

Intermediate 124
(3R,3aR,6aS)-3-Isopropyl-1-methanesulfonyl-hexahydro-pyrrolo[3,2-b]pyrrol-2-one Intermediate 123 (0.37 g), 10% palladium hydroxide on carbon (0.11 g) and ethyl acetate (50 ml) were mixed under hydrogen for 5 hours. The catalyst was then removed by filtration through hyflo and the filter cake washed with ethyl acetate (3×20 ml) and hot ethyl acetate (40 ml). The combined filtrates were concentrated in vacuo to afford the title compound as a white crystalline solid (0.23 g). T.l.c. $SiO_2$ (Ethyl Acetate) Rf=0.07 Mass spec $MH^+$ (found)=247 $MH^+$ (calculated)=247.

Intermediate 125
trans-3-tert-Butoxycarbonylamino-2-(hydroxy-methoxycarbonyl-methyl)-pyrrolidine-1-carboxylic acid benzyl ester A solution of potassium hexamethyldisilazide in toluene (0.5M; 25.5 ml) was added in a stream, using a syringe, to a stirred solution of Intermediate 9 (2.50 g) in dry tetrahydrofuran (40 ml) at −78°, under nitrogen. The reaction mixture was stirred at −78° for 1 hour then treated, in a stream over 5 minutes, with a solution of 3-phenyl-2-(phenylsulphonyl) oxaziridine (3.33 g) in dry tetrahydrofuran (25 ml). The reaction mixture was stirred at −78° for a further 2 hours, quenched with saturated ammonium chloride (30 ml) and warmed to room temperature. Ethyl acetate (60 ml) was added, with vigorous stirring. The organic phase was separated, washed with water (30 ml), dried ($Na_2SO_4$), filtered and concentrated in vacuo to give a yellow oil. Purification by flash column chromatography on silica eluting with a mixture of cyclohexane and ethyl acetate (initially 2:1, gradually increasing the concentration of ethyl acetate to give a 1:1 solvent ratio) gave the title compound (approx. 1:1 mixture of α and β-isomers) as a white gum (2.48 g). Tlc Silica. (1:1) Mixture of cyclohexane and ethyl acetate. Rf=0.4–0.5 Mass spec $MH^+$ (found)=409 $MH^+$ (calculated)=409.

Intermediate 126
rel-(2S,3S)-tert-Butoxycarbonylamino-2-[(R)-methoxy-methoxycarbonyl-methyl]-pyrrolidine-1-carboxylic acid benzyl ester A mixture of Intermediate 125 (2.35 g), silver (I) oxide and iodomethane (10 ml) in acetonitrile (120 ml) was stirred and heated at reflux for 22 hours, more iodomethane (4 ml) being added after 4 hours. The reaction mixture was cooled and filtered through celite. The filtrate was concentrated in vacuo to give a yellow glass. Purification by flash column chromatography on silica, eluting with a mixture of cyclohexane and ethyl acetate (initially 3:1, gradually increasing the concentration of ethyl acetate to eventually give a 1:1 mixture) gave the title compound as a colourless glass (0.70 g). The corresponding α-anomer (0.95 g) was also isolated from this experiment. Tlc Silica. (1:1) Mixture of cyclohexane and ethyl acetate. Rf=0.47 Mass spec $MH^+$ (found)=423 $MH^+$ (calculated)=423.

Intermediate 127
rel-(2S,3S)-3-Amino-2-[(R)-methoxy-methoxycarbonyl-methyl]-pyrrolidine-1-carboxylic acid benzyl ester A solution of Intermediate 126 (680 mg) and 4.0 molar hydrogen chloride in dioxan (5 ml) was stirred at room temperature for 2.0 hours. The solvent was removed in vacuo and the residue was partitioned between ethyl acetate (30 ml) and 1.0 molar sodium carbonate (12 ml). The aqueous phase was separated and extracted with ethyl acetate (20 ml). The combined organic phases were dried ($Na_2SO_4$), filtered and concentrated in vacuo to give the title compound as a pale yellow gum (475 mg). Mass spec $MH^+$ (found)=323 $MH^+$ (calculated)=323.

Intermediate 128
rel-(3aS,6R,6aS)-6-Methoxy-5-oxo-hexahydro-pyrrolo[3,2-b]pyrrole-1-carboxylic acid benzyl ester A solution of tert. butylmagnesium chloride in tetrahydrofuran (1.0 Molar, 5.0 ml) was added in a stream to a stirred solution of Intermediate 127 (475 mg) in tetrahydrofuran (15 ml) at 0–5° (ice/water both cooling). The reaction mixture was stirred and warmed to 15° over 2 hours, then treated with saturated ammonium chloride (15 ml) and extracted with ethyl acetate (30 ml+20 ml). The combined organic extracts were dried ($Na_2SO_4$), filtered and concentrated in vacuo to give a gum. Purification by flash column chromatography on silica, eluting with ethyl acetate, gave the title compound as white crystals (168 mg). Tlc Silica. Ethyl acetate Rf=0.29 Mass spec $MH^+$ (found)=291 $MH^+$ (calculated)=291.

Intermediate 129
trans-3-tert-Butoxycarbonylamino-2-(methoxycarbonyl-methylsulfanyl-methyl)-pyrrolidine-1-carboxylic acid benzyl ester To a stirring solution of Intermediate 9 (3.97 g) in anhydrous tetrahydrofuran (15 ml) and anhydrous N,N,N,'N'-tetramethylethylenediamine (10 ml) at −55° C. under nitrogen was added 1M tert-butylmagnesium chloride in tetrahydrofuran (12 ml) followed by 1M lithium bis(trimethylsilyl)amide in tetrahydrofuran (40 ml) dropwise over 40 minutes. The resulting solution was left stirring at −55° C. for 0.5 hours, treated with methyl sulfide (5 ml) and, after reaching −26° C., cooled to −40° C. and glacial acetic acid (3 ml) added. The resulting mixture was allowed to warm to −10° C., diluted with ethyl acetate (300 ml) and washed successively with water (2×200 ml), 0.5M aqueous hydrochloric acid (200 ml) and brine (2×200 ml). The organic phase was dried ($Na_2SO_4$), filtered and concentrated in vacuo to a gum. Purification by column chromatography eluting with dichloromethane:ethyl acetate (85:15) resulted in fractions which were concentrated in vacuo to give the title compound (997 mg). Tlc (Dichloromethane:Ethyl Acetate 85:15) Rf 0.57.

Intermediate 130 trans-3-Amino-2-(methoxycarbonyl-methylsulfanyl-methyl)-pyrrolidine-1-carboxylic acid benzyl ester A solution of Intermediate 129 in 4M hydrogen chloride in 1,4-dioxane (9 ml) was left stirring at room temperature for 1 h. The reaction mixture was diluted with ethyl acetate (150 ml), washed with a saturated solution of aqueous sodium bicarbonate (100 ml) and brine (2×100 ml), then dried ($Na_2SO_4$), filtered and concentrated in vacuo to give the title compound as a clear oil (749 mg).

Intermediate 131 rel-(3aS,6R,6aS)-6-Methylsulfanyl-5-oxo-hexahydro-pyrrolo[3,2-b]pyrrole-1-carboxylic acid benzyl ester To a stirring solution of Intermediate 130 (725 mg) in anhydrous tetrahydrofuran (35 ml) at 0° C. under nitrogen was added 1M tert-butylmagnesium chloride in tetrahydrofuran (7 ml). The resulting mixture was left stirring at 0° C. for 2 h then treated with 2N aqueous hydrochloric acid (7 ml). The resultant was concentrated in vacuo to ca 1/3 volume, and extracted with ethyl acetate (100 ml). The organic extract was dried ($Na_2SO_4$), filtered and concentrated in vacuo to a gum. Purification by column chromatography eluting with ethyl acetate gave the title compound (112 mg). Mass spec $MH^+$ (found)=307 $MH^+$ (calc)=307.

Intermediate 132

The above Intermediate was prepared in a similar manner to Intermediate 115 from Intermediate 86.
rel-4-[3-(6R-Isopropyl-4-methanesulfonyl-5-oxo-hexahydro-(3aS,6aR)-pyrrolo[3,2-b]pyrrol-1-yl)-3-oxo-(E)-propenyl]-benzaldehyde Melting point=201–204° C. Mass spec. $MH^+$ (found)=405. $MH^+$ (calc.)=405.

Intermediate 133 rel-(3R,3aR,6aS)-4-(3-Piperidin-1-yl-propionyl)-3-propyl-hexahydro-pyrrolo[3,2-b]pyrrol-2-one A stirred solution of Intermediate 34 (1.213 g) and bromo-tris-pyrrolidino-phosphonium hexafluorophosphate (3.7 g) in dry dichloromethane (50 ml) under nitrogen had piperidine propionic acid (1.15 g) and N,N-diisopropylethylamine (3.8 ml) added. The mixture was stirred for 20 hours before the solvent was removed in vacuo to give a yellow/grey crystalline solid. The solid was purified by flash column chromatography eluting with 50:8:1 dichloromethane/ethanol/0.880 ammonia until the non-polar impurities eluted and thereafter with 25:8:1 $CH_2Cl_2$/EtOH/0.880 $NH_3$. The required fractions were combined and the solvent removed in vacuo to give the title compound as a white crunchy foam, yield=2.214 g. Tlc Silica plate, 50:8:1 $CH_2Cl_2$/EtOH/0.880$NH_3$ Rf=0.13 Mass spec $MH^+$ (found)=308 $MH^+$ (calculated)=308.

Intermediate 134

The above Intermediate was prepared in a similar manner to Intermediate 133 from Intermediate 34.
rel-(3R,3aR,6aS)-4-(6-Piperidin-1-yl-hexanoyl)-3-propyl-hexahydro-pyrrolo[3,2-b]pyrrol-2-one
mp. 78–79.5° C.

Intermediate 135

The above Intermediate was prepared in a similar manner to Example 8 from Intermediate 34.
rel-(3R,3aR,6aS)-4-(3-Piperidin-1-yl-propane-1-sulfonyl)-3-propyl-hexahydro-pyrrolo[3,2-b]pyrrol-2-one
Tlc (dichloromethane:methanol; 7:1) Rf 0.19.

Intermediate 136 rel-4-(6R-Isopropyl-4-methanesulfonyl-5-oxo-hexahydro-(3aS,6aR)-pyrrolo[3,2-b]pyrrole-1-carbonyl)-benzaldehyde A stirred solution of Intermediate 86 (100 mg) in acetonitrile (5 ml) under nitrogen had 1-(3-dimethylaminopropyl)-3-ethylcarbodiimide hydrochloride (156 mg), 1-hydroxybenzotriazole (110 mg) and 4-carboxybenzaldehyde (79 mg) added before stirring at 22° C. for 22 hours. The solvent was removed from the mixture in vacuo and the gummy residue partitioned between 2N $Na_2CO_3$ (15 ml) and dichloromethane (15 ml). The organic phase was separated, washed with 2N $Na_2CO_3$ (10 ml), water (10 ml) saturated brine (10 ml), dried ($MgSO_4$), filtered and the solvent removed in vacuo to give a yellow gum. The gum was purified by flash column chromatography using Merck 9385 silica and eluted with 2% MeOH/$CH_2Cl_2$. The required fractions were combined and the solvent removed in vacuo to give the title compound, as a white foam (148 mg). Tlc (Silica plate, 9:1 $CH_2Cl_2$/MeOH) Rf=0.60, visualised by UV, $KMnO_4$ Mass Spec.$MH^+$ (found)=379; $MH^+$ (calc.)=379.

Intermediate 137

The above Intermediate was prepared in a similar manner to Intermediate 87 from Intermediate 86.
rel-3-(6R-Isopropyl-4-methanesulfonyl-5-oxo-hexahydro-(3aS,6aR)-pyrrolo[3,2-b]pyrrole-1-carbonyl)-benzaldehyde
Tlc (dichloromethane:methanol; 19:1) Rf 0.3.

Intermediate 138

The above Intermediate was prepared in a similar manner to Example 173 from Intermediate 136.
rel-4-[4-(6R-Isopropyl-4-methanesulfonyl-5-oxo-hexahydro-(3aS,6aR)-pyrrolo[3,2-b]pyrrole-1-carbonyl)-benzyl]-piperazine-1-carboxylic acid tert-butyl ester
Tlc (dichloromethane:methanol; 9:1) Rf 0.46.

Intermediate 139 rel-(3R,3aR,6aS)-4-(4-Bromomethyl-benzenesulfonyl)-1-methanesulfonyl-3-propyl-hexahydro-pyrrolo[3,2-b]pyrrol-2-one Intermediate 26 (246 mg) was dissolved in acetonitrile (10 ml) and treated with potassium carbonate (414 mg) 4-(bromomethyl) benzene sulfonyl chloride (403 mg) was added and the mixture allowed to stir at room temperature for 2 h. The mixture was diluted with dichloromethane and the solution washed with water, brine and dried ($MgSO_4$) and concentrated to give a white solid. This was triturated with acetonitrile and filtered to give the title compound as a white solid (181 mg). Mass spec $MNH^+_4$ (found)=498 $MNH^+_4$ (calc)=498 Tlc (Ethyl Acetate:Hexane;1:2) Rf=0.23.

Intermediate 140

The above Intermediate was prepared in a similar manner to Intermediate 139 from Intermediate 86.

rel-(3R,3aR,6aS)-4-(4-Bromomethyl-benzenesulfonyl)-3-isopropyl-1-methanesulfonyl-hexahydro-pyrrolo[3,2-b]pyrrol-2-one Tlc (dichloromethane:ethyl acetate; 14:1) Rf 0.5 Mass spec. (found) MH$^+$=497/498, (calc) MH$^+$=497/498.

Intermediate 141 rel-(3R,3aR,6aS)-4-(4-Bromomethyl-benzoyl)-3-isopropyl-1-methanesulfonyl-hexahydro-pyrrolo[3,2-b]pyrrol-2-one Intermediate 86 (200 mg) was dissolved in dichloromethane (10 ml) and treated with sodium bicarbonate (204 mg) followed by 4-(bromomethyl) benzoyl chloride (227 mg). The reaction mixture was allowed to stir overnight. The mixture was poured into water and extracted with ethyl acetate. The combined organic extracts were washed with dilute HCl brine, dried (MgSO$_4$) and concentrated to give a yellow gum. This was chromatographed on silica, eluting with ethyl acetate:hexane; 1:1 to give the title compound as a white solid (287 mg). Mass spec MH$^+$ (found)=444 MH$^+$ (calc)=444.

Intermediate 142

The above Intermediate was prepared in a similar manner to Intermediate 87 from Intermediate 86.
rel-5-(6R-Isopropyl-4-methanesulfonyl-5-oxo-hexahydro-(3aS,6aR)-pyrrolo[3,2-b]pyrrole-1-carbonyl)-furan-2-carbaldehyde Mass spec (found) MNH$_4^+$=386, (calc) MNH$_4^+$=386.

Intermediate 143

The above Intermediate was prepared in a similar manner to Intermediate 115 from Intermediate 86.
rel-4-[4-(6R-Isopropyl-4-methanesulfonyl-5-oxo-hexahydro-(3aS,6aR)-pyrrolo[3,2-b]pyrrol-1-yl)-4-oxo-butyl]-piperidine-1-carboxylic acid tert-butyl ester Tlc (cyclohexane:ethyl acetate; 1:1) Rf 0.27 Mass spec. (found) MH$^+$=500, (calc) MH$^+$=500.

Intermediate 144

(2-Cyclopropyl-1-ethoxy-(E)-vinyloxy)-trimethyl-silane

A solution of n-butyllithium in hexanes (1.6M, 26 ml) was added with stirring to a solution of diisopropylamine (6.2 ml) in tetrahydrofuran (8 ml) at below −25° C. under nitrogen. After 30 min, the mixture was cooled to −75° C. and ethyl cyclopropylacetate (4.5 g) added dropwise keeping the temperature below −65° C. The mixture was then maintained below −75° C. for 3 h before chlorotrimethylsilane (3.8 ml) was added below −65° C. The reaction was allowed to warm to ambient temperature and then evaporated to dryness. The residue was slurried with hexane and filtered. The filtrate was evaporated to an orange oil which was distilled in vacuo to give the title compound (4.0 g) as a clear mobile liquid, b.p 80–82° C., 3×10$^{-2}$ bar.

Mass Spec MH$^+$ (found)=201 MH$^+$ (calc)=201.

Intermediate 145 trans-2-(Cyclopropyl-ethoxycarbonyl-methyl)-3-(2,2,2-trifluoro-acetylamino)-pyrrolidine-1-carboxylic acid benzyl ester A solution of Intermediate 144 (2.5 g) in dichloromethane (16 ml) was added at 0° C. with stirring to a solution of Intermediate 81 (2.0 g) in dichloromethane (16 ml) under nitrogen. Boron trifluoride diethyl etherate (4 ml) was then added dropwise and the reaction was stirred for a further 1 h. The reaction was quenched with 1M hydrochloric acid (10 ml). The aqueous phase was separated and extracted with dichloromethane (2×20 ml). The combined organics were washed with brine, dried (MgSO$_4$) and evaporated to give the title compound as a yellow oil (3.1 g) which was used crude in the following preparation.

Intermediate 146 trans-3-Amino-2-(cyclopropyl-ethoxycarbonyl-methyl)-pyrrolidine-1-carboxylic acid benzyl ester A mixture of crude Intermediate 145 (3.1 g) in aqueous potassium carbonate (9.3 g in 30 ml), acetonitrile (30 ml) and ethanol (40 ml) was heated at reflux at 16 h. The mixture was cooled and the organic layer separated and evaporated to give an oil. The oil was partitioned between 1M hydrochloric acid (25 ml) and ether (50 ml). The organic phase was extracted with 1M hydrochloric acid (3×25 ml). The combined aqueous solutions were washed with ether (25 ml) and basified to pH9 by the gradual addition, with stirring, of solid sodium carbonate. The mixture was then extracted with ethyl acetate (3×75 ml). The combined extracts were washed with brine (50 ml) dried (MgSO$_4$) and evaporated in vacuo to give the title compound as a viscous yellow oil (1.3 g). Mass spec MH$^{30}$ (found)=347 MH$^+$ (calc)=347.

Intermediate 147 rel-(3aS,6R,6aS)-6-Cyclopropyl-5-oxo-hexahydro-pyrrolo[3,2-b]pyrrole-1-carboxylic acid benzyl ester A solution of t-butylmagnesium chloride in tetrahydrofuran (1.0M, 11.25 ml) was added dropwise under a nitrogen atmosphere to a solution of Intermediate 146 (1.2 g) in a mixture of N,N,N',N'-tetramethylenediamine (13 ml) and tetrahydrofuran (13 ml) at 4–5° C. After 2 h the cooling was removed and the reaction temperature was allowed to attain ambient temperature. A second quantity (3 ml) of t-butylmagnesium chloride was added dropwise at room temperature at 4 h. After a further 2 h, saturated aqueous ammonium chloride (1 ml) was added and the reaction mixture was then acidified to pH 1–2 with hydrochloric acid. The mixture was extracted with ethyl acetate (3×30 ml). The combined organics were washed with brine (20 ml), dried (MgSO$_4$) and evaporated to a yellow paste, which was triturated with ethyl acetate to give a finely divided white solid (0.3 g) containing the title compound. M.p. 141–149° C. Purification by flash column chromatography using ethyl acetate:hexane (2:1) as eluent gave the title compound (0.2 g) as a solid foam.

Intermediate 148 rel-(3aS,6R,6aS)-6-Cyclopropyl-4-methanesulfonyl-5-oxo-hexahydro-pyrrolo[3,2-b]pyrrole-1-carboxylic acid benzyl ester A solution of lithium hexamethyldisilazide in tetrahydrofuran (1.0M, 0.1 ml) was added dropwise at −75° C. to a stirred solution of Intermediate 147 (0.25 g) in tetrahydrofuran (16 ml) under nitrogen. The reaction was stirred at −75° C. for 5 min and then around 0° C. for 25 min before being recooled to −75° C. Methanesulphonyl chloride (0.24 g) was added dropwise and the reaction was then stirred around −75° C. for 1.5 h. After 2 h saturated aqueous ammonium chloride (1.5 ml) and water (30 ml) were added sequentially. The mixture was extracted with ethyl acetate (3×25 ml) and the combined extracts were washed with brine (15 ml), dried (MgSO$_4$) and evaporated to a clear film. This was purified by flash column chromatography using ethyl acetate and hexane (1:2) as eluent to give the title compound as a white solid (0.21 g) m.p. 144–149.5° C.

Intermediate 149 rel-(3R,3aR,6aS)-3-Cyclopropyl-1-methanesulfonyl-hexahydro-pyrrolo[3,2-b]pyrrol-2-one A solution of Intermediate 148 (0.21 g) in ethyl acetate (25 ml) was added to prereduced moist 20% palladium hydroxide on carbon (Pearlman's catalyst) in ethyl acetate (20 ml). The mixture was stirred vigorously at room temperature under a hydrogen atmosphere for 1.5 h (hydrogen uptake 17 ml). The catalyst was filtered off and the filtrate evaporated to give the title compound as a white crystalline solid (0.13 g). M.p. 137–144° C. Mass spec MH$^+$ (found)= 245 MH$^+$ (calc)=245.

Intermediate 150
2R-tert-Butoxycarbonylamino-4-methylsulfanyl-butyric acid

A suspension of (R)-methionine in 1,4-dioxane (1000 ml) and 1.25M NaOH (1330 ml) was stirred and cooled to 6° C. before a solution of di-tert-butyldicarbonate (384 g) in 1,4-dioxane (300 ml) was added to it in one portion. The cooling bath was removed and the reaction stirred for 3.5 hours. The 1,4-dioxane was removed from the mixture in vacuo before ethyl acetate (1000 ml) was added, followed by 1M KHSO$_4$ (1700 ml). After mixing, and separation of the phases, the aqueous phase was further extracted with ethyl acetate (600 ml). The combined organic phases were washed with water (600 ml), brine (100 ml), dried (Na$_2$SO$_4$), filtered and the solvent removed in vacuo to give the title compound (449 g) as a pale yellow oil, containing some ethyl acetate. Mass spec MH$^+$ (found)=250 MH$^+$ (calc)=250.

Intermediate 151
(1R-Carbamoyl-3-methylsulfanyl-propyl)-carbamic acid tert-butyl ester Intermediate 150 (425 g) was dissolved in N,N-dimethylformamide (700 ml) and pyridine (63.2 ml) added. Di-tert-butyl dicarbonate (402.2 g) was added portionwise and the mixture stirred for 10 minutes at room temperature. Ammonium hydrogen carbonate (145.7 g) was added and the mixture stirred at room temperature for 18 hours. Water (1000 ml) was added to the mixture followed by ethyl acetate (1000 ml) and brine (250 ml). The mixture was stirred vigorously and allowed to separate. The aqueous phase was extracted with ethyl acetate (2×600 ml). The combined organic phases washed with water (1000 ml), dilute sulphuric acid (2×750 ml) [made from 38 ml conc. sulphuric acid and 1600 ml water), water (3×750 ml) and brine (1000 ml). The solution was dried over sodium sulphate and the solvent removed in vacuo to leave a white solid. This solid was triturated with diethyl ether (1200 ml), filtered off, and dried in vacuo to give the title compound as a white powder (265 g). Tlc SiO$_2$ (Ethyl Acetate:cyclohexane; 1:1) Rf 0.25 Mass spec MH$^+$ (found)=249, MH$^+$ (calc)=249.

Intermediate 152
(2R-tert-Butoxycarbonylamino-4-methylsulfanyl-butyryl)-carbamic acid benzyl ester n-Butyllithium in hexanes (2.5M, 992 ml) was added steadily to a stirred cooled solution of Intermediate 151 (308 g) in tetrahydrofuran (2000 ml) at such a rate as to maintain the temperature between −65 and −72° C. After 1 h 20 min a solution of benzyl chloroformate (211 g) in tetrahydrofuran (200 ml) was added steadily over 45 min maintaining the temperature below −60° C. The reaction was recooled below −70° C. and maintained there for 1.5 h. The reaction was quenched with saturated aqueous ammonium chloride (1000 ml). The temperature rose to −40° C. and was allowed to rise steadily to +10° C. The organic layer was separated and the aqueous layer extracted with ethyl acetate (3×50 ml). The combined organics were washed with brine (3×500 ml), dried (Na$_2$SO$_4$) and evaporated in vacuo to give the title compound as a clear pale yellow viscous oil (560 g). This material was used without further purification. Mass spec. (found) MNH$_4^+$=400 (calc) MNH$_4^+$=400.

Intermediate 153
(4-Benzyloxycarbonylamino-3R-tert-butoxycarbonylamino-4-oxo-butyl)-dimethyl-sulfonium iodide Methyl iodide (875 g) was added with stirring under nitrogen to a solution of Intermediate 152 (568 g) in acetone (875 ml) at room temperature. The reaction was stirred in the dark for 3 days and was then cooled in an ice bath for 4 h. The resultant pale yellow crystalline suspension was filtered and the filter pad washed with chilled (0° C.) acetone:ether (1:9; 1000 ml). The resultant white solid was dried to give the title compound as a white crystalline solid (559 g) m.p. 121–126° C.

Intermediate 154
(R)-3-tert-Butoxycarbonylamino-2-oxo-pyrrolidine-1-carboxylic acid benzyl ester Intermediate 153 (510 g) was dissolved in acetonitrile (2600 ml). 4A molecular sieves (ground to a powder, 55 g) were added, followed by Dowex 2×8-400 resin (hydroxide form, 640 g). The mixture was stirred vigorously for 3.5 h. More resin (60 g) was added at 3.5 h and a further quantity of resin (609) added at 5 h. After 6 h total reaction time, the mixture was filtered and the resin washed on the sinter with acetonitrile (1000 ml). The acetonitrile was removed in vacuo to give a straw coloured solid (360 g). This was dissolved in hot ethyl acetate (1500 ml) and the hot solution filtered. The filtrate was concentrated to approximately 800 ml and then diluted with cyclohexane (1500 ml). The mixture was heated on a steam bath until all the solid had dissolved (50 ml of ethyl acetate was added to achieve complete dissolution). The solution was allowed to cool and stood at room temperature for 3 days. The crystallised product was filtered and washed with ethyl acetate:cyclohexane (1:3, 400 ml) and dried in vacuo to give the title compound as white plates (217.5 g) Tlc SiO$_2$ (Ethyl acetate: cyclohexane; 1:1) Rf 0.55 Mass spec MNH$_4^+$ (found)=352 MNH$_4^+$ (calc)=352.

Intermediate 155
(R)-3-Amino-2-oxo-pyrrolidine-1-carboxylic acid benzyl ester hydrochloride Intermediate 154 (215 g) was suspended in 1,4-dioxane (400 ml) and treated with hydrogen chloride in 1,4-dioxan (4M, 800 ml) at room temperature. A white precipitate formed after 10 minutes which became very thick as the reaction proceeded. After 45 minutes total reaction time, more 1,4-dioxan (400 ml) was added. After 2.5 h total reaction time, the volatiles were removed in vacuo to give the title compound as a white solid (196 g). Tlc (ethanol:dichloromethane:ammonia;8:100:1) Rf 0.5 Mass spec MNH$_4^+$ (found)=252 MNH$_4^+$ (calc)=252

PREPARATION OF EXAMPLES

Example 1
rel-(3aS,6R,6aR)-6-Allyl-4-(naphthalene-2-sulfonyl)-5-oxo-hexahydro-pyrrolo[3,2-b]pyrrole-1-carboxylic acid benzyl ester Lithium hexamethyidisilylamide (1.0M in THF, 7.3 ml) was added to a solution of Intermediate 13 (2.0 g) in dry THF (80 ml) cooled to −70° C. (CO$_2$/acetone bath) under nitrogen. After stirring at −70° C. for 10 minutes, the cooling bath was replaced by an ice bath, and the mixture stirred for a further 25 minutes. The mixture was re-cooled to −70° C., before a solution of 2-naphthylsulphonylchloride (1.81 g) in dry THF (15 ml) was added to it dropwise. The mixture was stirred at −70° C. for a further 3 hours. The reaction was quenched with water (8 ml) and after the addition of further water at 5° C., extracted with ethyl acetate (3×200 ml). The combined extracts were washed with brine (50 ml), dried over MgSO$_4$, and the solvent evaporated in vacuo to give a yellow solid. This residue was purified by flash column chromatography (Merck 9385 silica) and eluted with ether to give the title compound as a white solid, (2.385 g). T.l.c. (Silica plate, ether) Rf=0.53, M.p.=158.5–159.5° C.

Example 2 rel-(3R,3aR,6aS)-1-(Naphthalene-2-sulfonyl)-4-(3-piperidin-1-yl-propionyl)-3-propyl-hexahydro-pyrrolo[3,2-b]pyrrol-2-one hydrochloride Intermediate 14 (0.5 g), 1-piperidine propionic acid (263 mg), 1-hydroxybenzotriazole (225.7 mg), and 1-(3-N,N-dimethylaminopropyl)-3-ethylcarbodiimide (320 mg) were dissolved in dry dichloromethane (10 ml). Triethylamine (0.58 ml) was added, and the resulting mixture stirred at room temperature for 18 h. The mixture was partitioned between 2M sodium carbonate solution (100 ml), and ethyl acetate (100 ml). The organic phase was separated, the aqueous phase further extracted with ethyl acetate (100 ml), and the combined organic phase dried (MgSO$_4$). The solvent was evaporated in vacuo to leave a yellow gum. Flash chromatography (Merck, SiO$_2$, 9385) eluting with ethyl acetate:triethylamine (100:1) gave a white foam. The foam (200 mg) was dissolved in ether (10 ml), and ethereal hydrogen chloride 1M (1 ml) added. The solvent was evaporated in vacuo, the residue triturated with ether (30 ml) and dried in vacuo to give the title compound (190.2 mg), m.p.=230°–234° C. (dec.). T.l.c. SiO$_2$ (free base) ethyl acetate:methanol (2:1) Rf=0.28

Examples 3, 30, 54, 56, 57 and 59

The above examples were prepared in a similar manner to Example 2:
rel-(3R,3aR,6aS)-1-(Naphthalene-2-sulfonyl)-4-(2-piperidin-1-yl-acetyl)-3-propyl-hexahydro-pyrrolo[3,2-b]pyrrol-2-one Prepared from Intermediate 14 and Intermediate 15, white crystalline solid (33.7 mg), m.p.=161°–163° C., T.l.c. SiO$_2$, ethyl acetate:triethylamine (100:1) Rf=0.23. (Example 3)
rel-(3R,3aR,6aS)-1-Methanesulfonyl-4-(3-piperidin-1-yl-propionyl)-3-propyl-hexahydro-pyrrolo[3,2-b]pyrrol-2-one hydrochloride Prepared from Intermediate 26 and 3-piperidinopropanoic acid, I.R. (MeOH) ν$_{max}$ 1752 cm$^{-1}$. (Example 30)
(3S,3aS,6aR)-1-(Naphthalene-2-sulfonyl)-4-(3-piperidin-1-yl-propionyl)-3-propyl-hexahydro-pyrrolo[3,2-b]pyrrol-2-one hydrochloride Prepared from Intermediate 69, cream solid, Chiral HPLC (Chiracel OD-H column, eluent system propan-2-ol:triethylamine:heptane; 20:1:79, flow rate=1 ml/min). Retention time=16.4 min, >99% e.e. (Example 54)
(3R,3aR,6aS)-1-(Naphthalene-2-sulfonyl)-4-(3-piperidin-1-yl-propionyl)-3-propyl-hexahydro-pyrrolo[3,2-b]pyrrol-2-one hydrochloride Prepared from Intermediate 70, cream solid, Chiral HPLC (Chiracel OD-H column, eluent system propan-2-ol:triethylamine:heptane; 20:1:79, flow rate=1 ml/min). Retention time=13.9 min, 81% e.e (Example 56)
rel-(3R,3aR,6aS)-1-Methanesulfonyl-4-(4-piperidin-1-yl-but-2-(E)-enoyl-3-propyl-hexahydro-pyrrolo[3,2-b]pyrrol-2-one hydrochloride Prepared from Intermediate 26 and (E)-4-piperidin-1-yl-but-2-enonic acid, buff powder, T.l.c (dichloromethane:ethanol:ammonia; 100:8:1) Rf 0.43, Mass spec MH$^+$ (found) 398, MH$^+$ (calculated) 398. (Example 57)
rel-(3R,3aR,6aS)-4-(6-Azepin-1-yl-hexanoyl)-1-methanesulfonyl-3-propyl-hexahydro-pyrrolo[3,2-b]pyrrol-2-one hydrochloride Prepared from Intermediate 26 and 6-azepin-1-yl-hexanoic acid, white solid, T.l.c. (Ethyl acetate:ammonia, 95:5) Rf 0.31 Mass spec MH$^+$ (found) 442 MH$^+$ (calculated) 442. (Example 59)

Examples 4, 53 and 55

The above examples were prepared in a similar manner to Example 1:
rel-(3aS,6R,6aR)-6-Ethyl-4-(naphthalene-2-sulfonyl)-5-oxo-hexahydro-pyrrolo[3,2-b]pyrrole-1-carboxylic acid benzyl ester Prepared from Intermediate 24, white solid, T.l.c. (diethyl ether) Rf 0.47, M.p.=155.5–156.5° C. (Example 4)
(3aR,6S,6aS)-6-Allyl-4-(naphthalene-2-sulfonyl)-5-oxo-hexahydro-pyrrolo[3,2-n]pyrrole-1-carboxylic acid benzyl ester Prepared from Intermediate 68, white solid, Chiral HPLC (Chiracel OD-H column, eluent system propan-2-ol:triethylamine:heptane; 5:3:92, flow rate=1 ml/min). Retention time=32.3 min, >99% e.e. [α]$^{20}_D$ (Na lamp 589 nm) +66.80 (c=5, CHCl$_3$) (Example 53)
(3aS,6R,6aR)-6-Allyl-4-(naphthalene-2-sulfonyl)-5-oxo-hexahydro-pyrrolo[3,2-b]pyrrole-1-carboxylic acid benzyl ester Prepared from Intermediate 67, white solid, Chiral HPLC (Chiracel OD-H column, eluent system propan-2-ol:heptane; 1:9, flow rate=1 ml/min). Retention time=39.4 min, 86% e.e. [α]$^{20}_D$ (Na lamp, 589 nm) −52.8° (C=5, CHCl$_3$) (Example 55)

Example 5 rel-(3R,3aR,6aS)-3-Ethyl-1-(naphthalene-2-sulfonyl)-4-(3-piperidin-1-yl-propionyl)-hexahydro-pyrrolo[3,2-b]pyrrol-2-one hydrochloride A mixture of Intermediate 25 (50 mg), 1-piperidine-propionic acid (27 mg) and 1-(3-dimethylaminopropyl)-3-ethylcarbodiimide hydrochloride (45 mg) was stirred at room temperature in dichloromethane (3 ml) for 18 hours. The mixture was poured into water (10 ml) and extracted with ethyl acetate (3×20 ml). The combined extracts were washed with brine (15 ml), dried (MgSO$_4$), filtered and the solvent evaporated in vacuo to give a yellow solid. This residue was purified by flash chromatography on silica (Merck 9385) using methanol:ethyl acetate (2:3) as eluent to give the free base. The free base was stirred in dichloromethane (3 ml) and methanol (3 ml) and a 1.0M solution of HCl in diethyl ether (300 ml) was added. After stirring for 30 minutes, the solvent was evaporated in vacuo and the oily residue dissolved in ether (20 ml), before evaporation of the solvent in vacuo to give the title compound as a colourless crunchy foam. T.l.c. (2:3 methanol:ethyl acetate) Rf 0.20, M.p. 173.5–175.5° C.

Example 6 rel-(3aS,6R,6aR)-6-Allyl-4-methanesulfonyl-5-oxo-hexahydro-pyrrolo[3,2-b]pyrrole-1-carboxylic acid benzyl ester Intermediate 13 (500 mg) was dissolved in tetrahydrofuran (30 ml) and cooled to −70° C. under nitrogen. Lithium hexamethyidisilylamide (1M in THF, 2.17 ml) was added and the mixture allowed to stir for 6 min. at −70° C. The dry ice/acetone bath was removed and replaced with an ice/water bath and the reaction mixture allowed to warm to 0° C. and stirred for 20 min. The reaction mixture was re-cooled to −70° C. and methanesulfonyl chloride (479 mg) added and the reaction allowed to stir for 1 h. The reaction was quenched with saturated ammonium chloride solution and allowed to warm to room temperature. The mixture was extracted with ethyl acetate and the combined organic extracts washed with brine, dried (MgSO$_4$) and evaporated to give a pale yellow gum. This was chromatographed on silica (eluting with ethyl acetate:hexane; 1:2) to give the title compound as a white solid (527 mg). T.l.c. (1:2; Ethyl acetate:hexane) Rf 0.17, M.p. 92–94° C.

Example 7 rel-(3R,3aR,6aS)-1-Methanesulfonyl-4-(1-methyl-1H-imidazole-4-sulfonyl)-3-propyl-hexahydro-pyrrolo[3,b] pyrrol-2-one 1-Methylimidazole-4-sulfonyl chloride (28 mg) was added to a solution of the Intermediate 26 (32 mg) and triethylamine (44 ml) in dichloromethane (3 ml) under nitrogen. After 4 h the mixture was poured into water and extracted with ethyl acetate. The combined organic extracts were washed with dilute (8%) sodium bicarbonate solution, brine, dried (MgSO$_4$) and concentrated to give a beige solid. This was triturated with ether/hexane and filtered to give the title compound as a straw solid (40 mg). M.p. 192–193° C., T.l.c. (Dichloromethane:methanol; 95:5) Rf 0.27

Example 8 rel-(3R,3aR,6aS)-1-Methanesulfonyl-4-(3-morpholin-4-yl-propane-1-sulfonyl)-3-propyl-hexahydro-pyrrolo[3,2-b] pyrrol-2-one Intermediate 27 (38 mg) was added to a stirred solution of Intermediate 26 (30 mg) and triethylamine (30 mg) in dichloromethane (3 ml) under nitrogen. After 3 h the reaction mixture was poured into water and extracted with ethyl acetate. The combined organic extracts were washed with brine, dried (MgSO$_4$) and concentrated to give a cream solid. This was chromatographed on silica (eluting with ethyl acetate:methanol, 100:0→99:1) to give the title compound as a white solid (26 mg), M.p. 135° C. (dec.), T.l.c. (Ethyl acetate) Rf 0.12.

Example 8a rel-(3R,3aR,6aS)-1-Methanesulfonyl-4-(3-morpholin-4-yl-propane-1-sulfonyl)-3-propyl-hexahydro-pyrrolo[3,2-b] pyrrol-2-one hydrochloride Example 8 (60 mg) was dissolved in tetrahydrofuran (10 ml) and cooled to 0° C. Hydrogen chloride gas was bubbled through the solution for 2 mins. After standing for 1 h the solvent was evaporated to give a white solid. This was triturated with ether and filtered to give the title compound as a white solid (55 mg), M.p. 72–74° C., I.r. (KBr) $v_{max}$ 1751, 1353, 1156 cm$^{-1}$.

Examples 9, 10, 11, 12, 13, 14, 26, 27, 31, 32, 36

The above examples were made in a similar manner to Example 8 (and 8a as appropriate):

rel-(3R,3aR,6aS)-1-Methanesulfonyl-4-(3-piperidin-1-yl-propane-1-sulfonyl)-3-propyl-hexahydro-pyrrolo[3,2-b] pyrrol-2-one Prepared from Intermediate 26 and Intermediate 28, white solid, M.p. 199–200° C. (dec.), T.l.c. (Dichloromethane:methanol; 9:1) Rf 0.4. (Example 9)

rel-(3R,3aR,6aS)-1-Methanesulfonyl-4-[3-(4-methyl-piperazin-1-yl)-propane-1-sulfonyl]3-propyl-hexahydro-pyrrolo[3,2-b]pyrrol-2-one dihydrochloride Prepared from Intermediate 26 and Intermediate 30, beige solid, M.p. 128–130° C., Mass Spec. MH$^+$ (obs) 451 MH$^+$ (calc) 451. (Example 10)

rel-(3R,3aR,6aS)-4-(4-Morpholin-4-yl-butane-1-sulfonyl)-1-(naphthalene-2-sulfonyl)-3-propyl-hexahydro-pyrrolo[3,2-b]pyrrol-2-one Prepared from Intermediate 14 and Intermediate 32, white solid, M.p. 180–182° C. (dec.), T.l.c. (Dichloromethane:methanol; 99:1) Rf 0.46. (Example 11)

rel-(3R,3aR,6aS)-4-(3-Morpholin-4-yl-propane-1-sulfonyl)-1-(naphthalene-2-sulfonyl)-3-propyl-hexahydro-pyrrolo[3,2-b]pyrrol-2-one Prepared from Intermediate 14 and Intermediate 27, M.p. 189–192° C., T.l.c. (Ethyl acetate:methane; 9:1) Rf 0.32. (Example 12)

rel-(3R,3aR,6aS)-1-(Naphthalene-2-sulfonyl)-(3-piperidin-1-yl-propane-1-sulfonyl)-3-propyl-hexahydro-pyrrolo[3,2-b]pyrrol-2-one Prepared from Intermediate 14 and Intermediate 28 to give the title compound as a white solid. M.p. 202–2031° C., T.l.c. (Dichloromethane:methanol; 9:1) Rf 0.1. (Example 13)

rel-(3R,3aR,6aS)-4-[3-(4-Methyl-piperazin-1-yl)-propane-1-sulfonyl-1-(naphthalene-2-sulfonyl)-3-propyl-hexahydro-pyrrolo[3,2-b]pyrrol-2-one Prepared from Intermediate 14 and Intermediate 30, white solid, M.p. 186–187° C., T.l.c. (Dichloromethane:methanol; 9:1) Rf 0.2. (Example 14)

rel-(3R,3aR,6aS)-1,4-Bis-methanesulfonyl-3-propyl-hexahydro-pyrrolo[3,2-b]pyrrol-2-one Prepared from Intermediate 26 and methane sulphonylchloride, white solid, M.p. 205–8° C., T.l.c. (19:1 ethyl acetate:methanol) Rf 0.60. (Example 26)

rel-(3R,3aR,6aS)-1-Methanesulfonyl-3-propyl-4-[3-(1H-tetrazol-5-yl)-phenylmethanesulfonyl]-hexahydro-pyrrolo[3,2-b]pyrrol-2-one Prepared from Intermediate 26 and Intermediate 42, white solid, M.p. 180–210° C. (dec.), T.l.c. (19:1 ethyl acetate:methanol) Rf 0.31. (Example 27)

rel-(3R,3aR,6aS)-4-Methanesulfonyl-1-(naphthalene-1-sulfonyl)-3-propyl-hexahydro-pyrrolo[3,2-b]pyrrol-2-one Prepared from Intermediate 33 and methanesulphonyl chloride, cream solid, M.p. 185–7° C., T.l.c. (19:1 ethyl acetate:methanol) Rf 0.68. (Example 31)

rel-(3R,3aR,6aS)-1-(Naphthalene-1-sulfonyl)-3-propyl-4-[3-(1H-tetrazol-5-yl)-phenylmethanesulfonyl]-hexahydro-pyrrol[3,2-b]pyrrol-2-one Prepared from Intermediate 33 and Intermediate 42, white solid, M.p. 175–6° C., T.l.c. (19:1 ethyl acetate:methanol) Rf 0.40 (streak) (Example 32)

rel-(3R,3aR,6aS)-4-(3-Morpholin-4-yl-propane-1-sulfonyl)-1-(naphthalene-1-sulfonyl)-3-propyl-hexahydro-pyrrolo[3,2-b]pyrrol-2-one Prepared from Intermediate 33 and Intermediate 27, T.l.c. SiO$_2$ (methanol:dichloromethane; 1:9) Rf 0.64, M.p.= 146–148° C. (Example 36)

Example 15 rel-(3sS,6R,6aR)-6-Allyl-4-(naphthalene-1-sulfonyl)-5-oxo-hexahydro-pyrrolo[3,2-b]pyrrole-1-carboxylic acid benzyl ester Sodium hydride (96 mg, 60% in mineral oil) was added to a cooled solution (ice-bath) of Intermediate 13 (600 mg) in tetrahydrofuran (20 ml) under N$_2$. After 30 min, 1-naphthalene sulphonyl chloride (542 mg) was added and the mixture allowed to warm to room temperature and stirred for 5 h. The mixture was poured into saturated ammonium chloride solution and extracted with ethyl acetate. The combined organic extracts were washed with 8% sodium bicarbonate solution, brine, dried (MgSO$_4$) and concentrated to give a white solid. This was chromatographed on silica (eluting with DCM then ether then ethyl acetate) to give the title compound.

T.l.c. (ether) Rf 0.76.

$^1$H NMR (CDCl$_3$) δ8.69 (1H, d); 8.48 (1H, d); 8.16 (1H, d); 7.98 (1H, d); 7.73–7.58 (3H, m); 7.33 (5H, s); 5.42–5.70 (1H, br); 5.10 (2H, s); 4.96 (2H, br, d); 3.80 (2H, m); 3.57 (2H, m); 3.57 (1H, m); 3.23 (1H, t); 2.78–2.57 (4H, m); 2.11 (1H, m).

Example 16 rel-(3aS,6R,6aR)-4-[4-(Naphthalene-1-sulfonyl)-5-oxo-6-propyl-hexahydro-pyrrolo[3,2-b]pyrrol-1-carbonyl-carbonyl]-piperidine-1-carboxylic acid tert-butyl Prepared in a similar manner to Example 29 from Intermediate 33 and N-t-butoxy-carbonyl-piperidine-4-carboxylic acid [S. I. Klein, and B. F Molino, U.S. Pat. No. 5,064,814] to give the title compound. T.l.c. SiO$_2$ (Ether) Rf 0.4, Mass Spec. MH$^+$ (calc) 570 MH$^+$ (obs) 570.

Example 17 rel-(3R,3aR,6aS)-1-(Naphthalene-1-sulfonyl)-4-(piperidine-carbonyl-carbonyl)-3-propyl-hexahydro-pyrrolo[3,2-b]pyrrol-2-one trifluoroacetate Example 16 (37 mg) was dissolved in dichloromethane (9 ml) and trifluoroacetic acid (2 ml) added. The reaction mixture was allowed to stand at room temperature for 3 h. The solvents were evaporated and the residue triturated with dichloromethane/ether to give a white solid. The solid was filtered and air-dried to give the title compound (14 mg). M.p. 185–188° C. (dec.), I.r. (CHCl$_3$) ν$_{max}$ 3400–2500, 1758, 1673, 1138 cm$^{-1}$.

Examples 18, 20, 21

The above examples were prepared in a similar manner to Example 15:

rel-(3aS,6R,6aR)-6-Allyl-4-(5-dimethylamino-naphthalene-1-sulfonyl)-5-oxo-hexahydro-pyrrolo[3,2-b]pyrrol-1-carboxylic acid benzyl ester Prepared from Intermediate 13 and dansylchloride, yellow oil, T.l.c. (1:2 ethyl acetate:hexane) 0.17, Mass Spec. MH$^+$ (found) 534 MH$^+$ (calculated) 534. (Example 18)

rel-(3aS,6R,6aR)-6-Allyl-5-oxo-4-(5,6,7,8-tetrahydro-naphthalene-2-sulfonyl)-hexahydro-pyrrolo[3,2-b]pyrrol-1-carboxylic acid benzyl ester Prepared from Intermediate 13 and 2-chlorosulphonyl-5,6,7,8-tetrahydronaphthalene [Chem. Abstr. W. Schenlz, H. U. Blank, F. Hagedom, W. Evertz, German Patent 1979, DE 2743540 790405], white solid, T.l.c. (3:1 hexane:ethyl acetate) Rf 0.24, Assay Found: C,65.43; H,5.94; N,5.55%, C$_{27}$H$_{30}$N$_2$O$_5$S requires C,65.57; H,6.11; N,5.66%. (Example 20)

rel-3aS,6R,6aR)-6-Allyl-5-oxo-4-phenylmethanesylfonyl-hexahydro-pyrrolo[3,2-b]pyrrol-1-carboxylic acid benzyl ester Prepared from Intermediate 13 and benzyl sulphonylchloride, oil, T.l.c. (1:3 ethyl acetate:hexane) Rf 0.37, I.r. (CHCl$_3$) 1753, 1703, 1363, 1136 cm$^{-1}$. (Example 21)

Example 19 rel-(3aS,6R,6aR)-6-Allyl-4-benzylsulfamoyl-5-oxo-hexahydro-pyrrolo[3,2-b]pyrrol-1-carboxylic acid benzyl ester Intermediate 13 (0.034 g), 60% sodium hydride (0.007 g) and tetrahydrofuran (1.5 ml) were mixed under nitrogen at room temperature. After 5 minutes, the temperature was lowered to 0° C. for 30 min and then lowered to −70° C. when sulfuryl chloride (9 ml) was added. After 2 h the mixture was warmed to room temperature and benzylamine (25 ml) added. After 30 min the mixture was added to saturated ammonium chloride solution and extracted with ethyl acetate (3×20 ml). The combined extracts were washed with 1M hydrochloric acid, brine and dried (MgSO$_4$) and the solvent removed in vacuo. Flash chromatography on silica (Merck 9385) using ether as eluent gave the title compound as a white solid (0.003 g), T.l.c, (ether) Rf 0.21 Mass Spec. MH$^+$ (found) 458 MH$^+$ (calculated) 458.

Example 22 rel-(3R,3aR,6aS)-4-Methanesulfonyl-1-(naphthalene-2-sulfonyl)-3-propyl-hexahydro-pyrrolo[3,2-b]pyrrol-2-one Intermediate 14 (0.0196 g) and mesyl chloride (0.007 ml) in dry dichloromethane (2 ml) were stirred under nitrogen at room temperature for 1 h. Triethylamine (0.016 ml) was added and stirring continued for 24 h. The mixture was partitioned between ethyl acetate (20 ml) and dilute sodium chloride solution (20 ml). The aqueous layer was extracted with ethyl acetate (15 ml), the combined organics dried (MgSO$_4$) and the solvent removed in vacuo to give a solid. This was purified by flash chromatography (Merck 9385) using ethyl acetate(hexane (1:1) as eluent to give the title compound as a white solid (0.009 g), M.p. 257–260° C., T.l.c. (1:1 ethyl acetate:hexane) Rf 0.45.

Example 23 rel-(3R,3aR,6aS)-1(Naphthalene-2-sulfonyl)-3-propyl-4-[3-(1H-tetrazol-5-yl)-phenylmethanesulfonyl]-hexahydro-pyrrolo[3,2-b]pyrrol-2-one Intermediate 14 (0.021 g) and Intermediate 42 (0.023 g) in dichloromethane (1.5 ml) were stirred at ambient temperature under nitrogen for 30 min. Triethylamine (0.016 ml) was added and the mixture stirred for a further 18 h. The mixture was partitioned between ethyl acetate (15 ml) and water (15 ml). The aqueous layer was extracted with ethyl acetate (2×15 ml), the combined organics dried (MgSO$_4$) and the solvent removed in vacuo to give a solid. This was purified by flash chromatography on silica (Merck 9385) using ethyl acetate:hexane as eluent (1:1) increasing to ethyl acetate:hexane:acetic acid (99:99:2) to give the title compound as a white solid (0.024 g). T.l.c. (1:1 ethyl acetate:hexane) Rf 0.1Mass Spectrum MNH$_4^+$ (obs)=598 MNH$_4^+$ (calc)=598.

Example 24 rel-(3R,3aR,6aS)-4-Acetyl-1-(naphthalene-2-sulfonyl)-3-propyl-hexahydro-pyrrolo[3,2-b][pyrrol-2-one Prepared in a similar manner to Example 28 from Intermediate 14 and acetyl chloride to give the title compound as a white solid. T.l.c. (1:1 ethyl acetate:hexane) Rf 0.15 I.r. (KBr) ν$_{max}$ 3436, 1767, 1362, 1338, 1165, 1133 cm$^{-1}$.

Example 25 rel-(3R,3aR,6aS)-4-(4-Dimethylamino-butyryl)-1-(naphthalene-2-sulfonyl)-3-propyl-hexahydro-pyrrolo[3,2-b]-pyrrol-2-one Prepared in a similar manner to Example 29 from Intermediate 14 and 4-dimethylaminobutanoic acid to give the title compound as a white solid.

$^1$H NMR (CDCl$_3$) δ8.61(1H, S); 8.05–7.90 (4H,m); 7.73–7.6 (2H,m); 3.94–3.77 (2H,m); 3.37 (1H,td); 3,24 (1H,t); 2.77 (1H,m); 2.56 (1H,dt); 2.28 (4H,q), 2.2 (6H,s); 2.1–0.94 (5H,m); 0.89 (3H,t).

Example 28 rel-(3R,3aR,6aS)-4-Acetyl-1-methanesulfonyl-3-propyl-hexahydro-pyrrolo[3,2-b]pyrrol-2-one A mixture of Intermediate 26 (0.023 g), triethylamine (18 ml) and acetylchloride (7.3 ml) in dichloromethane (1 ml) were stirred at room temperature for 1 h under nitrogen. The dichloromethane was removed in vacuo and the residue partitioned between ethyl acetate and water. The organic layer was separated, washed with brine and dried (MgSO$_4$). The solvent was removed in vacuo to afford the title compound as a white solid (0.017 g). T.l.c. (19:1 ethyl acetate:methanol) Rf 0.47 Mass Spec. MH$^+$ (found) 289 MH$^+$ (calculated) 289.

Example 29
rel-(3R,3aR,6aS)-1-Methanesulfonyl-4-(3-piperidin-1-yl-propionyl)-3-propyl-hexahydro-pyrrolo[3,2-b]pyrrol-2-one Intermediate 26 (0.038 g), 3-piperidinopropanoic acid (0.030 g), 1-(dimethylaminopropyl)-3-ethyl carbodiimide hydrochloride (0.042 g) and dichloromethane (2.6 ml.) were mixed at room temperature for 24 h under nitrogen. The solution was diluted with ethyl acetate and washed with brine and the aqueous layer extracted further with ethyl acetate. The combined organic layers were dried (MgSO$_4$) and concentrated in vacuo. The residue was purified by flash chromatography on silica (Merck 9385) eluting with 7:3 ethyl acetate:methanol to give the title compound as a colourless oil (0.048 g). T.l.c. (7:3 ethyl acetate:methanol) Rf 0.19 Mass Spec. MH$^+$ (found) 386 MH$^+$ (calculated) 386.

Example 33
rel-(3R,3aR,6aS)-1-(2-Phenyl-(E)-ethenesulfonyl)-4-phenylmethanesulfonyl-3-propyl-hexahydro-pyrrolo[3,2-b]pyrrol-2-one Intermediate 35 (0.048 g) in dimethylformamide (2 ml)ltetrahydrofuran (0.5 ml) was cooled (0° C.) under nitrogen and sodium hydride (60% in oil dispersion) (0.022 g) added. The suspension was stirred at 0° C. for 55 min. and trans β-styrenesulphonylchloride (0.104 g) then added. After stirring for 4.75 h, allowing the solution to warm to room temperature, the reaction was quenched with water. The mixture was partitioned between dilute sodium chloride (15 ml) and ethyl acetate (10 ml). The aqueous layer was extracted with ethyl acetate, the combined organics washed with 10% lithium chloride solution (2×10 ml), dried (MgSO$_4$) and concentrated in vacuo to give a yellow solid. This was purified by flash chromatography on silica (Merck 9385) using hexane/ethyl acetate (4:1) as eluent to give the title compound as a white solid (0.0032 mg). Mass Spec MH$^+$ (obs) 489 MH$^+$ (calc) 489.

$^1$H NMR (CDCl$_3$) δ7.68 (1H, d); 7.75–7.34 (10H, m); 6.97 (1H, d); 4.28 (2H, q); 3.62 (2H, m); 3.43 (1H, m); 3.18 (1H, d); 2.55 (1H, m); 2.38 (1H, m); 2.05 (1H, m); 1.80–1.14 (4H, m); 0.88 (3H, t).

Example 34
rel-(3aR,6R,6aS)-1-(Naphthalene-2-sulfonyl)-4-phenylmethanesulfonyl-3-propyl-hexahydro-pyrrolo[3,2-b]pyrrol-2-one Intermediate 35 (0.052 mg) in dimethylformamide (2 ml)/tetrahydrofuran (0.5 ml) was cooled (0° C.) under nitrogen and sodium hydride (60% in oil dispersion) (12 mg) added. The suspension was stirred at 0° C. for 55 min. and 2-napthalenesulphonylchloride (0.184 g) added. After stirring for 3.75 h, allowing to warm to room temperature, the reaction was quenched with water. The mixture was partitioned between ethyl acetate (15 ml) and dilute sodium chloride solution (15 ml). The aqueous layer was extracted with ethyl acetate (2×10 ml), the combined organics dried (MgSO$_4$) and concentrated in vacuo to give a yellow solid. This was purified by flash chromatography on silica (Merck 9385) using hexane/ethyl acetate (2:1) as eluent to give the title compound as a white solid (0.019 g) m.p. 221–224° C., T.l.c. (1:1 ethyl acetate:hexane) Rf 0.66.

Example 35
rel-(3R,3aR,6aS)-3-Ethyl-4-(3-morpholin-4-yl)-propane-1-sulfonyl)-1-(naphthalene-2-sulfonyl)-hexahydro-pyrrolo[3,2-b]pyrrol-2-one meso-tartrate A mixture of Intermediate 27 (61 mg), Intermediate 25 (50 mg) and triethylamine (67 ml) in dry dichloromethane (4 ml) were stirred together at room temperature under nitrogen. After 18 hours, the mixture was poured into water (10 ml) and extracted with ethyl acetate (3×20 ml). The combined extracts were washed with brine (20 ml), dried (MgSO$_4$), filtered and the solvent evaporated in vacuo to give a pale yellow solid. The solid was purified by flash chromatography on silica (Merck 9385) using methanol: ethyl acetate (1:4) as eluent to give the free base. The free base was dissolved in ethanol (5 ml) and a solution of D,L-tartaric acid (14.8 mg) in ethanol (3 ml) was added with stirring. After 30 minutes, the solvent was evaporated in vacuo and the solid residue was triturated in ether. The solid was filtered off and dried in vacuo to give the title compound as a white solid. T.l.c. (1:4 methanol:ethyl acetate) Rf=0.40, M.p. 154.5–155.5° C.

Example 37
rel-(3aS,6R,6aR)-6-Allyl-4-(3-dimethylsulfamoyl-benzenesulfonyl)-5-oxo-hexahydro-pyrrolo[3,2-b]pyrrole-1-carboxylic acid benzyl ester Intermediate 13 (50 mg), 3-N,N-dimethylsulphamoylbenzene-sulphonyl chloride (Intermediate 20) (56 mg), and tetrabutylammonium chloride (10 mg) were dissolved in dichloromethane (2 ml). 2M Potassium hydroxide (100 ml) was added, and the resulting solution stirred at room temperature. After 5 h, t.l.c. indicated no starting material remaining. The mixture was partitioned between 2M sodium carbonate solution (50 ml), and ethyl acetate (50 ml). The organic phase was separated, dried (MgSO$_4$), and the solvent evaporated in vacuo to leave a pale yellow gum. Flash chromatography (9385) eluting with ether:hexane (5:1) gave the title compound as a white solid (38.2 mg), m.p.=70–75° C. T.l.c. SiO$_2$ (5:1) ether:hexane Rf 0.34.

Example 38
rel-(3aS,6R,6aR)-6-Allyl-4-(3-nitro-benzenesulfonyl)-5-oxo-hexahydro-pyrrolo[3,2-b]pyrrole-1-carboxylic acid benzyl ester Intermediate 13 (50 mg), 3-nitrobenzenesulphonylchloride (55 mg), and tetrabutylammonium bromide (10 mg) were dissolved in dichloromethane (2 ml). Potassium hydroxide 2M (0.125 ml) was added and the resulting mixture stirred at room temperature for 6 h. The mixture was partitioned between 2M sodium carbonate solution (50 ml) and ethyl acetate (50 ml), the organic phase separated, dried (MgSO$_4$) and the solvent evaporated in vacuo to leave a colourless gum. Flash chromatography (9385) eluting with ether:hexane (1:1) gave the title compound as a white solid (28 mg).

I.r. $v_{max}$ 1762,1705, 1538, 1435, 1354 cm$^{-1}$
Mass spectrum MH$^+$ (obs)=486 MH$^+$ (calc)=486.

Example 39
rel-(3R,3aR,6aS)-1-(Naphthalene-2-sulfonyl)-4-(4-piperidin-l-yl-butyryl)-3-propyl-hexahydro-pyrrolo[3,2-b]pyrrol-2-one tartrate Intermediate 14 (40 mg), 1-hydroxybenzotriazole (18 mg), 1-(3-N,N-dimethylaminopropyl)-3-ethylcarbodiimide hydrochloride (25.6 mg), and Intermediate 17 (23 mg) were dissolved in dichloromethane (3 ml). Triethylamine (0.06 ml) was added, and the mixture stirred at room temperature overnight. The mixture was partitioned between ethyl acetate (50 ml) and 2M potassium carbonate (50 ml), and the organic phase separated. The aqueous phase was further extracted with ethyl acetate (50 ml), the combined organic phase dried (MgSO$_4$), and the solvent evaporated to dryness in vacuo. Flash chromatography of the residue eluting with ethyl acetate:methanol:triethylamine (700:500:1) gave a colourless gum (34.7 mg). This was dissolved in ethanol (1 ml), (dl)-tartaric acid (10.2 mg) in ethanol (2 ml) was added and the mixture evaporated to dryness in vacuo. Trituration of the residue with ether (20 ml) gave the title compound (39.7 mg) as a white solid m.p.=84–86° C. (foams). T.l.c. SiO$_2$ (ethyl acetate:methanol:triethylamine 700:300:1) Rf=0.21.

Example 40 rel-(3R,3aR,6aS)-1-(Naphthalene-2-sulfonyl)-4-(6-piperidin-1-yl-hexanoyl)-3-propyl-hexahydro-pyrrolo[3,2-b]pyrrol-2-one tartrate Prepared in a similar manner to Example 39 from Intermediate 14 and Intermediate 19 to give the title compound as a white solid, m.p.=85° C.–86° C. (foams). T.l.c. SiO$_2$ (free base) ethyl acetate:methanol (7:3) Rf=0.15.

Example 41 rel-(3aS,6R,6aR)-6-Allyl-4-(benzo[b]thiophene-3-sulfonyl)-5-oxo-hexahydro-pyrrolo[3,2-b]pyrrole-1-carboxylic acid benzyl ester To Intermediate 13 (0.04 g) in tetrahydrofuran (1.5 ml) under nitrogen at 0° C. was added sodium hydride (0.007 g) and then the mixture was left to stir for half an hour. The intermediate 44 (0.05 g) was then added and left for an hour, after which dimethylformamide (0.5 ml) was added and the reaction left for 24 h. The reaction was quenched with ammonium chloride (20 ml) and extracted with ethyl acetate (3×20 ml), washed with brine (20 ml) and dried (MgSO$_4$). The solvent was evaporated in vacuo to give a white solid (83 mg). This was purified by flash chromatography eluting with ethyl acetate:hexane (1:4) to give a white solid (0.037 mg). This was recrystallised using EtOAc/hexane to give the title compound (17.3 mg).

T.l.c. SiO$_2$, hexane:ethyl acetate, (4:1) Rf=0.17,
I.R. vmax; 3113, 1762, 1704, 1603, 1172, 1131 cm$^{-1}$.

Example 42 rel-(3aR,6R,6aS)-6-Allyl-4-(benzo[b]thiophene-2-sulfonyl)-5-oxo-hexahydro-pyrrolo[3,2-b]pyrrole-1-carboxylic acid benzyl ester Intermediate 13 (40 mg) in tetrahydrofuran (1.5 ml) under nitrogen was cooled to 0° C. and sodium hydride (7.8 mg) was added and left to stir for half an hour. Intermediate 46 (0.046 g) was then added. After 1 h, 1 ml of dimethylformamide was added. The mixture was left for 24 h. The reaction was quenched with saturated ammonium chloride (20 ml), extracted with ethyl acetate (3×20 ml), washed with brine (20 ml) and dried (MgSO$_4$). The solvent was removed in vacuo to give a colourless oil (70 mg). This was purified by flash chromatography eluting with hexane:ether (1:1) to give the title compound as a white solid (25 mg), m.p.= 146.3–146.4° C., T.l.c. SiO$_2$ Ether/hexane, (1:1) Rf=0.31.

Example 43 rel-(3aS,6R,6aR)-6-Allyl-5-oxo-4-(2-phenyl-ethanesulfonyl)-hexahydro-pyrrolo[3,2-b]pyrrole-1-carboxylic acid benzyl ester To Intermediate 13 (44 mg) in dry bt,N-dimethylformamide (2 ml) at 0° C. under nitrogen was added sodium hydride 60% dispersion in mineral oil (70 mg), and the resulting mixture stirred for 30–40 min. 2-phenyl ethane sulfonyl chloride [Sohmiya, Hajime et al *Japan.Chem.Lett*, 1992, 5, 891] in dimethoxyethane (1 ml) was added at 0–5° C., and the resulting mixture was warmed to room temperature overnight. The reaction was quenched with saturated ammonium chloride (20 ml) and extracted with ethyl acetate (100 ml). The organic phase was washed with 8% aqueous sodium bicarbonate solution (20 ml), followed by 1M aqueous lithium chloride (2×20 ml), dried (MgSO$_4$) and evaporated in vacuo to give a white solid (200 mg). Purification by flash chromatography eluting with hexane:ethyl acetate (4:1) gave an oil (38 mg). This was triturated with hexane allowing to stand overnight to give a white solid (30 mg), which was still impure by n.m.r. Further trituration with hexane gave the title compound as a white solid (25 mg).

T.l.c SiO$_2$, hexane: ethyl acetate (4:1), Rf=0.31, Analayis Found: C,63.7; H,6.4; N,5.8% C$_{25}$H$_{28}$N$_2$O$_5$S requires: C,64.1; H,6.0; N,6.0%

Example 44 rel-(3aS,6R,6aR)-6-Allyl-5-oxo-4-(2-phenyl-(E)-ethenesulfonyl)-hexahydro-pyrrolo[3,2-b]pyrrole-1-carboxylic acid benzyl ester To Intermediate 13 (55 mg) in a mixture of dry N,N-dimethylformamide:tetrahydrofuran 4:1 (2.5 ml) at 0° C., was added sodium hydride (14 mg). The suspension was stirred at 0° C. for 1.25 h and trans-beta-styrenesulfonyl chloride (111 mg) added. Stirring was continued for 20 h allowing the mixture to slowly reach room temperature. As t.l.c. indicated that some starting lactam remained, the solution was recooled (0° C.) and further sodium hydride (10 mg) was added. After stirring for 15 min further sulfonyl chloride (98 mg) was added. The mixture was quenched with water after a further 2 h and partitioned between dilute brine and ethyl acetate (15 ml). The aqueous phase was extracted with ethyl acetate (15 ml), the combined organic phase dried (MgSO$_4$) and the solvent removed in vacuo to give a yellow oil (120 mg). This was purified by flash chromatography eluting with hexane:ethyl acetate (4:1) to give the title compound as a white solid. T.l.c. (SiO$_2$) ether, Rf=0.74, I.R. vmax; 2903, 1756, 1703, 1451, 1161, 1131 cm$^{-1}$.

Example 45 rel-(3aS,6R,6aR)-6-Allyl-4-benzenesulfonyl-5-oxo-hexahydro-pyrrolo[3,2-b]pyrrole-1-carboxylic acid benzyl ester To Intermediate 13 (49 mg) in a mixture of dry N,N-dimethylformamide and dry tetrahydrofuran 4:1(2.5 ml) cooled to 0° C. was added sodium hydride (12 mg). After 30 min at 0° C. benzenesulfonyl chloride (63 ml) was added and the mixture stirred for a further 4.5 h, allowing it to slowly warm to room temperature. The mixture was quenched with saturated ammonium chloride, extracted with ethyl acetate (2×20 ml), dried (MgSO$_4$) and the solvent removed in vacuo to give a yellow oil (85 mg). This was purified by flash chromatography eluting with hexane:ethyl acetate (4:1) to give the title compound as a white solid 37 mg). T.l.c. SiO$_2$, hexane:ethyl acetate (3:1),Rf=0.3, I.R. vmax; 2904, 1759, 1704, 1450, 1326, 1131 cm$^{-1}$.

Examples 46, 47 and 48

The above examples were prepared in a similar manner to Example 29:

rel-(3R,3aR,6aS)-1-Methanesulfonyl-4-(3-morpholin-4-yl-propionyl)-3-propyl-hexahydro-pyrrolo[3,2-b]pyrrol-2-one Prepared from Intermediate 26 and 3-morpholinopropanoic acid [K. Itoh, S. Sakai , Y. Ishii , *J. Org. Chem.*, 1966, 31, 3948], white solid, T.l.c. (7:3 ethyl acetate:methanol) Rf 0.24, Mass Spec. MH$^+$ (found) 388 MH$^+$ (calculated) 388. (Example 46)

rel-(3R,3aR,6aS)-1-Methanesulfonyl-4-(4-morpholin-4-yl-butyryl)-3-propyl-hexahydro-pyrrolo[3,2-b]pyrrol-2-one Prepared from Intermediate 26 and 4-morpholinobutanoic acid [R. K. Razdan, T. B. Zitko, H. G. Pars, N. P. Plotnikoff, P. W. Dodge, A. T. Dren, J. Kyncl, P. Somani, *J. Med. Chem.*, 1976, 2, 454], colourless oil, T.l.c. (7:3 ethyl acetate:methanol) Rf 0.27, Mass Spec. MH$^+$ (found) 402 MH$^+$ (calculated) 402. (Example 47)

rel-(3R,3aR,6aS)-1-(Naphthalene-2-sulfonyl)-3-propyl-4-(3-pyridin-2yl-propionyl)-hexahydro-pyrrolo[3,2-b]pyrrol-2-one Prepared from Intermediate 14 and 3-(2-pyridinyl)-propionic acid [A. Alberola, M. F. Brana, *An. R. Soc. Esp. Fis, Quim. Ser. B*, 1967, 63, 683], pale brown solid, T.l.c. (7:3 ethyl acetate:methanol) Rf 0.65, Mass Spec. MH$^+$ (found) 492 MH$^+$ (calculated) 492 (Example 48)

Example 49 rel-(3aS,6R,6aR)-6-Allyl-5-oxo-4-(quinoline-8-sulfonyl)-hexahydro-pyrrolo[3,2-b]pyrrole-1-carboxylic acid benzyl ester Intermediate 47 (0.212 g), 4-dimethylaminopyridine (0.076 g), 1-(3-dimethylaminopropyl)-3-ethylcarbodiimide hydrochloride (0.088 g) and dichloromethane (150 ml) were stirred at room temperature under nitrogen for 24 h. After solvent removal in vacuo the residue was redissolved in ethyl acetate and washed with water (3×25 ml), 1M hydrochloric acid (25 ml), brine (25 ml) and dried (MgSO$_4$). Solvent removal in vacuo followed by purification by flash chromatography on silica (Merck 9385) eluting with 60:40 hexane:ethyl acetate gave the title compound as a colourless oil (0.050 g). T.l.c. (1:1 hexane:ethyl acetate) Rf 0.28 Mass Spec. MH$^+$ (found) 508 MH$^+$ (calculated) 508.

Example 50 rel-(3aS,6R,6aR)-5-Oxo-6-propyl-4-(1,2,3,4-tetrahydro-quinoline-8-sulfonyl-hexahydro-pyrrolo[3,2-b]pyrrole-1-carboxylic acid benzyl ester Example 49 (0.0509), 20% palladium hydroxide (0.015 g) and ethyl acetate (10 ml) were hydrogenated for 6 h. The catalyst was then filtered off over hyflo and concentrated an vacuo. The residue was purified by flash chromatography on silica gel 9385 eluting with 4:1 hexane:ethyl acetate to afford the title compound (0.012 g) as a colourless oil. T.l.c. (1:1 ethyl acetate:hexane) Rf 0.39 Mass Spec. MH$^+$ (found) 498 MH$^+$ (calculated) 498.

Example 51 rel-(3R,3aR,6aS)-1-(Isoquinoline-5-sulfonyl)-4-methanesulfonyl-3-propyl-hexahydro-pyrrolo[3,2-b]pyrrol-2-one Prepared in a similar manner to Example 52 from Intermediate 52 to give the title compound, T.l.c. (ethyl acetate) Rf 0.18, Mass Spec. MH$^+$ (found) 438 MH$^+$ (calculated) 438.

Example 52 rel-(3R,3aR,6aS)-4-Methanesulfonyl-3-propyl-1-(quinoline-8-sulfonyl)-hexahydro-pyrrolo[3,2-b]pyrrol-2-one Intermediate 54 (0.180 g—crude material contaminated with sodium chloride), diisopropylethylamine (0.03 ml), 2-chloro-1-methylpyridinium iodide (0.049 g) and dichloromethane (75 ml) were mixed in a stoppered flask for 2 h at room temperature. Further diisopropylethylamine (0.10 ml) was then added and the mixture stirred for a further 24 h. The solvent was removed in vacuo and the residue purified by flash chromatography on silica (Merck 9385) eluting with hexane:ethyl acetate (1:1). The title compound was obtained as a white solid (0.013 g). T.l.c. (ethyl acetate:hexane, 2:1) Rf 0.31. Mass Spec. MH$^+$ (found) 438 MH$^+$ (calculated) 438.

Example 58 rel-(3R,3aR,6aS)-1-Methanesulfonyl-4-(6-morpholin-4-yl-hexanoyl)-3-propylhexahydro-pyrrolo[3,2-b]pyrrol-2-one 2,3-dihydroxysuccinate Prepared in a similar manner to Example 39 from Intermediate 26 and 6-morpholin-4-yl-hexanoic acid to give the title compound as a cream solid. T.l.c. (Ethyl acetate:methanol 6:4) Rf 0.31 Mass spec. MH$^+$ (found) 430 MH$^+$ (calculated) 430.

Example 60 rel-(3R,3aR,6aS)-4-(6-Azepin-1-yl-hexanoyl-3-isopropyl-1-methanesulfonyl)-hexahydro-pyrrolo[3,2-b]pyrrol-2-one hydrochloride Prepared in a similar manner to Example 61 from Intermediate 86 to give the title compound as a cream solid. Data for free base T.l.c. (100:8:1 dichloromethane:ethanol:ammonia) Rf 0.14 Mass spec MH$^+$ (found) 442 MH$^+$ (calculated) 442.

Example 61 rel-(3R,3aR,6aS)-3-isopropyl-1-methanesulfonyl-4-(3-piperidin-1yl-propionyl- hexahydro-pyrrolo[3,2-b]pyrrol-2-one hydrochloride Intermediate 86 (0.04 g), piperidinepropanoic acid (0.028 g), di-isopropylethylamine (0.085 ml), bromo-tris-pyrrolidine-phosphonium hexafluorophosphate (0.083 g) and dichloromethane (3 ml) were mixed for 4 h. The mixture was diluted with ethyl acetate and washed with water and brine and dried (MgSO$_4$). Solvent removal in vacuo followed by flash chromatography on silica 9385 eluting with ethyl acetate:methanol gave an oil (41 mg). This material was dissolved in dichloromethane (3 ml) and 1M hydrogen chloride in ether (0.5 ml) added. The solvents were removed and the solid triturated in diethyl ether to give the title compound (0.045 g) as a cream solid. Data for free base T.l.c. (7:3 ethyl acetate:methanol+trace ammonia) Rf 0.31 Mass spec MH$^+$ (found) 386 MH$^+$ (calculated) 386.

Example 62 rel-(3R,3aR,6aS)-1-Methanesulfonyl-1-4-(4-piperidin-1-ylmethyl-benzoyl)-3-propyl-hexahydro-pyrrolo[3,2-b]pyrrol-2-one To a stirring solution of Intermediate 87 (98 mg) in dichloromethane (7 ml) was added glacial acetic acid (34.5 µl), sodium triacetoxy borohydride (88.2 mg) then piperidine (36 µl). The resulting acted with distilled water (2×25 ml), dried (Na$_2$SO$_4$), filtered and concentrated in vacuo to give a yellow gum. Purification by flash chromatography eluting with triethylamine: ethyl acetate (3:97) resulted in fractions which were concentrated in vacuo to give a white foam. The foam was dissolved in tetrahydrofuran (1 ml) and diethyl either (10 ml). To this solution was added 1M HCl/diethyl ether (300 µl). The solvent was removed in vacuo to give the title compound as a free flowing white solid (76 mg). Data for free base T.l.c. 88:10:2; Ethyl acetate:Methanol:Triethylamine Rf 0.32 Mass spec MH+ (found) 448 MH+ (calculated) 448.

Example 63
rel-N-[4-(4-Methanesulfonyl-5-oxo-6R-propyl-hexahydro-(3aS,6aR)-pyrrolo[3,2-b]pyrrole-1-sulfonyl)phenyl]-acetamide N-Acetylsulfanilyl chloride (81 mg) was added to a stirred solution of the hydrochloride salt of Intermediate 26 (75 mg) and triethylamine (0.185 ml) in dry DCM (3 ml) under nitrogen. After 1 h. the reaction mixture was partitioned between ethyl acetate and brine. The organic layer was separated, dried (Na$_2$SO$_4$) and concentrated in vacuo. The residue was recrystallised from methanol to give the title compound as a white solid (86 mg). T.l.c. (9:1 chloroform:methanol) 0.53 Mass spec MNH$_4$+(found) 461MNH$_4$+(calculated) 461

Example 64
rel-(3R,3aR,6aS)-1-Methanesulfonyl-4-(10-morpholin-4-yl-decanoyl)-3-propyl-hexahydro-pyrrolo[3,2-b]pyrrol-2-one DL-tartrate To a stirred solution of Intermediate 89 (100 mg) in dichloromethane (1 ml) was added acetic acid (0.1 ml) followed by morpholine (23 μl). The solution was stirred for 2 minutes before sodium triacetoxyborohydride (76.3 mg), was added and the resulting mixture stirred for 30 minutes. The mixture was partitioned between ethyl acetate (50 ml) and 8% aqueous sodium bicarbonate solution. The phases were separated, the aqueous phase further extracted with ethyl acetate (50 ml), the combined organic phases dried (MgSO$_4$) and the solvent evaporated in vacuo to leave a colourless gum. The gum was purified by flash chromatography eluting with dichloromethane:methanol (9:1) to give a colourless gum. This was dissolved in ethanol (2 ml) and a solution of (DL)-tartaric acid (26 mg) in ethanol (2 ml) was added. The solution was evaporated to dryness and the residue was triturated with ether and filtered to give the title compound as a white foam (102.5 mg). MH+ (found, thermospray +ve)=486 MH+ (calculated)=486 T.l.c. SiO$_2$ (9:1 dichloromethane:ethanol) R.f=0.46.

Examples 65–72

The above Examples were prepared in a similar manner to Example 64 from Intermediate 89.
rel-(3R,3aR,6aS)-4-(10-Diethylamino-decanoyl)-1-methanesulfonyl-3-propyl-hexahydro-pyrrolo[3,2-b]pyrrol-2-one DL-tartrate T.l.c. (4:1 Dichloromethane:Methanol) Rf 0.20 Mass spec. (found) MH+=472, (calc.) MH+=472. (Example 65)
rel-(3R,3aR,6aS)-4-(10-Azepin-1-yl-decanoyl)-1-methanesulfonyl-3-propyl-hexahydro-pyrrolo[3,2-b]pyrrol-2-one hydrochloride T.l.c. (100:8:1 Dichloromethane:Ethanol:0.880 Ammonia) Rf 0.45 Mass spec. (found) MH+=498, (calc.) MH+=498. (Example 66)
rel-(3R,3aR,6aS)-4-(10-Dimethylamino-decanoyl)-1-methanesulfonyl-3-propyl-hexahydro-pyrrolo[3,2-b]pyrrol-2-one DL-tartrate T.l.c. (4:1 Dichloromethane:Methanol) Rf 0.16 Mass spec. (found) MH+=444, (calc.) MH+=444. (Example 67)
rel-(3R,3aR,6aS)-1-Methanesulfonyl-4-[10-methyl-phenyl-amino)decanoyl]-3-propyl-hexahydro-pyrrolo[3,2-b]pyrrol-2-one hydrochloride T.l.c. (1:1 Ethyl acetate:Cyclohexane) Rf 0.5 Mass spec. (found) MH+=506, (calc.) MH+=506 (Example 68)

rel-(3R,3aR,6aS)-1-Methanesulfonyl-4-[10-(4-methyl-piperazin-1-yl)-decanoyl]-3-propyl-hexahydro-pyrrolo[3,2-b]pyrrol-2-one dihydrochloride T.l.c. (9:1 Dichloromethane:Methanol) Rf 0.20 Mass spec. (found) MH+=499, (calc.) MH+=499. (Example 69)
rel-(3R,3aR,6aS)-1-Methanesulfonyl-4-(10-piperidin-1-yl-decanoyl)-3-propyl-hexahydro-pyrrolo[3,2-b]pyrrol-2-one DL-tartrate T.l.c. (9:1 Dichloromethane:Methanol) Rf 0.39 Mass spec. (found) MH+=484, (calc.) MH+=484. (Example 70)
rel-(3R,3aR,6aS)-1-Methanesulfonyl-3-propyl-4-(10-pyrrolidin-1-yl-decanoyl)-hexahydro-pyrrolo[3,2-b]pyrrol-2-one hydrochloride T.l.c. (100:8:1 Dichloromethane:Ethanol:0.880 Ammonia) Rf 0.45 Mass spec. (found) MH+=470, (calc.) MH+=470. (Example 71)
rel-(3R,3aR,6aS)-4-(10-Azetidin-1-yl-decanoyl)-1-methanesulfonyl-3-propyl-hexahydro-pyrrolo[3,2-b]pyrrol-2-one DL-tartrate T.l.c. (5:1 Dichloromethane:Methanol) Rf 0.45 Mass spec. (found) MH+=456, (calc.) MH+=456. (Example 72)

Examples 73–81

The above Examples were prepared in a similar manner to Example 64 from Intermediate 90.
rel-(3R,3aR,6aS)-1-Methanesulfonyl-3-propyl-4-(6-pyrrolidin-1-yl-hexanoyl)-hexahydro-pyrrolo[3,2-b]pyrrol-2-one hydrochloride T.l.c. (100:8:1 Dichloromethane:Ethanol:0.880 Ammonia) Rf 0.23 Mass spec. (found) MH+=414, (calc.) MH+=414. (Example 73)
rel-(3R,3aR,6aS)-1-Methanesulfonyl-4-(6-piperidin-1-yl-hexanoyl)-3-propyl-hexahydro-pyrrolo[3,2-b]pyrrol-2-one hydrochloride T.l.c. (4:1 Dichloromethane:Methanol) Rf 0.59 Mass spec. (found) MH+=428, (calc.) MH+=428. (Example 74)
rel-(3R,3aR,6aS)-4-(6-8-Aza-bicyclo[3.2.1]oct-8-yl-hexanoyl)-1-methanesulfonyl-3-propyl-hexahydro-pyrrolo[3,2-b]pyrrol-2-one hydrochloride T.l.c. (50:8:1 Dichloromethane:Ethanol:0.880 Ammonia) Rf 0.7 Mass spec. (found) MH+=454, (calc.) MH+=454. (Example 75)
rel-(3R,3aR,6aS)-4-(6-Diethylamino-hexanoyl)-1-methanesulfonyl-3-propyl-hexahydro-pyrrolo[3,2-b]pyrrol-2-one DL-tartrate T.l.c. (4:1 Dichloromethane:Methanol) Rf 0.10 Mass spec. (found) MH+=416, (calc.) MH+=416. (Example 76)
rel-(3R,3aR,6aS)-4-(6-Dimethylamino-hexanoyl)-1-methanesulfonyl-3-propyl-hexahydro-pyrrolo[3,2-b]pyrrol-2-one DL-tartrate T.l.c. (4:1 Dichloromethane:Methanol) Rf 0.1 Mass spec. (found) MH+=388, (calc.) MH+=388. (Example 77)
rel-(3R,3aR,6aS)-4-(6-Azetidin-1-yl-hexanoyl)-1-methanesulfonyl-3-propyl-hexahydro-pyrrolo[3,2-b]pyrrol-2-one DL-tartrate T.l.c.(4:1 Dichloromethane:Methanol) Rf 0.45 Mass spec. (found) MH+400, (calc.) MH+=400. (Example 78)
rel-(3R,3aR,6aS)-1-Methanesulfonyl-4-[6-(4-methyl-piperazin-1-yl)-hexanoyl]-3-propyl-hexahydro-pyrrolo[3,2-b]pyrrol-2-one dihydrochloride T.l.c. (9:1 Dichloromethane:Methanol) Rf 0.17 Mass spec. (found) MH+=443, (calc.) MH+=443. (Example 79)
rel-(3R,3aR,6aS)-1-Methanesulfonyl-4-[6-(4-methyl-[1,4]diazepin-1-yl)-hexanoyl]-3-propyl-hexahydro-pyrrolo[3,2-b]pyrrol-2-one hydrochloride T.l.c. (60:8:1Dichloromethane:Ethanol:0.880 Ammonia) Rf 0.33 Mass spec. (found) MH+457, (calc.) MH+=457. (Example 80)

rel-(3R,3aR,6aS)-1-Methanesulfonyl-4-[6-(methyl-phenyl-amino)-hexanoyl]-3-propyl-hexahydro-pyrrolo[3,2-b]pyrrol-2-one hydrochloride T.l.c. (1:1 Ethyl acetate:Cyclohexane) Rf 0.4 Mass spec. (found) MH$^+$=450, (calc.) MH$^+$=450. (Example 81)

Examples 82–89

The above Examples were prepared in a similar manner to Example 64 from Intermediate 91.

rel-(3R,3aR,6aS)-1-Methanesulfonyl-4-[4-(4-methyl-piperazin-1-yl)-butyryl]-3-propyl-hexahydro-pyrrolo[3,2-b]pyrrol-2-one dihydrochloride T.l.c. (9:1 Dichloromethane:Methanol) Rf 0.1 Mass spec. (found) MH$^+$=415, (calc.) MH$^+$=415. (Example 82)

rel-(3R,3aR,6aS)-4-(4-Diethylamino-butyryl)-1-methanesulfonyl-3-propyl-hexahydro-pyrrolo[3,2-b]pyrrol-2-one DL-tartrate T.l.c. (4:1 Dichloromethane:Methanol) Rf 0.24 Mass spec. (found) MH$^+$=388, (calc.) MH$^+$=388. (Example 83)

rel-(3R,3aR,6aS)-4-(4-Azetidin-1-yl-butyryl)-1-methanesulfonyl-3-propyl-hexahydro-pyrrolo[3,2-b]pyrrol-2-one DL-tartrate T.l.c. (9:1 Dichloromethane:Methanol) Rf 0.17 Mass spec. (found) MH$^+$=372, (calc.) MH$^+$=372. (Example 84)

rel-(3R,3aR,6aS)-4-(4-Dimethylamino-butyryl)-1-methanesulfonyl-3-propyl-hexahydro-pyrrolo[3,2-b]pyrrol-2-one DL-tartrate T.l.c. (4:1 Dichloromethane:Methanol) Rf 0.12 Mass spec. (found) MH$^+$=360, (calc.) MH$^+$=360. (Example 85)

rel-(3R,3aR,6aS)-4-(4-Azepin-1-yl-butyryl)-1-methanesulfonyl-3-propyl-hexahydro-pyrrolo[3,2-b]pyrrol-2-one hydrochloride T.l.c. (100:8:1 Dichloromethane:Ethanol:0.880 Ammonia) Rf 0.25 Mass spec. (found) MH$^+$=414, (calc.) MH$^+$=414. (Example 86)

rel-(3R,3aR,6aS)-1-Methanesulfonyl-4-(4-piperidin-1-yl-butyryl)-3-propyl-hexahydro-pyrrolo[3,2-b]pyrrol-2-one DL-tartrate T.l.c. (7:1 Dichloromethane:Methanol) Rf 0.35 Mass spec. (found) MH$^+$=400, (calc.) MH$^+$=400. (Example 87)

rel-(3R,3aR,6aS)-1-Methanesulfonyl-4-[4-(methyl-phenyl-amino)-butyryl]-3- propyl-hexahydro-pyrrolo[3,2-b]pyrrol-2-one hydrochloride T.l.c. (1:1 Ethyl acetate:Cyclohexane) Rf 0.3 Mass spec. (found) MH$^+$=422, (calc.) MH$^+$=422. (Example 88)

rel-(3R,3aR,6aS)-1-Methanesulfonyl-3-propyl-4-(4-pyrrolidin-1-yl-butyryl)-hexahydro-pyrrolo[3,2-b]pyrrol-2-one hydrochloride T.l.c. (100:8:1 Dichloromethane:Ethanol:0.880 Ammonia) Rf 0.35 Mass spec. (found) MH$^+$=386, (calc.) MH$^+$=386. (Example 89)

Examples 90–92

The above Examples were prepared in a similar manner to Example 2, from Intermediate 26.

rel-(3R,3aR,6aS)-4-(3-Dimethylamino-propionyl)-1-methanesulfonyl-3-propyl-hexahydro-pyrrolo[3,2-b]pyrrol-2-one hydrochloride T.l.c. (100:8:1 Dichloromethane:Ethanol:0.880 Ammonia) Rf 0.28 Mass spec. (found) MH$^+$=346, (calc.) MH$^+$=346. (Example 90)

rel-(3R,3aR,6aS)-4-(3-Diethylamino-propionyl)-1-methanesulfonyl-3-propyl-hexahydro-pyrrolo-3,2-b]pyrrol-2-one hydrochloride T.l.c. (100:8:1 Dichloromethane:Ethanol:0.880 Ammonia) Rf 0.35 Mass spec. (found) MH$^+$=374, (calc.) MH=374. (Example 91)

rel-(3R,3aR,6aS)-4-[3-(2,6-Dimethyl-piperidin-1-yl)-propionyl]-1-methanesulfonyl-3-propyl-hexahydro-pyrrolo[3,2-b]pyrrol-2-one hydrochloride T.l.c. (free base) (4:1 chloromethane:Methanol) Rf 0.48 Mass spec. (found) MH$^+$=414, (calc.) MH$^+$=414. (Example 92)

Example 93 rel-(3R,3aR,6aS)-1-Methanesulfonyl-3-propyl-4-(3-pyrrolidin-1-yl-propionyl)-hexahydro-pyrrolo[3,2-b]pyrrol-2-one hydrochloride A solution of 3-bromopropionyl chloride (140 mg) in dichloromethane (1 ml) was added in a stream to a stirred solution of Intermediate 26 (60 mg) and triethylamine (135 mg) in dichloromethane (10 ml). The reaction mixture was stirred at room temperature for 1.25 hours then treated with a solution of pyrrolidine (100 mg) in dichloromethane (1 ml). The reaction mixture was stirred at room temperature for 2 hours; left to stand at room temperature for 6 days and diluted with dichloromethane (20 ml). The reaction mixture was washed with 8% sodium bicarbonate (15 ml) and water (15 ml), dried (Na$_2$SO$_4$) and concentrated to give a gum (100 mg). A solution of the gum in a (1:1) mixture of ether and ethyl acetate (12 ml) was treated with a 4.0M solution of hydrogen chloride in dioxan (0.25 ml), with rigorous stirring, to give a suspension. The solvents were decanted. The residue was washed with ethyl acetate (2×10 ml) then partitioned between ethyl acetate (2×15 ml) and 8% sodium bicarbonate (10 ml). The combined organics were washed with water (15 ml), dried (Na$_2$SO$_4$), filtered and concentrated to give a gum (42 mg). A solution of the gum in ethyl acetate (15 ml) was stirred and treated with a 0.4M solution of ethereal hydrogen chloride (0.7 ml). The solvent was decanted to leave a semi-solid. The semi-solid was triturated in ethyl acetate (2 ml). The solvent was decanted and the residue dried in vacuo to give the title compound (31 mg) as a white powder. m.p. 160–165° C. Mass sec. MH$^+$ found)= 372 MH$^+$ (calculated)=372 Microanalysis found: C, 49.8; H, 7.3; N, 10.01; S, 7.5 requires: C, 50.05; H, 7.4; N, 10.3; S, 7.9%.

Example 94 rel-(3R,3aR,6aS)-1-Methanesulfonyl-4-[3-(4-methyl-piperazin-1-yl)-propionyl]-3-propyl-hexahydro-pyrrolo[3,2-b]pyrrol-2-one dihydrochloride A solution of Intermediate 92 (60 mg) and 1-methylpiperazine (29 mg) in acetonitrile (6 ml) was stirred at room temperature for 42 hours; more 1-methylpiperazine (15 mg) being added after 18 hours. The solvent was removed in vacuo. The residual gum was chromatographed on silica (Merck 9385), using a mixture of dichloromethane, ethanol and ammonia (125:10:4) as the eluent, to give a gum. A solution of the gum in diethyl ether (10 ml) was treated, with stirring, with a solution of 4M hydrogen chloride in dioxan (0.15 ml). The solvent was decanted and the residual solid was dried in vacuo to give the title compound (83 mg) as a white powder. m.p. 144–150° C. Mass spec MH+ (found)=401 MH+ (calculated)=401 T.l.c. Silica (dichloromethane:ethanol:ammonia 100:8:1) R.f= 0.12.

Examples 95–97

The above Examples were prepared in a similar manner to Example 29 from Intermediate 26.

rel-4-(4-Methanesulfonyl-5-oxo-6R-propyl-hexahydro-(3aS,6aR)-pyrrolo[3,2-b]pyrrol-1-yl)-4-oxo-butyramide Mass spec (found) MH$^+$=346, (calc.) MH$^+$=346 I.R. $v_{max}$ 1748, 1653, 1353, 1139 cm$^{-1}$. (Example 95)

rel-N-[3-(4-Methanesulfonyl-5-oxo-6R-propyl-hexahydro-(3aS,6aR)-pyrrolo[3,2-b]pyrrol-1-yl)-3-oxo-propyl]-acetamide T.l.c. (19:1 Dichloromethane:Methanol) Rf 0.13 Mass spec. (found) MH+=360, (calc.) MH+=360. (Example 96)
rel-(3R,3aR,6aS)-4-(3-Azetidin-1-yl-propionyl)-1-methanesulfonyl-3-propyl-hexahydro-pyrrolo[3,2-b]pyrrol-2-one hydrochloride T.l.c. (free base)(100:10:1 Dichloromethane:Ethanol:0.880 Ammonia) Rf 0.15 Mass spec. found) MH+=358, (calc.) MH+=358. (Example 97)

Examples 98–99

The above Examples were prepared in a similar manner to Example 94, from Intermediate 92.
rel-(3R,3aR,6aS)-1-[3-(4-Methanesulfonyl-5-oxo-6-propyl-hexahydro-pyrrolo[3,2-b]pyrrol-1-yl)-3-oxo-propyl]-piperidine-4-carboxylic acid amide hydrochloride T.l.c. (100:10:1 dichloromethane:Ethanol:0.880 Ammonia) Rf 0.75 Mass spec. (found) MH+=429, (calc.) MH+=429. (Example 98)
rel-(3R,3aR,6aS)-4-(3-Azepin-1-yl-propionyl)-1-methanesulfonyl-3-propyl-hexahydro-pyrrolo[3,2-b]pyrrol-2-one hydrochloride T.l.c. (free base) (100:10:1 Dichloromethane:Ethanol:0.880 Ammonia) Rf 0.60 Mass spec. (found) MH+=400, (calc.) MH+=400. (Example 99)

Examples 100–105, 107–108

The above Examples were prepared in a similar manner to Example 2, from Intermediate 26.
rel-(3R,3aR,6aS)-1-Methanesulfonyl-4-(piperidin-1-yl-acetyl)-3-propyl-hexahydro-pyrrol[3,2-b]pyrrol-2-one hydrochloride Mass spec. (free base) (found) MH+=372, (calc.) MH+=372. (Example 100)
rel-(3R,3aR,6aS)-4-Diethylaminoacetyl-1-methanesulfonyl-3-propyl-hexahydro-pyrrolo[3,2-b]pyrrol-2-one hydrochloride Mass spec. (found) MH+=360, (calc.) MH+=360 I.R. $v_{max}$ 1748, 1673, 1353, 1161 cm$^{-1}$. (Example 101)
rel-(3R,3aR,6aS)-4-Dimethylaminoacetyl-1-methanesulfonyl-3-propyl-hexahydro-pyrrolo[3,2-b]pyrrol-2-one hydrochloride Mass spec. (found) MH+=332, (calc.) MH+=332 I.R. $v_{max}$ 1729, 1644, 1368, 1145 cm$^{-1}$. (Example 102)
rel-(3R,3aR,6aS)-1-Methanesulfonyl-4-[(methyl-phenyl-amino)-acetyl]-3-propyl-hexahydro-pyrrolo[3,2-b]pyrrol-2-one hydrochloride Mass spec. (found) MH+=394 (calc.) MH+=394 I.R. $v_{max}$ 1748, 1675, 1355, 1149 cm$^{-1}$. (Example 103)
rel-(3R,3aR,6aS)-4-Azepin-1-yl-acetyl)-1-methanesulfonyl-3-propyl-hexahydro-pyrrolo[3,2-b]pyrrol-2-one hydrochloride Mass spec. (found) MH+=386, (calc.) MH+=386 I.R. $v_{max}$ 1746, 1672, 1354, 1149 cm$^{-1}$. (Example 104)
rel-(3R,3aR,6aS)-1-Methanesulfonyl-4-[(4-methyl-piperazin-1-yl)-acetyl]-3-propyl-hexahydro-pyrrolo[3,2-b]pyrrol-2-one hydrochloride Mass spec. (free base)(found) MH+=387, (calc.) MH+=387 I.R. $v_{max}$ 1779 cm$^{-1}$. (Example 105)
rel-(3R,3aR,6aS)-1-Methanesulfonyl-4-morpholin-4-yl-acetyl)-3-propyl-hexahydro-pyrrolo[3,2-b]pyrrol-2-one hydrochloride Mass spec. (free base) (found) MH+=374(calc.) MH+=374 I.R. $v_{max}$ 1780 cm$^{-1}$. (Example 107)

rel-(3R,3aR,6aS)-1-Methanesulfonyl-4-morpholin-4-yl-acetyl)-3-propyl-hexahydro-pyrrolo[3,2-b]pyrrol-2-one hydrochloride Mass spec. (free base)(found) MH+=358 (calc.) MH+=358. (Example 108)

Example 109

The above Example was prepared in a similar manner to Example 17, from Intermediate 93.
rel-(3R,3aR,6aS)-4-Aminoacetyl-1-methanesulfonyl-3-propyl-hexahydro-pyrrolo[3,2-b]pyrrol-2-one trifluoroacetate Mass spec. (found) MH+=304 (calc.) MH+=304 I.R. $v_{max}$ 1744, 1680, 1363, 1147 cm$^{-1}$.

Example 110

The above Example was prepared in a similar manner to Example 17, from Intermediate 94.
rel-(3R,3aR,6aS)-1-Methanesulfonyl-4-methylaminoacetyl-3-propyl-hexahydro-pyrrolo[3,2-b]pyrrol-2-one trifluoroacetate Mass spec. (found) MH+=318 (calc.) MH+=318.

Examples 111–114, 120

The above Examples were prepared in a similar manner to Example 29 from Intermediate 26.
rel-(3R,3aR,6aS)-1-Methanesulfonyl-4-(1-methyl-pyrrolidine-2-carbonyl)-3-propyl-hexahydro-pyrrolo[3,2-b]pyrrol-2-one Mass spec. (found) MH+=358 (calc.) MH+=358. (Example 111)
rel-(3R,3aR,6aS)-1-Methanesulfonyl-4-[(2-oxo-2H-pyridin-1-yl)-acetyl]-3-propyl-hexahydro-pyrrolo[3,2-b]pyrrol-2-one Mass spec. (found) MH+=382 (calc.) MH+=382. (Example 112)
rel-(3R,3aR,6aS)-1-Methanesulfonyl-4-[(4-oxo-4H-pyridin-1-yl)-acetyl]-3-propyl-hexahydro-pyrrolo[3,2-b]pyrrol-2-one (Example 113)
rel-N-[2-(4-Methanesulfonyl-5-oxo-6R-propyl-hexahydro-(3aS,6aR)-pyrrolo[3,2-b]pyrrol-1-yl)-2-oxo-ethyl]-acetamide Assay Found: C,48.35; H,6.95; N,11.89; S,9.03% $C_{14}H_{23}N_3O_5S$ requires C,48.68; H,6.71; N,12.16; S,9.28%. (Example 114)
rel-N-[4-(4-Methanesulfonyl-5-oxo-6R-propyl-hexahydro-(3aS,6aR)-pyrrolo[3,2-b]pyrrole-1-carbonyl)-phenyl]-acetamide White solid T.L.C (methanol:chloroform 1:9) Rf 0.54 Mass spec MH+ (found) 408 MH+ (calculated) 408. (Example 120)

Example 115

(3R,3aR,6aS)-4-(6-Azepin-1-yl-hexanoyl)-1-methanesulfonyl-3-propyl-hexahydro-pyrrolo[3,2-b]pyrrol-2-one hydrochloride Intermediate 108 (30 mg), 1-hydroxybenzotriazole (33 mg), 1-(3-dimethylaminopropyl)-3-ethylcarbodiimide hydrochloride (47 mg), 6-azepin-1-yl-hexanoic acid (34 mg) and acetonitrile (5 ml) were stirred at room temperature. After 4 hours the solvent was removed in vacuo and the resultant yellow gum was partitioned between saturated aqueous sodium bicarbonate solution (5 ml) and dichloromethane (15 ml). The resultant organic phase was extracted with water (2×5 ml), dried (Na$_2$SO$_4$), filtered and the solvent removed in vacuo to afford a crude yellow gum.

Purification by flash chromatography (SiO$_2$ Merck, 9385) eluting with dichloromethane:ethanol: 0.880 ammonia solution (100:8:1) produced a white crystalline solid (51 mg) which was treated with 1.0M hydrogen chloride in diethyl ether to afford the title compound as a white solid (48 mg). T.L.C (of free base) (DCM:ethanol:ammonia 75:8:1) Rf 0.46 Mass spec MH$^+$ (found) 442 MH$^+$ (calculated) 442.

Example 116

(3R,3aR,6aS)-1-Methanesulfonyl-4-(3-piperidin-1-yl-propionyl)-3-propyl-hexahydro-pyrrolo[3,2-b]pyrrol-2-one hydrochloride Intermediate 108 (30 mg), 1-hydroxybenzotriazole (33 mg), 1-(3-dimethylaminopropyl)-3-ethylcarbodiimide hydrochloride (47 mg), 1-piperidine propionic acid (25 mg) and acetonitrile (5 ml) were stirred at room temperature. After 18 hours the solvent was removed in vacuo and the residue was partitioned between a saturated aqueous solution of sodium bicarbonate (5 ml) and dichloromethane (15 ml). The organic phase was extracted with water (2×5 ml), dried (Na$_2$SO$_4$), filtered and the solvent removed in vacuo to afford a crude yellow gum. Purification by flash chromatography (SiO$_2$ Merck 9385) produced a white solid which was treated with 1.0M hydrogen chloride in diethyl ether to afford the title compound as yellow powder (29 mg). T.L.C (of free base) (DCM:ethanol:ammonia 75:8:1) Rf 0.49 Mass spec MH$^+$ (found) 386 MH$^+$ (calculated) 386.

Examples 117–118

The above Examples were prepared in a similar manner to Example 115 from Intermediate 110.
(3S,3aS,6aR)-4-(6-Azepin-1-yl-hexanoyl)-1-methanesulfonyl-3-propyl-hexahydro-pyrrolo[3,2-b]pyrrol-2-one hydrochloride Circular Dichroism: $\lambda_{max}$207.8 nm ($\Delta$E −0.79 M$^{-1}$cm$^{-1}$) and $\lambda_{max}$225.2 nm ($\Delta$E +2.15 M$^{-1}$cm$^{-1}$) (MeCN) Mass spec. (found) MH$^+$=442, (calc) MH$^+$=442. (Example 117)
(3S,3aS,6aR)-1-Methanesulfonyl-4-(3-piperidin-1-yl-propionyl)-3-propyl-hexahydro-pyrrolo[3,2-b]pyrrol-2-one hydrochloride Circular Dichroism: $\lambda_{max}$223.8 nm ($\Delta$E +2.31 M$^{-1}$cm$^{-1}$) (MeCN) Mass spec. (found) MH$^+$=386, (calc) MH$^+$=386. (Example 118)

Example 119 rel-(3R,3aR,6aS)-1-Methanesulfonyl-4-[4-(piperidine-1-carbonyl)-benzenesulfonyl]-3-propyl-hexahydro-pyrrolo[3,2-b]pyrrol-2-one Example 122 (40 mg), 1-hydroxybenzotriazole (38 mg), 1-(3-dimethylaminopropyl)-3-ethylcarbodiimide hydrochloride (54 mg), piperidine (24.0 µl) and acetonitrite (10 ml) were stirred at room temperature. After 72 hours the solvent was removed in vacuo and the residue partitioned between a saturated aqueous sodium bicarbonate solution (15 ml) and dichloromethane (15 ml). The aqueous phase was extracted with dichloromethane (15 ml). The organic extracts were combined, washed with water (15 ml), then hydrochloric acid (15 ml), dried (MgSO$_4$), filtered and the solvent removed in vacuo to afford the title compound as a white solid (22 mg). T.L.C (6% methanol:chloroform) Rf 0.65 Mass spec MH$^+$ (found) 498 MH$^+$ (calculated) 498.

Example 121 rel-4-(4-Methanesulfonyl-5-oxo-6R-propyl-hexahydro-(3aS,6aR)-pyrrolo[3,2-b]pyrrole-1-sulfonyl)-N-(2-piperidin-1-yl-ethyl)-benzamide hydrochloride Example 122 (50 mg), 1-hydroxybenzotriazole (31 mg), 1-(3-dimethylaminopropyl)-3-ethylcarbodiimide hydrochloride (44 mg) and acetonitrile (10 ml) were stirred at room temperature for 1½ hours after which time 1-(2-aminoethyl)-piperidine (25 µl) was added. After 1 hour the solvent was removed in vacuo and the resultant white residue partitioned between dichloromethane (50 ml) and water (50 ml). The organic phase was washed with a saturated aqueous solution of sodium chloride (50 ml), dried (MgSO$_4$), filtered and concentrated in vacuo to afford a crude residue which was purified by flash chromatography (SiO$_2$ Merck, 9385) to give a white solid (29 mg). This solid was combined with material from a similar experiment, and treated with 1.0M hydrogen chloride in diethyl ether to afford the title compound as a white/yellow powder (36 mg). T.L.C (of free base) (MeOH:DCM 10:90) Rf 0.37 Mass spec MH$^+$ (found) 541 MH$^+$ (calculated) 541

Example 122 rel-(3aS,6R,6aS)-4-(4-Methanesulfonyl-5-oxo-6-propyl-hexahydro-pyrrolo[3,2-b]pyrrole-1-sulfonyl)-benzoic acid Intermediate 26 (300 mg), triethylamine (680 µl), 4-(chlorosulphonyl)benzoic acid (350 mg) and dichloromethane (15 ml) were stirred at room temperature under an atmosphere of nitrogen. After 2 hours the reaction mixture was partitioned between dichloromethane (120 ml) and a saturated aqueous solution of sodium chloride. The organic layer was separated, dried (MgSO$_4$), filtered and concentrated in vacuo to a cream powder. Purification by flash chromatography(SiO$_2$ Merck, 9385) eluting with acetonitrile:acetic acid:dichloromethane (5:1:94) afforded the title compound as a white crystalline solid (213 mg). T.L.C (10% methanol:dichloromethane) Rf 0.43 Mass spec MH$^+$ (found) 431 MH$^+$ (calculated) 431.

Examples 123, 127

The above Examples were prepared in a similar manner to Example 121 from Example 122.
rel-N-(2-Dimethylamino-ethyl)-4-(4-methanesulfonyl-5-oxo-6R-propyl-hexahydro-(3aS,6aR)-pyrrolo[3,2-b]pyrrole-1-sulfonyl)-benzamide hydrochloride White solid T.L.C (dichloromethane:ethanol:ammonia 75:8:1) Rf 0.51 Mass spec MH$^+$ (found) 501 MH$^+$ (calculated 501) (Example 123)
rel-(3R,3aR,6aS)-1-Methanesulfonyl-4-[4-(4-methyl-piperazine-1-carbonyl)-benzenesulfonyl]-3-propyl-hexahydro-pyrrolo[3,2-b]pyrrol-2-one hydrochloride Yellow solid T.L.C (of free base) (methanol:chloroform 6:94) Rf 0.33 Mass spec MH$^+$ (found) 513 MH$^+$ (calculated 513) (Example 127)

Examples 124–126

The above Examples were prepared in a similar manner to Example 119 from Example 122.
rel-(3aS,6R,6aR)-4-(4-Methanesulfonyl-5-oxo-6-hexahydro-pyrrolo[3,2-b]pyrrole-1-sulfonyl)-N-methyl-benzamide Yellow solid, T.L.C (methanol:chloroform 6:94) Rf 0.43 Mass spec MH$^+$ (found ) 444 MH$^+$ (calculated) 444. (Example 124)
rel-N-Cyclopropyl-4-(4-methanesulfonyl-5-oxo-6R-propyl-hexahydro-(3aS,6aR)-pyrrolo[3,2-b]pyrrole-1-sulfonyl)-benzamide White solid T.L.C (methanol:chloroform 6:94) Rf 0.49 Mass spec MNH$_4^+$ (found) 487 MNH$_4^+$ (calculated) 487. (Example 125)
rel-4-(4-Methanesulfonyl-5-oxo-6R-propyl-hexahydro-(3aS,6aR)-pyrrolo[3,2-b]pyrrole-1-sulfonyl)-N,N-dimethyl-benzamide

Example 128
rel-(3R,3aR,6aS)-4-(4-Methanesulfonyl-5-oxo-6-propyl-hexahydro-pyrrolo[3,2-b]pyrrole-1-yl)-4-oxo-but-2E-enoic acid ethyl ester A solution of Intermediate 26 (400 mg), fumaric acid monoethyl ester (346 mg), 1-hydroxybenzotriazole (324 mg) and 1-(3-dimethylaminopropyl)-3-ethylcarbodiimide hydrochloride (460 mg) in dry dimethylformamide (2 ml) was stirred at room temperature for 16 hours. Sodium bicarbonate (8%, 40 ml) was added and the reaction mixture was extracted with ethyl acetate (50 ml). The organic extract was washed with water (3×50 ml), dried ($Na_2SO_4$), filtered and concentrated in vacuo to give a solid. The solid was triturated in ether (25 ml), filtered off and dried in vacuo to give the title compound as a cream powder (486 mg). Melting point 184–185° Mass spec $MH^+$ (found)=373 $MH^+$ (calculated)=373.

Example 129
rel-4-(4-Methanesulfonyl-5-oxo-6R-propyl-hexahydro-(3aS,6aR)-pyrrolo[3,2-b]pyrrol-1-yl)-oxo-but-2-E-enoic acid A solution of Example 128 (465 mg) in dioxan (35 ml) and 2M hydrochloric acid (15 ml) was stirred and heated at 60–70° for 17 hours and at 70–80° for a further 1.5 hours The cooled reaction mixture was concentrated to ca 20 ml in vacuo and extracted with ethyl acetate (2×35 ml). The combined organic extracts were washed with water (20 ml), dried ($Na_2SO_4$), filtered and concentrated in vacuo to give the title compound as a pale yellow foam (281 mg). Tlc Silica. Ethyl Acetate Rf=0.45 Mass spec $MH^+$ (found)=345 $MH^+$ (calculated)=345.

Example 130
rel-(3R,3aR,6aS)-1-(4-Methanesulfonyl-5-oxo-6-propyl-hexahydro-pyrrolo[3,2-b]pyrrol-1-yl)-4-(4-methyl-piperazin-1-yl)-but-2E-ene-1,4-dione hydrochloride A solution of 1-methylpiperazine (30 mg) in dry dimethylformamide (0.5 ml) was added to a stirred solution of Example 129 (55 mg), 1-hydroxybenzotriazole (27 mg) and 1-(3-dimethylaminopropyl)-3-ethylcarbodiimide hydrochloride (39 mg) in dry dimethylformamide (1.5 ml). The reaction mixture was stirred at room temperature for 20 hours then treated, with vigorous stirring, with sodium bicarbonate (4%; 25 ml) and extracted with ethyl acetate (3×25 ml). The combined organic extracts were washed with water (2×35 ml), dried ($Na_2SO_4$), filtered and concentrated in vacuo to give a solid. The solid was triturated in diethyl ether (10 ml). The ether was decanted. The residue was dried in vacuo to give the title compound as a cream powder (54 mg). Tlc Silica. (100:8:1) Mixture of dichloromethane, ethanol and ammonia (S.G.=0.88) Rf=0.35 Mass spec $MH^+$ (found)=427 $MH^+$ (calculated)=427.

Example 131
rel-(3R,3aR,6aS)-4-But-2E-enoyl-1-methanesulfonyl-3-propyl-hexahydro-pyrrolo[3,2-b]pyrrol-2-one A solution of 1-hydroxybenzotriazole (54 mg), 1-(3-dimethylaminopropyl)-3-ethylcarbodiimide hydrochloride (77 mg) and crotonic acid (35 mg) in dry tetrahydrofuran (3 ml) and dimethylformamide (0.5 ml) was stirred at room temperature for 10 minutes then treated with Intermediate 26 (50 mg). The reaction mixture was stirred at room temperature for 18 hours then partitioned between 8% sodium bicarbonate solution (8 ml) and ethyl acetate (15 ml). The organic phase was separated, washed with 0.5M hydrochloric acid (10 ml) and water (10 ml), dried $Na_2SO_4$ and filtered to give a semi-solid. The semi-solid was purified by flash column chromatography on silica, eluting with a mixture of cyclohexane and ethyl acetate (initially 1:1, gradually increasing the concentration of ethyl acetate to give a 2:1 mixture), to give the title compound as a cream powder (44 mg). Melting point 165–166° Mass spec $MH^+$ (found)=315 $MH^+$ (calculated)=315.

Examples 132–133
The above Examples were prepared in a similar manner to Example 62, from Intermediate 115.

rel-(3R,3aR,6aS)-1-Methanesulfonyl-4-{3-(4-(4-methyl-piperazin-1-ylmethy)-phenyl-(E)-acryloyl}-3-propyl-hexahydro-pyrrolo[3,2-b]pyrrol-2-one dihydrochloride Melting Point 188–192°. Mass spec. $MH^+$ (found)=489 $MH^+$ (calc.)=489. (Example 132)

rel-(3R,3aR,6aS)-1-Methanesulfonyl-4-[3-(4-piperidin-1-ylmethyl-phenyl)-(E)-acryloyl]-3-propyl-hexahydro-pyrrolo[3,2-b]pyrrol-2-one hydrochloride Melting Point 152–157°. Mass spec. $MH^+$ (found)=474 $MH^+$ (calc.)=474 (Example 133)

Example 134
The above Example was prepared in a similar manner to Example 131 from Intermediate 26.

rel-N-{4-[3-(4-Methanesulfonyl-5-oxo-6R-propyl-hexahydro-(3aS,6aR)-pyrrolo[3,2-b]pyrrol-1-yl)-3-oxo-(E)-propenyl]-phenyl}acetamide Melting point 213–215°. Mass spec. $MH^+$ (found)=434. $MH^+$ (calc.)=434. (Example 134)

Example 135
rel-(3R,3aR,6aS)-3-Isopropyl-1-methanesulfonyl-4-(4-piperidin-1-yl-but-2E-enoyl)-hexahydro-pyrrolo[3,2-b]pyrrol-2-one hydrochloride A solution of Intermediate 86 (246 mg) in dry dimethylformamide (1 ml) was added to a stirred solution of Intermediate 113 (308 mg), 1-hydroxybenzotriazole (202 mg), 1-(3-dimethylaminopropyl)-3-ethylcarbodiimide hydrochloride (286 mg) and triethylamine (303 mg) in dry dimethylformamide (5 ml). The reaction mixture was stirred at room temperature for 16 hours, treated with 8% sodium bicarbonate solution (25 ml) and extracted with ethyl acetate (35 ml+25 ml). The combined organics were washed with water (2×30 ml), dried ($Na_2SO_4$), filtered and evaporated to give a gum. Purification by flash chromatography on silica, using a mixture of dichloromethane, ethanol and ammonia (100:8:1) as the eluent, gave a pale yellow foam (266 mg) as the major product. Salt formation (1.0M hydrogen chloride in diethyl ether, slight molar excess) gave the title compound as a white powder (269 mg). Melting point>220° (decomposes) Tlc Silica. (100:8:1) Mixture of dichloromethane ethanol and ammonia (S.G.=0.88) Rf=0.5 Mass spec $MH^+$ (found)=398 $MH^+$ (calculated)=398.

Example 136
rel-(3R,3aR,6aS)-4-(4-Azepin-1-yl-but-2E-enoyl)-3-isopropyl-1-methanesulfonyl-hexahydro-pyrrolo[3,2-b]pyrrol-2-one hydrochloride A mixture of Intermediate 86 (50 mg), Intermediate 120 (104 mg), EDC hydrochloride (150 mg) triethylamine (250 mg) and anhydrous sodium sulphate (750 mg) in dichloromethane (10 ml) and dimethylformamide (0.5 ml) was stirred at room temperature for 5 days. The reaction mixture was partitioned between dichloromethane (6 ml) and 4% aqueous sodium hydrogen carbonate. The aqueous phase was extracted with dichloromethane (2×3 ml), and the combined organics were dried ($Na_2SO_4$) filtered and evaporated to a viscous oil which was purified by flash chromatography on silica using ethanol:dichloromethane:ammonia (8:100:1) as eluent. The resultant colourless glass was dissolved in dichloromethane (3 ml) and ethereal hydrogen chloride (3 ml, 1.0M) was added. The resultant solid suspension was evaporated to give the title compound as a pale yellow solid (43 mg). Mass spec. $MH^+$ (found) 412 $MH^+$ (calculated) 412 M.p 150–154° (dec)

Example 137 rel-(3R,3aR,6aS)-4-(4-Cyclopropylamino-but-2E-enoyl)-3-isopropyl-1-methanesulfonyl-hexahydro-pyrrolo[3,2-b]pyrrol-2-one hydrochloride A mixture of Intermediate 117 (30 mg), cyclopropylamine (15 mg) and sodium iodide (30 mg) in acetonitrile (3 ml) was stirred at room temperature for 24 hours. The acetonitrile was removed in vacuo and the residue partitioned between ethyl acetate (15 ml) and 8% sodium bicarbonate (10 ml). The organic phase was separated, washed with water (12 ml), dried ($Na_2SO_4$), filtered and evaporated to give a gum. Purification by flash column chromatography on silica, using a mixture of ethyl acetate and methanol (10:1) as the eluent, gave a gum (12 mg) as the major component. A solution of the gum in a (1:1) mixture of ether and ethyl acetate (5 ml) was stirred and treated with a 1.0M. solution of ethereal hydrogen chloride (0.15 ml). The solvents were decanted. The residual solid was washed with ether and dried in vacuo to give the title compound as a pale yellow powder (13 mg). Tlc Silica. (100:8:1) Mixture of dichloromethane ethanol and ammonia (S.G.=0.88) Rf=0.5 Mass spec $MH^+$ (found)=370 $MH^+$ (calculated)=370.

Examples 138–147

The above Examples were prepared in a similar manner to Example 137 from Intermediate 117.

rel-(3R,3aR,6aS)-4-[4-(4-Acetyl-piperazin-1-yl)-but-2E-enoyl]-3-isopropyl-1-methanesulfonyl-hexahydro-pyrrolo[3,2-b]pyrrol-2-one hydrochloride TLC. Silica. (100:8:1) Mixture of dichloromethane, ethanol and ammonia (S.G.=0.88). Rf=0.45. Mass spec. $MH^+$ (found)=441. $MH^+$ (calc.)=441. (Example 138)

rel-(3R,3aR,6aS)-4-[4-(2,6-Dimethyl-piperidin-1-yl)-but-2E-enoyl]-3-isopropyl-1-methanesulfonyl-hexahydro-pyrrolo[3,2-b]pyrrol-2-one hydrochloride TLC. Silica. (100:8:1) Mixture of dichloromethane, ethanol and ammonia (S.G.=0.88). Rf=0.53. Mass spec. $MH^+$ (found)=426. $MH^+$ (calc.)=426. (Example 139)

1-[4-(rel-6R-Isopropyl-4-methanesulfonyl-5-oxo-hexahydro-(3aS,6aR)-pyrrolo[3,2-b]pyrrol-1-yl)-4-oxo-but-2E-enyl]-pyrrolidine-2S-carboxylic acid methyl ester hydrochloride Melting point 118–122° C. TLC. Silica. (100:8:1) Mixture of dichloromethane, ethanol and ammonia (S.G.=0.88). Rf=0.55. Mass spec. $MH^+$ (found)=442. $MH^+$ (calc. )=442. (Example 140)

rel-(3R,3aR,6aS)-3-Isopropyl-1-methanesulfonyl-4-[4-(methyl-propyl-amino)-but-2E-enoyl]-hexahydro-pyrrolo[3,2-b]pyrrol-2-one hydrochloride TLC. Silica. (100:8:1) Mixture of dichloromethane, ethanol and ammonia (S.G.=0.88). Rf=0.55. Mass spec. $MH^+$ (found)=386. $MH^+$ (calc.)=386. (Example 141)

rel-(3R,3aR,6aS)-3-isopropyl-1-methanesulfonyl-4-(4-morpholin-4-yl-but-2E-enoyl)-hexahydro-pyrrolo[3,2-b]pyrrol-2-one hydrochloride Melting point 152–155° C. TLC. Silica. (100:8:1) Mixture of dichloromethane, ethanol and ammonia (S.G.=0.88). Rf=0.65. Mass spec. $MH^+$ (found)=400. $MH^+$ (calc.)=400. (Example 142)

rel-(3R,3aR,6aS)-3-Isopropyl-1-methanesulfonyl-4-[4-(4-methyl-piperazin-1-yl)-but-2E-enoyl]-hexahydro-pyrrolo[3,2-b]pyrrol-2-one hydrochloride Melting point 166–171° C. TLC. Silica. (100:8:1) Mixture of dichloromethane, ethanol and ammonia (S.G.=0.88). Rf=0.15. Mass spec. $MH^+$ (found)=413. $MH^+$ (calc.)=413. (Example 143)

rel-(3R,3aR,6aS)-4-(4-Diisopropylamino-but-2E-enoyl)-3-isopropyl-1-methanesulfonyl-hexahydro-pyrrolo[3,2-b]pyrrol-2-one hydrochloride Melting point 119–123°. TLC. Silica. (100:8:1) Mixture of dichloromethane, ethanol and ammonia (S.G.=0.88). Rf=0.50. Mass spec. $MH^+$ (found)=414. $MH^+$ (calc.)=414. (Example 144)

rel-(3R,3aR,6aS)-4-Diethylamino-but-2E-enoyl)-3-isopropyl-1-methanesulfonyl-hexahydro-pyrrolo[3,2-b]pyrrol-2-one hydrochloride TLC. Silica. (100:8:1) Mixture of dichloromethane, ethanol and ammonia (S.G.=0.88). Rf=0.56. Mass spec. $MH^+$ (found)=386. $MH^+$ (calc.)=386. (Example 145)

rel-(3R,3aR,6aS)-3-Isopropyl-1-methanesulfonyl-4(4-pyrrolidin-1-yl-but-2E-enoyl)-hexahydro-pyrrolo[3,2-b]pyrrol-2-one hydrochloride Melting point 130–135° C. TLC. Silica. (100:8:1) Mixture of dichloromethane, ethanol and ammonia (S.G.=0.88). Rf=0.35. Mass spec. $MH^+$ (found)=384. $MH^+$ (calc.)=384. (Example 146)

rel-(3R,3aR,6aS)-3-Isopropyl-1-methanesulfonyl-4-[4-(methoxy-methyl-amino)-but-E2-enoyl]-hexahydro-pyrrolo[3,2-b]pyrrol-2-one hydrochloride TLC. Silica. (100:8:1) Mixture of dichloromethane, ethanol and ammonia (S.G.=0.88). Rf=0.60. Mass spec. $MH^+$ (found)=374. $MH^+$ (calc. 374. (Example 147)

Example 148 rel-(3R,3aR,6aS)-4-(4-Dimethylamino-but-2E-enoyl)-3-isopropyl-1-methanesulfonyl-hexahydro-pyrrolo[3,2-b]pyrrol-2-one hydrochloride A mixture of Intermediate 118 (30 mg), sodium iodide (30 mg), dimethylammonium chloride (20 mg) and triethylamine (15 mg) in acetonitrile (2 ml) was stirred at room temperature for 18 hours. More dimethylammonium chloride (20 mg) and triethylamine (22 mg) were added and stirring was continued for 24 hours. The reaction mixture was partitioned between ethyl acetate (2×15 ml) and 8% sodium bicarbonate (4 ml). The combined organic extracts were washed with water (10 ml), dried ($Na_2SO_4$), filtered and concentrated to give a gum. The gum was purified by flash column chromatography on silica using a mixture of dichloromethane, ethanol and ammonia (100:8:1) as the eluent, to give a solid (12 mg) as the major component. Salt formation, using a slight molar excess of 1.0M hydrogen chloride in ether, gave the title compound as a white powder (13 mg). Melting point 224–228° C. Mass spec $MH^+$ (found)=358 $MH^+$ (calculated)=358.

Examples 149–153

The above Examples were prepared in a similar manner to Example 148 from Intermediate 118.

rel-(3R,3aR,6aS)-4-[4-(2,5-Dimethyl-pyrrolidin-1-yl)-but-2E-enoyl]-3-isopropyl-1-methanesulfonyl-hexahydro-pyrrolo[3,2-b]pyrrol-2-one hydrochloride Melting point=121–125° C. TLC. Silica. (100:8:1) Mixture of dichloromethane, ethanol and ammonia (S.G.=0.88).

Rf=0.64. Mass spec. MH$^+$ (found)=412. MH$^+$ (calc. )=412.

(Example 149)
rel-2-{[(4-(6R-Isopropyl-4-methanesulfonyl-5-oxo-hexahydro-(3aS,6aR)-pyrro[3,2-b]pyrrol-1-yl)-4-oxo-but-2E-enyl]-methyl-amino}-acetamide hydrochloride Melting point=136–141° C. TLC. Silica. (100:8:1) Mixture of dichloromethane, ethanol and ammonia (S.G.=0.88). Rf=0.50. Mass spec. MH$^+$ (found)=401. MH$^+$ (calc.) 401.

(Example 150)
rel-(3R,3aR,6aS)-3-Isopropyl-4-(4-isopropylamino-but-2E-enoyl)-1-methanesulfonyl-hexahydro-pyrrolo[3,2-b]pyrrol-2-one hydrochloride Melting point=140–145° C. TLC. Silica. (100:8:1) Mixture of dichloromethane, ethanol and ammonia (S.G. 0.88). Rf=0.30. Mass spec. MH$^+$ (found)=372. MH$^+$ (calc.)=372.

(Example 151)
rel-1-[4-(6R-Isopropyl-4-methanesulfonyl-5-oxo-hexahydro-(3aS,6aR)-pyrrolo[3,2-b]pyrrol-1-yl)-4-oxo-but-2E-enyl]-piperidine-4-carboxylic acid amide hydrochloride Melting point=152–156° C. TLC. Silica. (100:8:1) Mixture of dichloromethane, ethanol and ammonia (S.G.=0.88). Rf=0.13. Mass spec. MH$^+$ (found)=441. MH$^+$ (calc.)=441.

(Example 152)
rel-(3R,3aR,6aS)-4-[4-(5,8-Difluoro-1,3,3a,4,9,9a-hexahydro-(3aS,9aS)-benzol[f]isoindol-2-yl)-but-2E-enoyl]-3-isopropyl-1-methanesulfonyl-hexahydro-pyrrolo[3,2-b]pyrrol-2-one hydrochloride Melting point=165–170° C. TLC. Silica. (100:8:1) Mixture of dichloromethane, ethanol and ammonia (S.G.=0.88). Rf=0.56. Mass spec. MH$^+$ (found)=522. MH$^+$ (calc.)=522.

(Example 153)

Example 154

(3S,3aS,6aR)-3-Isopropyl-1-methanesulfonyl-4-(4-piperidin-1-yl-but-2E-enoyl)-hexahydro-pyrrolo[3,2-b]pyrrol-2-one hydrochloride Intermediate 113 (0.187 g), 1-hydroxybenzotriazole (0.14 g), triethylamine (288 µl), dimethylformamide (4 ml) and 1-(3-dimethylaminopropyl)-3-ethylcarbodiimide hydrochloride (0.198 g) were stirred at room temperature before Intermediate 122 (0.17 g) in dimethylformamide (1 ml) was added. After 3 hours, ethyl acetate (15 ml) was added and the mixture washed with 8% sodium hydrogen carbonate solution (20 ml). The aqueous phase had water (10 ml) added to it, and was then extracted with ethyl acetate (2×10 ml). The combined organic extracts were washed with water (10 ml) and saturated brine solution, dried (MgSO$_4$), filtered and the solvent removed in vacuo to leave a red oil. The oil was purified by flash column chromatography on silica eluting with 100:8:1dichloromethane:ethanol:0.880 ammonia. The required fractions were combined and the solvent removed in vacuo to give a pale yellow crystalline solid. The solid (157 mg) was dissolved in dichloromethane (5 ml) and treated with 1M hydrogen chloride in ether (2 ml). The solution was concentrated in vacuo and dried in vacuo to give the title compound as a white solid (0.168 g).

T.l.c. 100:8:1 dichloromethane/ethanol/0.880 ammonia Rf 0.37 M.pt. 208–211° C. Mass spec. MH$^+$ (found)=398 MH$^+$ (calculated)=398.

Circular Dichroism: $\lambda_{max}$243.8 nm ($\Delta$E –0.97 M$^{-1}$cm$^{-1}$) $\lambda_{max}$283.8 nm ($\Delta$E +0.27 M$^{-1}$cm $^{-1}$), (MeOH) [$\alpha$]$_D^{20}$+48.3 (c=5.55 mg/ml, MeOH).

Found C, 50.1; H, 7.7; N, 9.4; S, 7.4 $C_{19}H_{31}N_3O_4S.HCl.H_2O$ requires C, 50.5; H, 7.6; N, 9.3; S, 7.1%.

Chiral HPLC (chiracel AD column, eluent 40% ethanol/n-heptane, flowrate 1.0 ml/min) Retention time=7.8 min, >99% e.e.

Infra Red (KBr reflectance) u$_{max}$ 1744, 1672, 1631, 1452, 1355, 1166, 1144 cm$^{-1}$ H$^1$ nmr (400 MHz, CDCl$_3$) 3H d 1.00 J 7, 3H d 1.25 J 7, 1H br 1.51, 3H br 1.82, 2H br 1.92, 1H m 2.13 quin J 11, 1H dt 2.53 J 6 and 11, 1H m 2.96, 3H br 2.97, 3H s 3,24, 1H t 3.44 J 11, 2H br 3.49, 1H m 3.66, 2H 3.93 m, 2H br t 3.99 J 9, 2H m 6.73.

C$^{13}$ nmr (62.9 MHz, CDCl$_3$) 17.1, 22.1, 23.0, 24.8, 28.6, 30.0, 40.4, 51.4, 54.8, 56.8, 58.6, 62.5, 65.8, 132.3, 133.4, 166.2, 178.2

Example 155

(3R,3aR,6aS)-3-Isopropyl-1-methanesulfonyl-4-(4-piperidin-1-yl-but-2E-enoyl)-hexahydro-pyrrolo[3,2-b]pyrrol-2-one hydrochloride A mixture of Intermediate 113 (25 mg), EDC (23 mg), 1-hydroxybenzotriazole (16 mg) and triethylamine (33 µl) in dimethylformamide (0.5 ml) was stirred under nitrogen for 10 minutes before a solution of Intermediate 124 (20 mg) in dimethylformamide (0.5 ml) was added. The mixture was stirred at room temperature for 2 hours and then poured onto 8% aqueous sodium hydrogen carbonate (3 ml). The mixture was extracted with ethyl acetate (2×20 ml) and the combined extracts washed with water (2×10 ml). The organics were dried (MgSO$_4$) filtered and evaporated to a pasty gum which was purified by flash chromatography on silica using ethanol:dichloromethane:ammonia (8:100:1) as eluent. The resultant white paste was triturated with ethereal hydrogen chloride (3 ml, 1.0M). The resultant precipitate was collected and dried to give the title compound as a finely divided pale yellow solid (17 mg). T.l.c 100:8:1, dichloromethane:ethanol:ammonia:Rf.0.23 Mass spec. MH$^+$ (found) 398 MH$^+$ (calculated) 398.

Example 156 rel-(3aS,6R,6aS)-4-Methanesulfonyl-6-methoxy-5-oxo-hexahydro-pyrrolo[3,2-b]pyrrole-1-carboxylic acid benzyl ester A solution of Intermediate 128 (150 mg) in dry tetrahydrofuran (8 ml) was stirred at –78° and treated, rapidly dropwise, with a solution of lithium hexamethyidisilazide in tetrahydrofuran (1.0 molar, 0.7 ml). The reaction mixture was stirred at –78° for 10 minutes; warmed at 0° C. over 20 minutes; stirred at 0° for 15 minutes then cooled to –78°. Methanesulphonyl chloride (179 mg) was added. The reaction mixture was stirred at –78° for a further 4 hours then treated with saturated ammonium chloride (8 ml) and warmed to room temperature. The solution was extracted with ethyl acetate (2×25 ml). The combined organics were dried (Na$_2$SO$_4$), filtered and concentrated to give a pale yellow semi-solid. Trituration in diethyl ether afforded the title compound as a cream powder (156 mg). Melting point 146–149° Mass spec MH$^+$ (found)=369 MH$^+$ (calculated)= 369.

Example 157 rel-(3aS,6R,6aS)-4-Methanesulfonyl-6-methylsulfonyl-5-oxo-hexahydro-pyrrolo[3,2-b]pyrrole-1-carboxylic acid benzyl ester To a stirring solution of Intermediate 131 (82 mg) in anhydrous tetrahydrofuran (5 ml) at –8° C. under nitrogen was added 0.5M potassium bis(trimethylsilyl)amide in toluene (0.7 ml) over 1 min. The resulting mixture was left stirring at –8° C. for 5 min, then at 0° C. for 1 h before being cooled to –70° C. and treated with methanesulphonyl chloride (30 µl). The resultant was stirred at –70° C. to –80° C. for 3½ h, treated with a saturated solution of aqueous ammonium chloride (1 ml) and allowed to warm to 0° C. over 10 min. It was then diluted with ethyl acetate (30 ml)

and the organic phase was washed with brine (10 ml), dried (Na$_2$SO$_4$) filtered and concentrated in vacuo to a gum. Purification by column chromatography eluting with ethyl acetate resulted in fractions which were concentrated in vacuo to give the title compound (50 mg). Tlc (Dichloromethane:Ethyl Acetate 1:1) Rf 0.68 Mass spec: MH$^+$ (found)=385 MH$^+$ (calculated)=385.

Examples 158–159

The above Examples were prepared in a similar manner to Example 62 from Intermediate 132.
rel-(3R,3aR,6aS)-3-Isopropyl-1-methanesulfonyl-4-[3-(4-piperidin-1-ylmethyl-phenyl)-(E)-acryloyl]-hexahydro-pyrrolo[3,2-b]pyrrol-2-one hydrochloride
Melting point 145–150°. TLC. Silica. (100:8:1) Mixture of dichloromethane, ethanol and ammonia (S.G.=0.88). Rf=0.50. Mass spec. MH$^+$ (found)=474. MH$^+$ (calc.)=474. (Example 158)
rel-(3R,3aR,6aS)-4-[3-(4-Dimethylaminoethyl-phenyl)-(E)-acryloyl]-3-isopropyl-1-methanesulfonyl-hexahydro-pyrrolo[3,2-b]pyrrol-2-one hydrochloride
Melting point 149–152° C. TLC. Silica. (100:8:1) Mixture of dichloromethane, ethanol and ammonia (S.G.=0.88). Rf=0.42. Mass spec. MH$^+$ (found)=434. MH$^+$ (calc.)=434. (Example 159)

Example 160
rel-(3R,3aR,6aS)-1-Ethanesulfonyl-4-(3-piperidin-1-yl-propionyl)-3-propyl-hexahydro-pyrrolo[3,2-b]pyrrol-2-one DL-tartrate To a stirred suspension of potassium hydride 35% dispersion in mineral oil (44 mg) washed with hexane (2 ml), in dry tetrahydrofuran (2 ml) under nitrogen at approximately 2° C. was added a solution of Intermediate 133 (44 mg) in dry tetrahydrofuran (3 ml). After stirring for 1¾ hours, the mixture was cooled to −75° C. and ethanesulphonyl chloride (27 µl) was added. The mixture was stirred for a further 1½ hours at −75° C. before 8% NaHCO$_3$ (1 ml) was added and the mixture allowed to warm to room temperature. The mixture was partitioned between 8% NaHCO$_3$ (10 ml) and ethyl acetate (10 ml). The aqueous phase was further extracted with ethyl acetate (2×10 ml), the combined organic phases washed with brine (10 ml), dried (Na$_2$SO$_4$), filtered and the solvent removed in vacuo to leave a yellow oil. The oil was purified by flash column chromatography eluting with 7:1 dichloromethane/methanol. The required fractions were combined and the solvent removed in vacuo to give a colourless oil, (28 mg). The oil was dissolved in ethanol (2 ml), stirred, and a solution of (D,L)-tartaric acid (10.5 mg) in ethanol (1 ml) was added to it. After stirring for 15 minutes, the solvent was removed in vacuo and the residue evaporated to dryness from ether in vacuo twice, to give the title compound as a white foam (38 mg). Tlc(Silica plate) 7:1 Dichloromethane/Methanol) Rf=0.29 Mass spec MH$^+$ (found)=400 MH$^+$ (calculated)=400.

Examples 161–164

The above Examples were prepared in a similar manner to Example 160 from Intermediate 133.
rel-(3R,3aR,6aS)-4-(3Piperidin-1-yl-propionyl)-1-(propane-2-sulfonyl)-3-propyl-hexahydro-pyrrol[3,2-b]pyrrol-2-one DL-tartrate
Tlc (dichloromethane:methanol; 7:1) Rf 0.3 Mass spec. (found) MH$^+$=414, (calc) MH$^+$=414. (Example 161)
rel-(3R,3aR,6aS)-4-(3-Piperidin-1-yl-propionyl)-1-(propane-1-sulfonyl)-3-propyl-hexahydro-pyrrolo[3,2-b]pyrrol-2-one DL-tartrate Tlc (dichloromethane:methanol; 7:1) Rf 0.25 Mass spec. (found) MH$^+$=414, (calc) MH$^+$=414. (Example 162)
rel-(3R,3aR,6aS)-1-(Butane-1-sulfonyl)-4-(3-piperidin-1-yl-propionyl)-3-propyl-hexahydro-pyrrolo[3,2-b]pyrrol-2-one DL-tartrate
Tlc (dichloromethane:methanol; 7:1) Rf 0.3 Mass spec. (found) MH$^+$=428, (calc) MH$^+$=428. (Example 163)
rel-(3R,3aR,6aS)-4-(3-Piperidin-1-yl-propionyl)-3-propyl-1-(2,2,2-trifluoro-ethanesulfonyl)-hexahydro-pyrrolo[3,2-b] pyrrol-2-one DL-tartrate
Tlc (dichloromethane:methanol; 7:1) Rf 0.36 Mass spec. (found) MH$^+$=454, (calc) MH$^+$=454. (Example 164)

Examples 165–167

The above Examples were prepared in a similar manner to Example 160 from Intermediate 135.
rel-(3R,3aR,6aS)-1-Ethanesulfonyl-4-(3-piperidin-1-yl-propane-1-sulfonyl)-3-propyl-hexahydro-pyrrolo[3,2-b] pyrrol-2-one DL-tartrate
Tlc (dichloromethane:methanol, 7:1) Rf 0.2 Mass spec. (found) MH$^+$=450, (calc) MH$^+$=450. (Example 165)
rel-(3R,3aR,6aS)-4-(3-Piperidin-1-yl-propane-1-sulfonyl)-1-(propane-2-sulfonyl)-3-propyl-hexahydro-pyrrolo[3,2-b] pyrrol-2-one DL-tartrate
Tlc (dichloromethane:methanol; 7:1) Rf 0.38 Mass spec. (found) MH$^+$=464, (calc) MH$^+$=464. (Example 166)
rel-(3R,3aR,6aS)-1-(Butane-1-sulfonyl)-4-(3-piperidin-1-yl-propane-1-sulfonyl)-3-propyl-hexahydro-pyrrolo[3,2-b] pyrrol-2-one DL-tartrate
Tlc (dichloromethane:methanol; 7:1) Rf 0.46 Mass spec. (found) MH$^+$=478, (calc) MH=478. (Example 167)

Example 168
rel-(3R,3aR,6aS)-1-(Benzo[1,2,5]thiadiazole-4-sulfonyl)-4-(3-piperidin-1-yl-propionyl)-3-propyl-hexahydro-pyrrolo[3,2-b]pyrrol-2-one DL-tartrate Potassium hydride-35% dispersion in mineral oil, (43 mg) was washed with hexane (~5 ml) before dry tetrahydrofuran (2 ml) was added and the suspension cooled to 0° C. under nitrogen. Intermediate 133 (33 mg) in dry tetrahydrofuran (2 ml) was added and the resulting mixture stirred at 0° C. for 2 hours. The solution was cooled to −75° C. and 2,1,3-benzothiadiazole-4-sulfonyl chloride (76 mg) in dry tetrahydrofuran (2 ml) was added and the resulting solution stirred at −75° C. for 1.5 hours. 8% aqueous sodium bicarbonate (2 ml) was added and the reaction allowed to warm to room temperature. The mixture was partitioned between ethyl acetate (50 ml) and 8% aqueous sodium bicarbonate (150 ml). The layers were separated and the aqueous phase washed with ethyl acetate (50 ml). The organic phases were combined, dried (MgSO$_4$), filtered and concentrated in vacuo to leave a yellow gum. The gum was purified by flash column chromatography eluting with dichloromethane:methanol (9:1) to give, after evaporation of solvent in vacuo, a colourless oil. The oil (36 mg) was dissolved in ethanol (2 ml) and (D,L)-tartaric acid (10.7 mg) was added. After 15 mins the volatiles were removed in vacuo to give the title compound as a brown solid (50 mg). Tlc (silica plate) Dichloromethane methanol (7.1) Rf. 0.41 Mass spec MH$^+$ (found)=506 MH$^+$ (calculated)=506.

Example 169

The above Example was prepared in a similar manner to Example 168 from Intermediate 134.
rel-(3R,3aR,6aS)-4-(6-Piperidin-1-yl-hexanoyl)-3-propyl-1-(thiophene-2-sulfonyl)-hexahydro-pyrrolo[3,2-b]pyrrol-2-one DL-tartrate Tlc (dichloromethane:methanol; 7:1) Rf 0.21 Mass spec. (found) MH+=496, (calc) MH+=496.

Example 170

The above Example was prepared in a similar manner to Example 168 from Intermediate 133.
rel-(3R,3aR,6aS)-1-(3,5-Dimethyl-isoxazole-4-sulfonyl)-4-(3-piperidin-1-yl-propionyl)-3-propyl-hexahydro-pyrrol[3,2-b]pyrrol-2-one DL-tartrate Tlc (dichloromethane:methanol; 7:1) Rf 0.2 Mass spec. (found) MH+=467, (calc) MH+=467.

Example 171 rel-(3R,3aR,6aS)-4-(3-Piperidin-1-yl-propionyl)-3-propyl-1-(pyridine-2-sulfonyl)-hexahydro-pyrrolo[3,2-b]pyrrol-2-one hydrochloride Potassium hydride-35% dispersion in mineral oil (46 mg) was washed with hexane (~5 ml) before dry tetrahydrofuran (2 ml) was added and the suspension cooled to 0° C. under nitrogen. Intermediate 133 in dry tetrahydrofuran (2 ml) was added and the resulting mixture stirred at 0° C. for 2 h. The solution was cooled to −75° C. and 2-pyridinesulfonyl chloride (62 mg) in dry tetrahydrofuran (0.5 ml) was added and the resulting solution stirred at −75° C. for 2 h. 8% aqueous saturated sodium bicarbonate (2 ml) was added and the reaction allowed to warm to room temperature. The mixture was partitioned between ethyl acetate (50 ml) and 8% sodium bicarbonate (50 ml). The layers were separated and the aqueous phase washed with ethyl acetate (50 ml). The combined organic phases were dried (MgSO4), filtered and concentrated in vacuo to leave a white semi-solid. The semi solid was purified by flash column chromatography eluting with dichloromethane:methanol (7:1), to give, after evaporation of solvent in vacuo a white solid. The solid (30 mg) was dissolved in dry dichloromethane (4 ml) and 1.0M hydrogen chloride in ether (0.5 ml) was added. After 5 mins the volatiles were removed in vacuo to give the title compound as a pale yellow solid (38 mg). Tlc (Silica plate) Dichloromethane:Methanol (7:1) Rf: 0.20 Mass spec MH+ (found)=449 MH+ (calc)=449.

Example 172

The above Example was prepared in a similar manner to Example 171 from Intermediate 133.
rel-(3R,3aR,6aS)-4-(3-Piperidin-1-yl-propionyl)-3-propyl-1-(pyridine-3-sulfonyl)-hexahydro-pyrrolo[3,2-b]pyrrol-2-one dihydrochloride Tlc (dichloromethane:methanol; 7:1) Rf 0.2 Mass spec. (found) MH+=449, (calc) MH+=449.

Example 173 rel-(3R,3aR,6aS)-3-Isopropyl-1-methanesulfonyl-4-(4-pyrrolidin-1-ylmethyl-benzoyl)-hexahydro-pyrrolo[3,2-b]pyrrol-2-one hydrochloride Pyrrolidine (7.31 µl) was added to a stirred solution of Intermediate 136 (30 mg) in dry dichloromethane (3 ml). After a few minutes, sodium triacetoxyborohydride (25.2 mg) was added to the mixture before stirring for 3 days. Saturated sodium bicarbonate solution (1 ml) was added to the mixture, and stirred vigorously for 10 minutes. The organic phase was purified by chromatography, the required fractions combined and the solvent evaporated in vacuo to give a colourless oil (25 mg). The oil was dissolved in dichloromethane (2 ml) and 1.0M hydrogen chloride in diethyl ether (1 ml) was added to it. The solvent was evaporated from the mixture in vacuo to give the title compound as a white solid (27 mg). Tlc (Silica plate) 9:1 Dichloromethane/Methanol Rf 0.18 Mass spec MH+ (found)=434 MH+ (calculated)=434.

Examples 174–175, 177–179, 182–187

The above Examples were prepared in a similar manner to Example 173 from Intermediate 136.
rel-(3R,3aR,6aS)-3-Isopropyl-1-methanesulfonyl-4-(4-piperidin-1-ylmethyl-benzoyl)-hexahydro-pyrrolo[3,2-b]pyrrol-2-one hydrochloride Tlc (dichloromethane:methanol; 9:1) Rf 0.25 Mass spec. (found) MH+=448, (calc) MH+=448. (Example 174)
rel-(3R,3aR,6aS)-4-(4-Dimethylaminomethyl-benzoyl)-3-isopropyl-1-methanesulfonyl-hexahydro-pyrrolo[3,2-b]pyrrol-2-one hydrochloride Tlc (dichloromethane:methanol; 4:1) Rf 0.31 Mass spec. (found) MH+=408, (calc) MH+=408. (Example 175)
rel-(3R,3aR,6aS)-3-Isopropyl-1-methanesulfonyl-4-(4-morpholin-4-ylmethyl-benzoyl)-hexahydro-pyrrolo[3,2-b]pyrrol-2-one hydrochloride Tlc (dichloromethane:methanol; 9:1) Rf 0.27 Mass spec. (found) MH+=450, (calc) MH+=450. (Example 177)
rel-(3R,3aR,6aS)-4-(4-Azepin-1-ylmethyl-benzoyl)-3-isopropyl-1-methanesulfonyl-hexahydro-pyrrolo[3,2-b]pyrrol-2-one hydrochloride Tlc (dichloromethane:methanol; 9:1) Rf 0.25 Mass spec. (found) MH+=462, (calc) MH+=462. (Example 178)
rel-(3R,3aR,6aS)-3-Isopropyl-4-[4-(isopropylamino-methyl)-benzoyl]-1-methanesulfonyl-hexahydro-pyrrolo[3,2-b]pyrrol-2-one hydrochloride Tlc (dichloromethane:methanol; 9:1) Rf 0.25 Mass spec. (found) MH+=422, (calc) MH+=422. (Example 179)
rel-(3R,3aR,6aS)-4-(4-Diethylaminomethyl-benzoyl)-3-isopropyl-1-methanesulfonyl-hexahydro-pyrrolo[3,2-b]pyrrol-2-one hydrochloride Tlc (dichloromethane:methanol; 9:1) Rf 0.2 Mass spec. (found) MH+=436, (calc) MH+=436. (Example 182)
1-[4-(rel-6R-Isopropyl-4-methanesulfonyl-5-oxo-hexahydro-(3aS,6aR)-pyrrolo[3,2-b]pyrrole-1-carbonyl)-benzyl]-pyrrolidine-2S-carboxylic acid methyl ester hydrochloride Tlc (dichloromethane:methanol; 9:1) Rf 0.48 Mass spec. (found) MH+=492, (calc) MH+=492. (Example 183)
rel-(3R,3aR,6aS)-3-Isopropyl-1-methanesulfonyl-4-[4-(octahydro-isoquinolin-2-ylmethyl)-benzoyl]-hexahydro-pyrrolo[3,2-b]pyrrol-2-one hydrochloride Tlc (dichloromethane:methanol; 9:1) Rf 0.36 Mass spec. (found) MH+=502, (calc) MH+=502. (Example 184)
rel-(3R,3aR,6aS)-4-[4-Acetyl-piperazin-1-ylmethyl)-benzoyl]-3-isopropyl-1-methanesulfonyl-hexahydro-pyrrolo[3,2-b]pyrrol-2-one hydrochloride Tlc (dichloromethane:methanol; 9:1) Rf 0.38 Mass spec. (found) MH+=491, (calc) MH+=491. (Example 185)
rel-(3R,3aR,6aS)-4-[4-(2,5-Dimethyl-pyrrolidin-1-ylmethyl)-benzoyl]-3-isopropyl-1-methanesulfonyl-hexahydro-pyrrolo[3,2-b]pyrrol-2-one hydrochloride Tlc (dichloromethane:methanol; 9:1) Rf 0.23 Mass spec. (found) MH+=462, (calc) MH+=462. (Example 186)
rel-1-[4-(6R-Isopropyl-4-methanesulfonyl-5-oxo-hexahydro-(3aS,6aR)-pyrrolo[3,2-b]pyrrole-1-carbonyl)-benzyl]-piperidine-4-carboxylic acid amide hydrochloride Tlc (dichloromethane:methanol; 9:1) Rf 0.04 Mass spec. (found) MH+=491, (calc) MH+491. (Example 187)

Example 176 rel-(3R,3aR,6aS)-3-Isopropyl-1-methanesulfonyl-4-[4-(4-methyl-piperazin-1-ylmethyl)-benzoyl]-hexahydro-pyrrolo[3,2-b]pyrrol-2-one dihydrochloride To a stirred solution of Intermediate 136 (45 mg) in dry dichloromethane (2 ml) under nitrogen was added acetic acid (7 µl), N-methylpiperazine (14.5 µl) and sodium triacetoxyborohydride (38 mg). The mixture was stirred for 20 hours, before saturated NaHCO$_3$ (1 ml) was added and stirred vigorously for 10 mins. The mixture was diluted with NaHCO$_3$ (10 ml) and dichloromethane (10 ml) and the phases separated. The acqueous phase was extracted with CH$_2$Cl$_2$ (2×10 ml) and the combined organic phases dried (Na$_2$SO$_4$), filtered and the solvent removed in vacuo to leave a clear oil. The oil was purified by flash column chromatography using Merck 9385 silica and eluted with 9:1CH$_2$Cl$_2$/MeOH. The required fractions were combined and the solvent removed in vacuo to give a clear oil. The oil was dissolved in dichloromethane (8 ml) and 1.0M HCl in ether (1 ml) was added. The solvent was removed in vacuo to give the title compound as a cream coloured solid (52.5 mg). Mass spec MH$^+$ (found)=463; MH$^+$ (calc)=463 Tlc Silica (9:1; CH$_2$Cl$_2$:MeOH) Rf=0.08.

Example 180 rel-(3R,3aR,6aS)-4(4-Cyclopropylaminomethyl-benzoyl)-3-isopropyl-1-methanesulfonyl-hexahydro-pyrrolo[3,2-b]pyrrol-2-one hydrochloride To a stirred solution of Intermediate 136 (70 mg) in anhydrous dichloromethane (7 ml) at room temperature under nitrogen was added cyclopropylamine (14.1 µl) then sodium triacetoxyborohydride (78.4 mg). The mixture was stirred for 22 h then further cyclopropylamine (7.1 µl) and sodium triacetoxyborohydride (39.2 mg) added. After a further 26 h, the reaction was concentrated in vacuo to a white powder. Flash column chromatography on silica (Merck 9385) eluting with methanol:dichloromethane (2 then 5%) gave a white foam. This was dissolved in anhydrous tetrahydrofuran (5 ml) and treated with 1.0M hydrogen chloride in diethyl ether (1 ml). The solvent was removed in vacuo to give the title compound as a fine white powder (71 mg). Mass spec MH$^+$ (found)=420 MH$^+$ (calculated)=420 High Resolution mass spec MH$^+$ (measured)=420.195505 MH$^+$ (C$_{21}$H$_{30}$N$_3$O$_4$S)=420.195704 Error=0.5 ppm.

Example 181 rel-(3R,3aR,6aS)-3-Isopropyl-1-methanesulfonyl-4-{4-[(methyl-propyl-amino)-methyl]-benzoyl}-hexahydro-pyrrolo[3,2-b]pyrrol-2-one hydrochloride A solution of Intermediate 136 (30 mg) in dry dichloromethane (3 ml) was stirred with N-methylpropylamine (9.8 µl). Sodium triacetoxyborohydride (25.2 mg) was added and the reaction was stirred for 48 hours. NaHCO$_3$ solution (1 ml) and water (2 ml) was added to the reaction before stirring vigorously for 10 mins. The product was isolated from the organic phase by pipetting it equally onto two varian silica cartridges (500 mgSi) which had CH$_2$Cl$_2$ filtered through them until the solvent reached the top of the silica. Each pair of columns were then filtered under vacuum to remove the load volume of solvent, before eluting the following solvent quantities into collection tubes by vacuum filtration; dichloromethane (2×col.vol), Chloroform (2×col.vol), Ether (2×col.vol), Ethyl Acetate (2×col.vol), Acetonitrile (2×col.vol), Methanol (4×col vol) (each col.vol. being ~2.5 ml). The product containing fractions were combined and the solvent removed in vacuo to give the free base. The free base was dissolved in CH$_2$Cl$_2$ (2 ml) and treated with 1.0M HCl in ether (1 ml). The solvent was removed in vacuo to give a solid which was triturated in ether, filtered and dried; giving Example 181 as a white solid (26.7 mg). Tlc Silica (9:1; CH$_2$Cl$_2$:MeOH), Rf=0.23 Mass spec MH$^+$ (found)=436; MH$^+$ (calc)=436.

Example 168

The above Example was prepared in a similar manner to Intermediate 12 from Intermediate 138.

rel-(3R,3aR,6aS)-3-Isopropyl-1-methanesulfonyl-4-(4-piperazin-1-ylmethyl-benzoyl)-hexahydro-pyrrolo[3,2-b]pyrrol-2-one dihydrochloride Tlc (dichloromethane:methanol; 9:1) Rf 0.05 Mass spec. (found) MH$^+$=449, (calc) MH$^+$=449.

Examples 189–193

The above Examples were prepared in a similar manner to Example 173 from Intermediate 137.

rel-(3R,3aR,6aS)-3-Isopropyl-1-methanesulfonyl-4-[3-(4-methyl-piperazin-1-ylmethyl)-benzoyl]-hexahydro-pyrrolo[3,2-b]pyrrol-2-one dihydrochloride Tlc (dichloromethane:methanol; 9:1) Rf 0.17 Mass spec. (found) MH$^+$=463, (calc) MH$^+$=463. (Example 189)

rel-(3R,3aR,6aS)-4-(3-Cyclopropylaminomethyl-benzoyl)-3-isopropyl-1-methanesulfonyl-hexahydro-pyrrolo[3,2-b]pyrrol-2-one hydrochloride Tlc (dichloromethane:methanol; 9:1) Rf 0.27 Mass spec. (found) MH$^+$=420, (calc) MH$^+$=420. (Example 190)

rel-1-[3-(6R-Isopropyl-4-methanesulfonyl-5-oxo-hexahydro-(3aS,6aR)-pyrrolo[3,2-b]pyrrole-1-carbonyl)-benzyl]-piperidine-4-carboxylic acid amide hydrochloride Tlc (dichloromethane:methanol; 9:1) Rf 0.12 Mass spec. (found) MH$^+$=491, (calc) MH$^+$=491. (Example 191)

rel-(3R,3aR,6aS)-3-Isopropyl-1-methanesulfonyl-4-(3-piperidin-1-ylmethyl-benzoyl)-hexahydro-pyrrolo]3,2-b]pyrrol-2-one hydrochloride Tlc (dichloromethane:methanol; 9:1) Rf 0.24 Mass spec. (found) MH$^+$=448, (calc) MH$^+$=448. (Example 192)

rel-(3R,3aR,6aS)-3-Isopropyl-1-methanesulfonyl-4-(3-pyrroidin-1-ylmethyl-benzoyl)-hexahydro-pyrrolo[3,2-b]pyrrol-2-one hydrochloride Tlc (dichloromethane:methanol; 9:1) Rf 0.2 Mass spec. (found) M$^+$=434, (calc) MH$^+$=434. (Example 193)

Example 194 rel-(3R,3aR,6aS)-1-Methanesulfonyl-4-(4-piperidin-1-ylmethyl-benzenesulfonyl)-3-propyl-hexahydro-pyrrolo[3,2-b]pyrrol-2-one hydrochloride Intermediate 139 (86 mg) was dissolved in DMF (4 ml) and treated with potassium carbonate (50 mg). Piperidine (27 µl) was added and the reaction allowed to stir for 4 h. The mixture was poured into water and extracted with ethyl acetate. The combined organic extracts were washed with water, brine, dried (MgSO$_4$) and concentrated to give a white solid (82 mg). The solid was dissolved in dichloromethane (5 ml) and treated with ethereal HCl (1M, 1 ml). The volatiles were removed in vacuo to give the title compound (86 mg) as a white solid.

Tlc (dichloromethane:methanol; 9:1) Rf 0.5

Mass spec MH$^+$ (found)=484 MH$^+$ (calc)=484

Examples 195–196

The above Examples were prepared in a similar manner to Example 194 from Intermediate 139.

rel-(3R,3aR,6aS)-4-(4-Azepin-1-ylmethyl-benzenesulfonyl)-1-methanesulfonyl-3-propyl-hexahydro-pyrrolo[3,2-b]pyrrol-2-one hydrochloride Tlc (dichloromethane:methanol; 9:1) Rf 0.4 Mass spec. (found) MH$^+$=498, (calc) MH$^+$=498. (Example 195)

rel-(3R,3aR,6aS)-4-(4-Dimethylaminomethyl-benzenesulfonyl)-1-methanesulfonyl-3-propyl-hexahydro-pyrrolo[3,2-b]pyrrol-2-one hydrochloride Tlc (dichloromethane:methanol; 9:1) Rf 0.436 Mass spec. (found) MH⁺=444, (calc) MH⁺=444. (Example 196)

Examples 197–199

The above Examples were prepared in a similar manner to Example 194 from Intermediate 140.

rel-(3R,3aR,6aS)-4-(4-Dimethylaminomethyl-benzenesulfonyl)-3-isopropyl-1-methanesulfonyl-hexahydro-pyrrolo[3,2-b]pyrrol-2-one hydrochloride Tlc (dichlcromethane:methanol; 9:1) Rf 0.36 Mass spec. (found) MH⁺=444, (calc) MH⁺=444. (Example 197)

rel-(3R,3aR,6aS)-3-Isopropyl-1-methanesulfonyl-(4-piperidin-1-ylmethyl-benzenesulfonyl)-hexahydro-pyrrolo[3,2-b]pyrrol-2-one hydrochloride Tlc (dichloromethane:methanol; 9:1) Rf 0.33 Mass spec. (found) MH⁺=484, (calc) MH⁺=484. (Example 198)

rel-(3R,3aR,6aS)-4-(4-Azepin-1-ylmethyl-benzenesulfonyl)-3-isopropyl-1-methanesulfonyl-hexahydro-pyrrolo[3,2-b]pyrrol-2-one hydrochloride Tlc (dichloromethane:methanol; 9:1) Rf 0.41 Mass spec. (found) MH⁺=498, (calc) MH⁺=498. (Example 199)

Examples 200–201

The above Examples were prepared in a similar manner to Example 194 from Intermediate 141 rel-(3R,3aR,6aS)-4-[4-(2,6-Dimethyl-piperidin-1-ylmethyl)-benzoyl]-3-isopropyl-1-methanesulfonyl-hexahydropyrrolo[3,2-b]pyrrol-2-one hydrochloride Tlc (dichloromethane:methanol; 9:1) Rf 0.38 Mass spec. (found) MH⁺=476 (calc) MH⁺=476. (Example 200)

rel-(3R,3aR,6aS)-4-{4-(Diisopropylamino)-methy]benzoyl}3-isopropyl-1-methanesulfonyl-hexahydro-pyrrolo[3,2-b]pyrrol-2-one hydrochloride Tlc (dichloromethane:methanol; 9:1) Rf 0.4. Mass spec. (found) MH⁺=464, (calc) MH⁺=464. (Example 201)

Examples 202–207

The above Examples were prepared in a similar manner to Example 168 from Intermediate 134 rel-(3R,3aR,6aS)-4-(6-Piperidin-1-yl-hexanoyl)-3-propyl-1-(4-trifluoromethyl-benzenesulfonyl)-hexahydro-pyrrolo[3,2-b]pyrrol-2-one DL-tartrate T.l.c. (7:1 Dichloromethane:Methanol) Rf 0.40 Mass spec. (found) MH⁺=558, (calc.) MH⁺=558. (Example 202)

rel-(3R,3aR,6aS)-1-(4-Nitro-benzenesulfonyl)-4-(6-piperidin-1-yl-hexanoyl)-3-propyl-hexahydro-pyrrolo[3,2-b]pyrrol-2-one DL-tartrate T.l.c. (7:1 Dichloromethane:Methanol) Rf 0.48 Mass spec. (found) MH⁺=535, (calc.) MH⁺=535. (Example 203)

rel-(3R,3aR,6aS)-1-(4-Butoxy-benzenesulfonyl)-4-(6-piperidin-1-yl-hexanoyl)-3-propyl-hexahydro-pyrrolo[3,2-b]pyrrol-2-one DL-tartrate T.l.c. (7:1 Dichloromethane:Methanol) Rf 0.43 Mass spec. (found) MH⁺=562, (calc.) MH⁺=562. (Example 204)

rel-4-[2-Oxo-4-(6-piperidin-1-yl-hexanoyl)-3R-propyl-hexahydro-(3aR,6aS)-pyrrolo[3,2-b]pyrrole-1-sulfonyl]-benzonitrile DL-tartrate T.l.c. (7:1 Dichloromethane:Methanol) Rf 0.52 Mass spec. (found) MH⁺=515, (calc.) MH⁺=515. (Example 205)

rel-(3R,3aR,6aS)-1-Benzenesulfonyl-4-(6-piperidin-1-yl-hexanoyl)-3-propyl-hexahydro-pyrrol[3,2-b]pyrrol-2-one DL-tartrate T.l.c. (7:1 Dichloromethane:Methanol) Rf 0.49 Mass spec. (found) MH⁺=490, (calc.) MH⁺=490. (Example 206)

rel-(3R,3aR,6aS)-1-(4-Chloro-benzenesulfonyl)-4-(6-piperidin-1-yl-hexanoyl)-3-propyl-hexahydro-pyrrolo[3,2-b]pyrrol-2-one DL-tartrate T.l.c. (7:1 Dichloromethane:Ethanol) Rf 0.37 Mass spec. (found) MH⁺=524, (calc.) MH⁺524. (Example 207)

Example 208

The above Example was prepared in a similar manner to Example 168 from Intermediate 135.

rel-(3R,3aR,6aS)-1-Benzenesulfonyl-4-(3-piperidin-1-yl-propane-1-sulfonyl)-3-propyl-hexahydro-pyrrolo[3,2-b]pyrrol-2-one DL-tartrate T.l.c. (7:1 Dichloromethane:Methanol) Rf 0.38 Mass spec. (found) MH⁺=498, (calc.) MH⁺=498

Example 209 rel-(3R,3aR,6aS)-1-(4-Amino-benzenesulfonyl)-4-(6-piperidin-1-yl-hexanoyl)-3-propyl-hexahydro-pyrrolo[3,2-b]pyrrol-2-one DL-tartrate Example 203 (0.033 g), ethanol (3 ml) and 10% palladium on charcoal (0.020 g) were stirred under hydrogen for 24 h. The catalyst was then filtered through hyflo and the filtrate concentrated in vacuo. Flash chromatography on silica eluting with dichloromethane:methanol (7:1) gave a white solid (0.08 g). This was dissolved in ethanol (2 ml) and D,L-tartaric acid (0.0189 g) added. Solvent removal afforded the title compound as a white solid (0.088 g). Tlc (7:1 dichloromethane:methanol) Rf 0.30 Mass spec MH⁺ (found)=505 MH⁺ (calc)=505.

Example 210

The above Example was prepared in a similar manner to Example 63, from Intermediate 86.

rel-N-[4-(6R-Isopropyl-4-methanesufonyl-5-oxo-hexahydro-(3aS,6aR)-pyrrolo[3,2-b]pyrrole-1-sulfonyl)-phenyl]-acetamide T.l.c. (9:1 Chloroform:Methanol) Rf 0.59 Mass spec. (found) MNH₄⁺=461, (calc.) MNH₄⁺=461.

Examples 211–220

The above Examples were prepared in a similar manner to Example 63, from Intermediate 26.

rel-(3R,3aR,6aS)-1-Methanesulfonyl-4-(4-nitro-benzenesulfonyl)-3-propyl-hexahydro-pyrrolo[3,2-b]pyrrol-2-one T.l.c. (9:1 Chloroform:Methanol) Rf 0.89 Mass spec. (found) MNH₄⁺=449, (calc.) MNH₄⁺=449. (Example 211)

rel-(3R,3aR,6aS)-1-Methanesulfonyl-4-[4-(2-oxo-pyrrolidin-1yl)-benzenesufonyl]-3-propyl-hexahydro-pyrrolo[3,2-b]pyrrol-2-one T.l.c. (9:1 Chloroform:Methanol) Rf 0.57 Mass spec. (found) MNH₄⁺=487, (calc.) MNH₄⁺=487. (Example 212)

rel-N-[2-Chloro-4-(4-methanesulfonyl-5-oxo-6R-propyl-hexahydro-(3aS,6aR)-pyrrolo[3,2-b]pyrrole-1-sulfonyl)-phenyl]-acetamide T.l.c. (9:1 Chloroform:Methanol) Rf 0.57 Mass spec. (found) MNH₄⁺=495/497, (calc.) MNH₄⁺=495/497. (Example 213)

rel-(3R,3aR,6aS)-4-(4-Butoxy-benzenesulfonyl)-1-methanesulfonyl-3-propyl-hexahydro-pyrrolo[3,2-b]pyrrol-2-one T.l.c. (98:2 Chloroform:Methanol) Rf 0.62 Mass spec. (found) MNH₄⁺=476, (calc.) MNH₄⁺=476. (Example 214)

rel-(3R,3aR,6aS)-4-(4-Chloro-benzenesulfonyl)-1-methanesulfonyl-3-propyl-hexahydro-pyrrolo[3,2-b]pyrrol-2-one T.l.c. (9:1 Chloroform:Methanol) Rf 0.82 Mass spec. (found) MNH₄⁺=438/440, (calc.) MH₄⁺=438/440. (Example 215)

rel-(3R,3aR,6aS)-1-Methanesulfonyl-3-propyl-4-(4-trifluoromethyl-benzenesulfonyl)-hexahydro-pyrrolo[3,2-b]pyrrol-2-one T.l.c. (9:1 Chloroform:Methanol) Rf 0.82 Mass spec. (found) $MNH_4^+$=472, (calc.) $MNH_4^+$=472. (Example 216)
rel-(3R,3aR,6aS)-1-Methanesulfonyl-4-(4-methanesulfonyl-benzenesulfonyl)-3-propyl-hexahydro-pyrrolo[3,2-b]pyrrol-2-one T.l.c. (98:2 Chloroform:Methanol) Rf 0.52 Mass spec. (found) $MNH_4^+$=482, (calc.) $MNH_4^+$=482. (Example 217)
rel-4-(4-Methanesulfonyl-5-oxo-6R-propyl-hexahydro-(3aS,6aR)-pyrrolo[3,2-b]pyrrole-1-sulfonyl)-benzonitrile T.l.c. (98:2 Chloroform:Methanol) Rf 0.62 Mass spec. (found) $MNH_4^+$=429, (calc.) $MNH_4^+$=429. (Example 218)
rel-(3R,3aR,6aS)-4-Benzenesulfonyl-1-methanesulfonyl-3-propyl-hexahydro-pyrrolo[3,2-]pyrrol-2-one T.l.c. (90:10 Chloroform:Methanol) Rf 0.84 Mass spec. (found) $MH^+$=387, (calc.) $MH^+$=387. (Example 219)
rel-(3R,3aR,6aS)-1-Methanesulfonyl-4-(4-methoxy-benzenesulfonyl)-3-propyl hexahydro-pyrrolo[3,2-b]pyrrol-2-one T.l.c. (90:10 Chloroform:Methanol) Rf 0.87 Mass spec. (found) $MH^+$=417, (calc.) $MH^+$=417. (Example 220)

Examples 221–226

The above Examples were prepared in a similar manner to Example 122, from Intermediate 26.
rel-(3R, 3aR,6aS)-4-[4-Dimethylamino-benzenesufonyl)-1-methanesulfonyl-3-propyl-hexahydro-pyrrolo[3,2-b]pyrrol-2-one T.l.c. (90:10 Chloroform:Methanol) Rf 0.91 Mass spec. (found) $MH^+$=430, (calc.) $MH^+$=430. (Example 221)
rel-(3R,3aR,6aS)-1-Methanesulfonyl-4-(3-nitro-benzenesulfonyl)-3-propyl-hexahydro-pyrrolo[3,2-b]pyrrol-2-one T.l.c. (98:2 Chloroform:Methanol) Rf 0.35 Mass spec. (found) $MNH_4^+$=449, (calc.) $MNH_4^+$=449. (Example 222)
rel-(3R,3aR,6aS)-1-Methanesulfonyl-3-propyl-4-(3-trifluoromethyl-benzenesulfonyl)-hexahydro-pyrrolo[3,2-b]pyrrol-2-one T.l.c. (98:2 Chloroform:Methanol) Rf 0.60 Mass spec. (found) $MNH_4^+$=472, (calc.) $MNH_4^+$=472. (Example 223)
rel-(3R,3aR,6aS)-4-(3,5-Bis-trifluoromethyl-benzenesulfonyl)-1-methanesulfonyl-3-propyl-hexahydro-pyrrolo[3,2-b]pyrrol-2-one T.l.c. (98:2 Chloroform:Methanol) Rf 0.64 Mass spec. (found) $MNH_4^+$=540, (calc.) $MNH_4^+$=540. (Example 224)
rel-(3R,3aR,6aS)-1-Methanesulfonyl-3-propyl-4-(2-trifluoromethyl-benzenesulfonyl)-hexahydro-pyrrolo[3,2-b]pyrrol-2-one T.l.c. (98:2 Chloroform:Methanol) Rf 0.60 Mass spec. (found) $MNH_4^+$=472, (calc.) $MNH_4^+$=472. (Example 225)
rel-(3R,3aR,6aS)-1-Methanesulfonyl-4-(2-nitro-benzenesulfonyl)-3-propyl-hexahydro-pyrrolo[3,2-b]pyrrol-2-one T.l.c. (98:2 Chloroform:Methanol) Rf 0.47 Mass spec. (found) $MNH_4^+$=449, (calc.) $MNH_4^+$=449. (Example 226)

Examples 227–230

The above Examples were prepared in a similar manner to Example 122, from Intermediate 86.
rel-(3R,3aR,6aS)-3-Isopropyl-1-methanesulfonyl-4-(4-methanesulfonyl-benzenesulfonyl)-hexahydro-pyrrolo[3,2-b]pyrrol-2-one T.l.c. (98:2 Dichloromethane:Methanol) Rf 0.50 Mass spec. (found) $MNH_4^+$=482, (calc.) $MNH_4^+$=482. (Example 227)

rel-(3R,3aR,6aS)-3-Isopropyl-1-methanesulfony]4-(4-trifluoromethyl-benzenesulfonyl)-hexahydro-pyrrolo[3,2-b]pyrrol-2-one T.l.c. (98:2 Dichloromethane:Methanol) Rf 0.70 Mass spec. (found) $MNH_4^+$=472, (calc.) $MNH_4^+$=472. (Example 228)
rel-(3R,3aR,6aS)-3-Isopropyl-1-methanesulfonyl-4-(4-nitro-benzenesulfonyl)-hexahydro-pyrrolo[3,2-b]pyrrol-2-one T.l.c. (98:2 Chloroform:Methanol) Rf 0.55 Mass spec. (found) $MNH_4^+$=449, (calc.) $MNH_4^+$=449. (Example 229)
rel-(3R,3aR,6aS)-4-(4-Butoxy-benzenesulfonyl)-3-isopropyl-1-methanesulfonyl-hexahydro-pyrrolo[3,2-b]pyrrol-2-one T.l.c. (98:2 Dichloromethane:Methanol) Rf 0.61 Mass spec. (found) $MH^+$=459 (calc.) $MH^+$=459. (Example 230)

Example 231 rel-(3R,3aR,6aS)-4-(Furan-2-carbonyl)-1-methanesulfonyl-3-propyl-hexahydro-pyrrolo[3,2-b]pyrrol-2-one To a stirring solution of Intermediate 26 (75 mg) in anhydrous dichloromethane (3 ml) was added triethylamine (185 µl) and 2-furoyl chloride (34 µl). The resulting solution was left stirring at room temperature under nitrogen for 18 hours. The reaction mixture was then diluted with dichloromethane (75 ml), washed with brine (25 ml), dried ($Na_2SO_4$), filtered and concentrated in vacuo to give a cream foam. Purification by flash chromatography eluting with dichloromethane followed by chloroform:methanol (99:1 then 70:30) resulted in fractions which were concentrated in vacuo to give the title compound as a white solid (83 mg).

Tlc (98:2 chloroform:methanol) Rf 0.29 Mass spec $MH^+$ (found)=341 $MH^+$ (calc)=341.

Examples 232–233

The above Examples were prepared in a similar manner to Example 228 from Intermediate 26.
rel-(3R,3aR,6aS)-1-Methanesulfonyl-3-propyl-4-(thiophene-2-carbonyl)-hexahydro-pyrrolo[3,2-b]pyrrol-2-one T.l.c. (98:2 Chloroform:Methanol) Rf 0.35 Mass spec. (found) $MH^+$=357, (calc.) $MH^+$=357. (Example 232)
rel-(3R,3aR,6aS)-4-Benzoyl-1-methanesulfonyl-3-propyl-hexahydro-pyrrolo[3,2-b]pyrrol-2-one T.l.c. (9:1 Chloroform:Methanol) Rf 0.77 Mass spec. (found) $MH^+$=351, (calc.) $MH^+$=351. (Example 233)

Example 234 rel-(3R,3aR,6aS)-4-(4-Amino-benzenesulfonyl)-1-methanesulfonyl-3-propyl-hexahydro-pyrrolo[3,2-b]pyrrol-2-one To a solution of Example 211 (70 mg) in ethanol (12 ml) was added 10% palladium on charcoal (45 mg) in ethanol (2 ml). The resulting suspension was left stirring at room temperature under hydrogen for 19 h. The reaction mixture was then filtered through celite J2 in vacuo and concentrated in vacuo to a cream foam. Purification by flash chromatography eluting with dichloromethane:acetonitrile (92:8,85:15 then 75:25) resulted in fractions which were concentrated in vacuo to give the title compound as a white solid (33 mg). Tlc (dichloromethane:acetonitrile 7:3) Rf 0.84 Mass spec $MH^+$ (found)=402 $MH^+$ (calc)=402.

Example 235

The above Example was prepared in a similar manner to Example 234, from Example 222.
rel-(3R,3aR,6aS)-4-(3-Amino-benzenesulfonyl)-1-methanesulfonyl-3-propyl-hexahydro-pyrrolo[3,2-b]pyrrol-2-one hydrochloride T.l.c. (free base)(9:1 Dichloromethane:Acetonitrile) Rf 0.46 Mass spec. (found) $MNH_4^+$=419, (calc.) $MNH_4^+$=419.

Example 236

The above Example was prepared in a similar manner to Example 234, from Example 226.
rel-(3R,3aR,6aS)-4-(2-Amino-benzenesulfonyl)-1-methanesulfonyl-3-propyl-hexahydro-pyrrolo[3,2-b]pyrrol-2-one T.l.c. (9:1 Dichloromethane:Acetonitrile) Rf 0.62 Mass spec. (found) $MH^+$=402, (calc.) $MH^+$=402.

Example 237

The above Example was prepared in a similar manner to Example 234, from Example 229.
rel-(3R,3aR,6aS)-4-(4-Amino-benzenesulfonyl)-3-isopropyl-1-methanesulfonyl-hexahydro-pyrrolo[3,2-b]pyrrol-2-one T.l.c. (9:1 Dichloromethane:Acetonitrile) Rf 0.46 Mass spec. (found) $MH^+$=402, (calc.) $MH^+$=402.

Example 238
rel-(3R,3aR,6aS)-1-Methanesulfonyl-3-propyl-4-(pyridine-2-carbonyl)-hexahydro-pyrrolo[3,2-b]pyrrol-2-one To a stirring solution of Intermediate 26 (50 mg) in acetonitrile (10 ml) was added picolinic acid (28 mg), 1-(3-dimethylaminopropyl)-3-ethylcarbodiimide hydrochloride (78 mg) and 1-hydroxybenzotriazole (55 mg). The resulting solution was left stirring at room temperature for 19 h. The reaction mixture was then concentrated in vacuo to a gum, dissolved in dichloromethane (100 ml) and washed with a saturated solution of aqueous sodium bicarbonate (35 ml). The organic phase was washed with brine (35 ml), dried ($Na_2SO_4$), filtered and concentrated in vacuo to give a red brown gum. Purification by flash chromatography eluting with dichloromethane:acetonitrile (9:1 then 8:2) resulted in fractions which were concentrated in vacuo to give the title compound as a white solid (47 mg). Tlc (dichloromethane:acetonitrile 7:3) Rf =0.50 Mass spec $MH^+$ (found)=352 $MH^+$ (calc)=352.

Examples 239–242, 244–247

The above Examples were prepared in a similar manner to Example 238, from Intermediate 26.
rel-(3R,3aR,6aS)-4-(4-Butoxy-benzoyl)-1-methanesulfonyl-3-propyl-hexahydro-pyrrolo[3,2-b]pyrrol-2-one T.l.c. (9:1 Dichloromethane:Acetonitrile) Rf 0.48 Mass spec. (found) $MH^+$=423, (calc.) $MH^+$=423. (Example 239)
rel-(3R,3aR,6aS)-1-Methanesulfonyl-4-(1-methyl-1H-pyrrole-2-carbonyl)-3-propyl-hexahydro-pyrrolo[3,2-b]pyrrol-2-one Mass spec. (found) $MH^+$=354, (calc.) $MH^+$=354 I.R. $v_{max}$ 1748,1612,1357,1145 $cm^{-1}$. (Example 240)
rel-N-[5-(4-Methanesulfonyl-5-oxo-6R-propyl-hexahydro (3aS,6aR)-pyrrolo[3,2-b]pyrrole-1-carbonyl)-pyridin-2-yl]-acetamide T.l.c. (7:3 Dichloromethane:Acetonitrile) Rf 0.38 Mass spec. (found) $MH^+$=409, (calc.) $MH^+$=409. (Example 241)
rel-(3R,3aR,6aS)-1-Methanesulfonyl-3-propyl-4-(1H-pyrrole-2-carbonyl)-hexahydro-pyrrolo[3,2-b]pyrrol-2-one T.l.c. (5:1 Dichloromethane:Diethyl Ether) Rf 0.60 Mass spec. (found) $MH^+$=340, (calc.) $MH^+$=340. (Example 242)
rel-(3R,3aR,6aS)-1-Methanesulfonyl-3-propyl-(4-trifluoromethyl-benzoyl)-hexahydro-pyrrolo[3,2-b]pyrrol-2-one T.l.c. (9:1 Dichloromethane:Acetonitrile) Rf 0.48 Mass spec. (found) $MH^+$=419, (calc.) $MH^+$=419. (Example 244)
rel-(3R,3aR,6aS)-1-Methanesulfonyl-4-(4-methanesulfonyl-benzoyl)-3-propyl-hexahydro-pyrrolo[3,2-b]pyrrol-2-one T.l.c. (7:3 Dichloromethane:Acetonitrile) Rf 0.59 Mass spec. (found) $MH^+$=429, (calc.) $MH^+$=429. (Example 245)
rel-(3R,3aR,6aS)-1-Methanesulfonyl-3-propyl-4-(pyridine-4-carbonyl)-hexahydro-pyrrolo[3,2-b]pyrrol-2-one T.l.c. (6:4 Dichloromethane:Acetonitrile) Rf 0.50 Mass spec. (found) $MH^+$=352, (calc.) $MH^+$=352. (Example 246)
rel-(3R,3aR,6aS)-1-Methanesulfonyl-3-propyl-4-(pyridine-3-carbonyl)-hexahydro-pyrrolo[3,2-b]pyrrol-2-one Mass spec. (found) $MH^+$=352, (calc.) $MH^+$=352 I.R. $v_{max}$ 1746, 1647, 1356, 1146 $cm^{-1}$. (Example 247)

Examples 248–249

The above Examples were prepared in a similar manner to Example 238 from Intermediate 86.
rel-(3R,3aR,6aS)-4-(Furan-2-carbonyl)-3-isopropyl-1-methanesulfonyl-hexahydro-pyrrolo[3,2-b]pyrrol-2-one T.l.c. (1:1 Ethyl acetate:Cyclohexane) Rf 0.24 Mass spec. (found) $MH^+$=341, (calc) $MH^+$=341. (Example 248)
rel-(3R,3aR,6aS)-3-Isopropyl-1-methanesulfonyl-4-(thiophene-2-carbonyl)-hexahydro-pyrrolo[3,2-b]pyrrol-2-one T.l.c. (1:1Ethyl acetate:Cyclohexane) Rf 0.32 Mass spec. (found) $MH^+$=357, (calc) $MH^+$=357. (Example 249)

Examples 250–252

The above Examples were prepared in a similar manner to Example 173 from Intermediate 142.
rel-(3R,3aR,6aS)-3-Isopropyl-1-methanesulfonyl-4-(5-piperidin-1-ylmethyl-furan-2-carbonyl)-hexahydro-pyrrolo[3,2-b]pyrrol-2-one hydrochloride T.l.c. (9:1 Dichloromethane:Methanol) Rf 0.40 Mass spec (found) $MH^+$=438, (calc) $MH^+$=438. (Example 250)
rel-(3R,3aR,6aS)-4-(5-Dimethylaminomethyl-furan-2-carbonyl)-3-isopropyl-1-methanesulfonyl-hexahydro-pyrrolo[3,2-b]pyrrol-2-one hydrochloride T.l.c. (9:1 Dichloromethane:Methanol) Rf 0.42 Mass spec (found) $MH^+$=398, (calc) $MH^+$=398. (Example 251)
rel-(3R,3aR,6aS)-4-(5-Cyclolpropylaminomethyl-furan-2-carbonyl)-3-isopropyl-1-methanesulfonyl-hexahydro-pyrrolo[3,2-b]pyrrol-2-one hydrochloride T.l.c. (9:1 Dichloromethane:Methanol) Rf 0.56 Mass spec (found) $MH^+$=410, (calc) $MH^+$=410. (Example 252)

Example 253

The above Example was prepared in a similar manner to Example 173 from Intermediate 137.
rel-(3R3aR,6aS)-4-(3-Dimethylaminomethyl-benzoyl)-3-isopropyl-1-methanesulfonyl-hexahydro-pyrrolo[3,2-b]pyrrol-2-one hydrochloride Tlc (dichloromethane:methanol; 9:1) Rf 0.19 Mass spec. (found) $MH^+$=408, (calc) $MH^+$=408.

Example 254

The above Example was prepared in a similar manner to Example 137 from Intermediate 114.
rel-(3R,3aR,6aS)-1-Methanesulfonyl-4-[4-(4-methyl-piperazin-1-yl)-but-2E-enoyl]-3-propyl-hexahydro-pyrrolo[3,2-b]pyrrol-2-one dihydrochloride Tlc (dichloromethane:ethanol: 0.88 ammonia; 100:8:1) Rf 0.15 Mass spec. (found) $MH^+$=413, (calc) $MH^+$=413. (Example 254)

Example 255 rel-(3R,3aR,6aS)-3-Isopropyl-1-methanesulfonyl-4-(4-piperidin-4-yl-butyryl)-hexahydro-pyrrolo[3,2-b]pyrrol-2-one hydrochloride A solution of Intermediate 143 (95 mg) and trifluoroacetic acid (0.3 ml) in dichloromethane (5 ml) was stirred at room temperature for 2.5 hours then treated, with stirring, with 8% sodium bicarbonate solution (20 ml). The reaction mixture was stirred for 10 minutes then extracted with dichloromethane (2×15 ml). The combined organic extracts were washed with water (20 ml), dried ($Na_2SO_4$), filtered and concentrated to give a gum. A solution of the gum in diethyl ether (10 ml) was stirred and treated with a 1.0 Molar solution of ethereal hydrogen chloride (0.2 ml). The resultant suspension was stirred for 15 min. The ether was decanted. The residual solid was dried in vacuo to give the title compound as a cream powder (50 mg). Tlc. Silica. (100:8:1) mixture of dichloromethane, ethanol and ammonia (S.G,=0.88). Rf=0.05 Mass spec $MH^+$ (found)=400 $MH^+$ (calculated) 400.

Example 256 rel-(3R,3aR,6aS)-3-Isopropyl-1-methanesulfonyl-4-[4-(1-methyl-piperidin-4-yl)-butyryl]-hexahydro-pyrrolo[3,2-b]pyrrol-2-one hydrochloride Paraformaldehyde (30 mg) was added to a stirred solution of Example 255 and glacial acetic acid (1 drop) in dichloromethane (3 ml) followed, after 3 min; by sodium triacetoxyborohydride (42 mg). The reaction mixture was stirred for 2.5 hours. More sodium triacetoxyborohydride (105 mg) was added and stirring was continued for 16 hours. Sodium bicarbonate (8% aqueous solution, 10 ml) was added, with stirring, and the reaction mixture was extracted with dichloromethane (2×10 ml). The combined organics were dried ($Na_2SO_4$), filtered and concentrated to give a gum. The gum was purified by flash column chromatography on silica, using a mixture of dichloromethane, ethanol and ammonia (S.G=0.88) (100:8:1) as the eluent, to give a gum. A solution of the gum in diethyl ether (5 ml) was stirred and treated with a 1.0 Molar solution of ethereal hydrogen chloride (0.1 ml). The ether was decanted. The residual solid was dried in vacuo to give the title compound as a cream powder (17 mg). Tlc. Silica (100:8:1) Mixture of dichloromethane, ethanol and ammonia (SG.=0.88) Rf=0.27 Mass spec $MH^+$ (found)= 414 $MH^+$ (calculated)=414.

Example 257 rel-(3R,3aR,6aS)-3-Cyclopropyl-1-methanesulfonyl-4-(4-piperidin-1-yl-but-2E-enoyl)-hexahydro-pyrrolo[3,2-b]pyrrol-2-one hydrochloride Intermediate 113 (0.025 g), triethylamine (33 μl), 1-(3-dimethylaminopropyl)-3-ethylcarbodiimide hydrochloride (0.023 g), 1-hydroxybenzotriazole (0.016 g) and dimethylformamide (0.5 ml) were stirred under nitrogen for 15 min. A solution of Intermediate 149 in dry dimethylformamide (0.5 ml) was added to the resultant suspension. The mixture was stirred for a further 2.5 h and was then poured into 8% aqueous sodium hydrogen carbonate (1 ml). The mixture was extracted with ethyl acetate (2×10 ml). The combined organics were washed with water (2×10 ml) dried ($MgSO_4$) and evaporated to a yellow oil/gum which was purified by flash column chromatography using dichloromethane:ethanol:ammonia (100:8:1) as eluent to give a yellow film which was triturated with ethereal hydrogen chloride (1.0M, 2 ml) to give the title compound as a yellow solid (0.01 3 g). Tlc ($CH_2Cl_2$:EtOH:$NH_3$:100:8:1) Rf 0.6 Mass Spec. $MH^+$ (found)=396; $MH^+$ (calc)=396

Biological Data

1. The compounds were tested in the in vitro elastase test described earlier in the description. The $IC_{50}$ in μM is shown below:

| Example | HNE IC50 μM | Example | HNE IC50 μM |
|---|---|---|---|
| 1 | 0.036 | 33 | 0.458 |
| 2 | 0.137 | 34 | 0.052 |
| 3 | 0.205 | 35 | 0.697 |
| 4 | 0.134 | 36 | 0.125 |
| 5 | 0.205 | 37 | 0.138 |
| 6 | 0.07 | 38 | 0.205 |
| 7 | 0.134 | 39 | 0.189 |
| 8 | 0.029 | 40 | 0.05 |
| 9 | 0.054 | 41 | 0.084 |
| 10 | 0.039 | 42 | 0.078 |
| 11 | 0.111 | 43 | 0.408 |
| 12 | 0.06 | 44 | 0.094 |
| 13 | 0.543 | 45 | 0.531 |
| 14 | 0.193 | 46 | 0.143 |
| 15 | 0.01 | 47 | 0.109 |
| 16 | 0.267 | 48 | 0.122 |
| 17 | 0.342 | 49 | 0.412 |
| 18 | 0.069 | 50 | 0.362 |
| 19 | 5.23 | 51 | 0.055 |
| 20 | 0.057 | 52 | 0.222 |
| 21 | 0.491 | 53 | 0.143 |
| 22 | 0.06 | 54 | 0.120 |
| 23 | 0.075 | 55 | 0.038 |
| 24 | 0.009 | 56 | 0.081 |
| 25 | 0.059 | 57 | 0.027 |
| 26 | 0.02 | 58 | 0.072 |
| 27 | 0.055 | 59 | 0.039 |
| 28 | 0.064 | 60 | 0.047 |
| 29 | 0.139 | 61 | 0.242 |
| 30 | 0.189 | 62 | 0.01 |
| 31 | 0.08 | 63 | 0.006 |
| 32 | 0.286 | 64 | 0.026 |
| 65 | 0.066 | 98 | 0.159 |
| 66 | 0.034 | 99 | 0.079 |
| 67 | 0.043 | 100 | 0.65 |
| 68 | 0.073 | 101 | 0.169 |
| 69 | 0.08 | 102 | 0.091 |
| 70 | 0.041 | 103 | 0.104 |
| 71 | 0.035 | 104 | 0.574 |
| 72 | 0.037 | 105 | 0.193 |
| 73 | 0.074 | 107 | 0.143 |
| 74 | 0.055 | 108 | 0.481 |
| 75 | 0.033 | 109 | 0.096 |
| 76 | 0.176 | 110 | 0.136 |
| 77 | 0.134 | 111 | 0.58 |
| 78 | 0.087 | 112 | 0.222 |
| 79 | 0.05 | 113 | 0.304 |
| 80 | 0.061 | 114 | 0.042 |
| 81 | 0.067 | 115 | 0.314 |
| 82 | 0.162 | 116 | 0.417 |
| 83 | 0.198 | 117 | 0.027 |
| 84 | 0.134 | 118 | 0.073 |
| 85 | 0.182 | 119 | 0.034 |
| 86 | 0.103 | 120 | 0.042 |
| 87 | 0.096 | 121 | 0.014 |
| 88 | 0.075 | 122 | 0.004 |
| 89 | 0.183 | 123 | 0.014 |
| 90 | 0.305 | 124 | 0.008 |
| 91 | 0.064 | 125 | 0.013 |
| 92 | 0.07 | 126 | 0.01 |
| 93 | 0.089 | 127 | 0.04 |
| 94 | 0.081 | 128 | 0.03 |
| 95 | 0.084 | 129 | 0.014 |
| 96 | 0.134 | 130 | 0.047 |
| 97 | 0.202 | 131 | 0.102 |
| 132 | 0.083 | 165 | 0.086 |
| 133 | 0.061 | 166 | 0.287 |
| 134 | 0.023 | 167 | 0.038 |

-continued

| Example | HNE IC50 μM | Example | HNE IC50 μM |
|---|---|---|---|
| 135 | 0.041 | 168 | 0.208 |
| 136 | 0.022 | 169 | 0.029 |
| 137 | 0.045 | 170 | 0.18 |
| 138 | 0.042 | 171 | 0.039 |
| 139 | 0.055 | 172 | 0.069 |
| 140 | 0.036 | 173 | 0.065 |
| 141 | 0.176 | 174 | 0.013 |
| 142 | 0.055 | 175 | 0.074 |
| 143 | 0.033 | 176 | 0.09 |
| 144 | 0.071 | 177 | 0.02 |
| 145 | 0.039 | 178 | 0.068 |
| 146 | 0.034 | 179 | 0.047 |
| 147 | 0.096 | 180 | 0.042 |
| 148 | 0.035 | 151 | 0.042 |
| 149 | 0.046 | 182 | 0.043 |
| 150 | 0.05 | 183 | 0.046 |
| 151 | 0.085 | 184 | 0.012 |
| 152 | 0.021 | 185 | 0.033 |
| 153 | 0.114 | 186 | 0.053 |
| 154 | 0.022 | 187 | 0.043 |
| 155 | 0.426 | 188 | 0.067 |
| 156 | 0.16 | 189 | 0.062 |
| 157 | 0.209 | 190 | 0.024 |
| 158 | 0.019 | 191 | 0.041 |
| 159 | 0.017 | 192 | 0.061 |
| 160 | 0.119 | 193 | 0.05 |
| 161 | 1.029 | 194 | 0.06 |
| 162 | 0.062 | 195 | 0.068 |
| 163 | 0.103 | 196 | 0.034 |
| 164 | 0.413 | 197 | 0.153 |
| 198 | 0.127 | 230 | 0.092 |
| 199 | 0.099 | 231 | 0.035 |
| 200 | 0.053 | 232 | 0.078 |
| 201 | 0.046 | 233 | 0.062 |
| 202 | 0.038 | 234 | 0.011 |
| 203 | 0.038 | 235 | 0.009 |
| 204 | 0.098 | 236 | 0.018 |
| 205 | 0.028 | 237 | 0.029 |
| 206 | 0.087 | 238 | 0.009 |
| 207 | 0.038 | 239 | 0.018 |
| 208 | 0.054 | 240 | 0.033 |
| 209 | 0.071 | 241 | 0.022 |
| 210 | 0.103 | 242 | 0.022 |
| 211 | 0.14 | 244 | 0.011 |
| 212 | 0.03 | 245 | 0.009 |
| 213 | 0.04 | 246 | 0.021 |
| 214 | 0.464 | 247 | 0.028 |
| 215 | 0.028 | 248 | 0.06 |
| 216 | 0.087 | 249 | 0.068 |
| 217 | 0.04 | 250 | 0.021 |
| 218 | 0.026 | 251 | 0.043 |
| 219 | 0.01 | 252 | 0.014 |
| 220 | 0.012 | 253 | 0.076 |
| 221 | 0.027 | 254 | 0.097 |
| 222 | 0.107 | 255 | 0.144 |
| 223 | 0.062 | 256 | 0.078 |
| 224 | 0.41 | 257 | 0.062 |
| 225 | 0.12 | | |
| 226 | 0.087 | | |
| 227 | 0.118 | | |
| 228 | 0.068 | | |
| 229 | 0.167 | | |

Compounds of examples 2, 29, 57, 58, 59, 60, 61, 62, 63, 117, 118, 135, 136, 137, 138, 139, 140, 141, 142, 143, 144, 145, 146, 147, 148, 149, 150, 151, 152, 153, 154, 155, 158, 159, 173, 174, 175, 176, 177, 178, 179, 180, 181, 182, 183, 184, 185, 186, 187, 188, 189, 190, 191, 192, 193, 200, 201, 248, 249, 250, 251, 252, 253 and 254 were tested in the hamster test described below at an effective dose of less than 40 mg/kg, and gave a duration of effect lasting at least 6 hours.

An Oral in vivo Model Using IL-8 Induced Lung Infiltrates For the Assessment of Intracellular Elastase Inhibition Adult hamsters (100–150 g) are randomised into groups (n=4) and fasted overnight. Under gaseous anaesthetic (3% isofluorane) animals are dosed orally with 1 mL/100 g water as vehicle or containing predissolved compounds. Either at the same time, or subsequently under anaesthetic, animals are dosed intratracheally with 1 ug recombinant human IL-8 in 100 uL sterile saline. Six hours after IL-8 dosing animals are sacrificed using intrapertoneal pentobarbitone. The lungs are ravaged with 2×2.5 mL sterile saline and femurs are removed by dissection.

Intracellular elastase is prepared from neutrophils collected by lavage and from femoral bone marrow. This is achieved by sonication of the neutrophils and centrifugation to yield intracellular granules. These are disrupted by freeze/thawing and sonication. Elastase and myeloperoxidase assays are then performed on these samples to assess the efficacy of the compounds and to normalise for neutrophil recovery.

What is claimed is:

1. A process for preparation of a compound of formula (XXVIII)$^3$

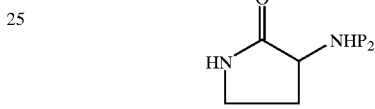

(XXVIII)$^3$ wherein $P_2$ is a protecting group, or a derivative in which the ring nitrogen is protected, or a salt thereof, which comprises the steps of:

(i) cyclizing a compound of formula (XLIV)$^1$ (XLIV)$^1$ $^+$SMeRX$^-$ $P_2$NH    CONHP$^{1*}$ wherein RX is selected from methyl iodide, benzyliodide and Me$_2$SO$_4$, and P$^{1*}$ represents CBZ, BOC or trifluoroacetyl; and (ii) optionally protecting or deprotecting the product of step (i) and/or forming a salt thereof.

2. A process according to claim 1 wherein the compound of formula (XLIV)$^1$ is present as a single purified enantiomer of formula (XLIV)$^2$

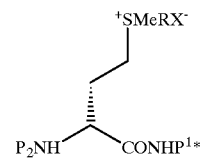

(XLIV)$^2$ wherein RX and P$^{1*}$ are as defined in claim 1.

3. A process according to claim 1 wherein P$^{1*}$ represents CBZ or BOC.

4. A process according to claim 1 wherein P$_2$ represents trifluoroacetyl.

5. A process for preparation of a compound of formula (I)

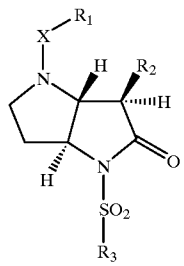

(I)

(relative stereochemistry indicated)

wherein:

R$_1$ represents C$_{1-6}$alkyl; C$_{2-6}$ alkenyl; aryl, aryl-C$_{1-4}$alkyl, aryl-C$_{2-4}$alkenyl, heteroaryl, heteroaryl-C$_{1-4}$ alkyl, or heteroaryl-C$_{2-4}$alkenyl, or such a group in which the aryl or heteroaryl moiety is substituted by one or more C$_{1-4}$alkyl, halo, tetrazolyl, trifluoromethyl-sulphonamide, NR$_9$CO—C$_{1-8}$alkyl, —(CH$_2$)$_m$—NR$_4$R$_5$, —CN, —COOR$_9$, —CONR$_9$R$_{10}$, —NO$_2$, —SO$_2$—C$_{1-6}$alkyl —CF$_3$ or C$_{1-6}$ alkoxy groups; —(CH$_2$)$_n$—NR$_4$R$_5$; C$_{2-8}$alkenyl-NR$_4$R$_5$; —(CH$_2$)$_n$CONR$_4$R$_5$; —(CH$_2$)$_n$NR$_9$CO—C$_{1-6}$alkyl; C$_{2-8}$alkenyl-COOR$_9$; (CH$_2$)$_n$COOR$_9$; and C$_{2-8}$alkenyl CONR$_4$ R$_5$;

X represents

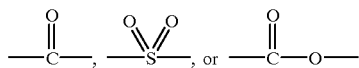

(where carbonyl is bound to the ring nitrogen);

R$_2$ represents C$_{2-4}$alkyl, C$_{2-4}$alkenyl, C$_{1-3}$alkoxy or C$_{1-3}$alkylthio;

R$_3$ represents C$_{1-6}$alkyl; —CH$_2$(CF$_2$)$_{0-4}$CF$_3$; aryl or heteroaryl, which aryl or heteroaryl are mono-ring, or have two fused rings one of which may be saturated, and which aryl and heteroaryl groups may be substituted by one or more C$_{1-4}$alkyl, halo, —NR$_7$R$_8$, —SO$_2$NR$_7$R$_8$, —CONR$_7$R$_8$, —C$_{1-6}$alkyl ester, —CN, —CH$_2$OH, —O—C$_{1-6}$alkyl, —CF$_3$, or nitro groups; aryl-C$_{1-4}$alkyl, aryl-C$_{1-4}$alkyl-NH— or aryl-C$_{2-4}$ alkenyl, or such groups wherein aryl is substituted by one or more C$_{1-4}$alkyl or halo groups;

R$_4$ and R$_5$ independently represent hydrogen, C$_{1-4}$ alkyl, C$_{1-4}$alkoxy, —(CH$_2$)$_{1-4}$CONR$_{11}$R$_{12}$, —CO—C$_{1-4}$alkyl or phenyl optionally substituted by one or more C$_{1-4}$alkyl or halogen groups or R$_4$ and R$_5$ may be joined such that NR$_4$R$_5$ represents a mono, bi- or tri-cyclic ring system containing 4–15 ring carbon atoms, wherein one or more rings may be optionally interrupted by one or more heteroatoms selected from O, N and S and wherein one or more ring carbon atoms may have carbonyl functionality;

or —(CH$_2$)$_n$—NR$_4$R$_5$ may represent a group of formula 1a:

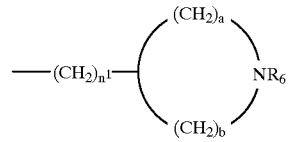

(1a)

wherein R$_6$ is hydrogen or a carboxy C$_{1-6}$ alkyl ester, n$^1$ is 0–6 and a and b independently represent an integer 0–3 provided a+b is in the range 3–5;

R$_7$, R$_8$, R$_9$, R$_{10}$, R$_{11}$, R$_{12}$ independently represent hydrogen or C$_{1-4}$ alkyl;

m represents an integer 0 to 8; n represents an integer 1 to 9;

or a salt or a solvate thereof which comprises the steps of:

(a) preparation of a compound of formula (XXVIII)$^3$

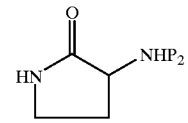

(XXVIII)$^3$ wherein P$_2$ is a protecting group, or a derivative in which the ring nitrogen is protected, or a salt thereof, which comprises the steps of:

(i) cyclizing a compound of formula (XLIV)$^1$

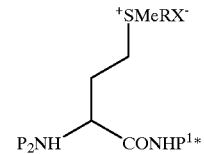

(XLIV)$^1$ wherein RX and P$^{1*}$ are as defined in claim 1; and (ii) optionally protecting or deprotecting the product of step (i) and/or forming a salt thereof; and (b) reduction of a compound of formula (XXVIII)$^3$ or a derivative thereof in which one or both nitrogen atoms is protected, to give a compound of formula (XXIX)$^2$

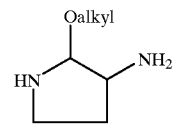

(XXIX)$^2$ or a derivative thereof in which one or both nitrogen atoms is protected; and (c) reacting a compound of formula (XXIX)$^2$, or a derivative thereof in which one or both nitrogen atoms is protected, with a compound of formula (XXX)

(XXX)

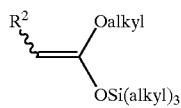

or a compound of formula (XXX)²

(XXX)²

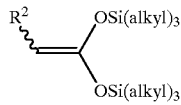

wherein R² is as defined above, to give a compound of formula (XL)¹

(XL)¹

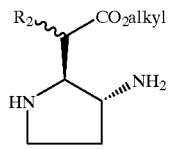

wherein $R_2$ is as defined above; and
(d) cyclization of a compound of formula (XL)¹ to give a compound of formula (XXIII)

(XXIII)

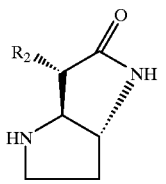

wherein $R_2$ is as defined above; and
(e)
  (i) sulphonation of a compound of formula (XXIII) or a derivative in which amine nitrogen is protected to give a compound of formula (II)

(II)

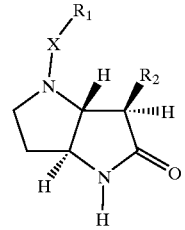

wherein $R_2$ and $R_3$ are as defined above; and
  (ii) if necessary, deprotection of the amine nitrogen, followed by condensation of a compound of formula (II) with a compound $R_1COOH$, RCOY, $R_1OCOY$ or $R_1SO_2Y$, where Y is a reactive group to give a compound of formula (I); or
(f)
  (i) condensation of a compound of formula (XXIII), or a derivative in which the amide nitrogen is protected, with a compound $R_1COOH$, RCOY, $R_1OCOY$ or $R_1SO_2Y$, where Y is as defined above to give a compound of formula (III)¹

(III)¹ wherein:
$R_1$, $R_2$ and X are as defined above; and
  (ii) if necessary deprotection of the amide nitrogen followed by sulphonation to give a compound of formula (I).

6. A process according to claim 4 wherein P¹* represents CBZ and $P_2$ represents trifluoroacetyl.

* * * * *